(12) United States Patent
Newstrom et al.

(10) Patent No.: US 11,492,584 B2
(45) Date of Patent: *Nov. 8, 2022

(54) WELL PLATE INCUBATOR

(71) Applicant: Berkeley Lights, Inc., Emeryville, CA (US)

(72) Inventors: Russell A. Newstrom, Alameda, CA (US); Andrew W. McFarland, Berkeley, CA (US); Darcy K. Kelly-Greene, Pleasanton, CA (US); J. Tanner Nevill, El Cerrito, CA (US); Gang F. Wang, Mountain View, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 276 days.

This patent is subject to a terminal disclaimer.

(21) Appl. No.: 16/537,389

(22) Filed: Aug. 9, 2019

(65) Prior Publication Data

US 2020/0032193 A1 Jan. 30, 2020

Related U.S. Application Data

(63) Continuation of application No. 15/282,923, filed on Sep. 30, 2016, now Pat. No. 10,407,658.

(Continued)

(51) Int. Cl.
*C12M 1/00* (2006.01)
*C12M 1/12* (2006.01)
(Continued)

(52) U.S. Cl.
CPC ............ *C12M 41/14* (2013.01); *C12M 23/12* (2013.01); *C12M 23/38* (2013.01); *C12M 23/46* (2013.01);
(Continued)

(58) Field of Classification Search
None
See application file for complete search history.

(56) References Cited

U.S. PATENT DOCUMENTS 4,701,415 A 10/1987 Dutton et al.
5,484,731 A 1/1996 Stevens
(Continued)

FOREIGN PATENT DOCUMENTS

CN 102428168 A 4/2012
CN 102719352 A 10/2012
(Continued)

OTHER PUBLICATIONS

Document entitled Bioluminescence-measuring device and kit of measuring intracellular ATP, machine translation of JP 2004313028 A provided by Proquest; original document provided in Applicant's Feb. 25, 2022 IDS (Year: 2004).*

(Continued)

*Primary Examiner* — Holly Kipouros
(74) *Attorney, Agent, or Firm* — Shay Glenn LLP

(57) ABSTRACT

Incubators including an enclosure with an internal chamber configured to support a cell culture plate comprising a plurality of wells are disclosed. The enclosure includes a plurality of openings configured to allow access to the wells. The incubators include a sealing element configured to seal the plurality of openings in the enclosure. The sealing element comprises a plurality of openings corresponding to at least a subset of the plurality of openings in the enclosure. Access to the internal chamber can be provided by aligning the plurality of openings in the sealing element with the plurality of openings in the enclosure. Methods for using the incubators are also provided.

36 Claims, 28 Drawing Sheets

Related U.S. Application Data

(60) Provisional application No. 62/235,863, filed on Oct. 1, 2015.

(51) Int. Cl.
  *C12M 1/32* (2006.01)
  *C12M 3/00* (2006.01)
  *C12M 1/02* (2006.01)
  *C12M 1/34* (2006.01)
  *C12M 1/36* (2006.01)

(52) U.S. Cl.
  CPC .......... *C12M 37/04* (2013.01); *C12M 41/22* (2013.01); *C12M 41/32* (2013.01); *C12M 41/34* (2013.01); *C12M 41/48* (2013.01)

(56) References Cited

U.S. PATENT DOCUMENTS

| | | | |
|---|---|---|---|
| 5,681,492 A | 10/1997 | Van Praet | |
| 5,952,219 A * | 9/1999 | Zamoyski | C12M 33/22 |
| | | | 435/308.1 |
| 6,037,168 A | 3/2000 | Brown | |
| 6,054,100 A | 4/2000 | Stanchfield et al. | |
| 6,114,674 A | 9/2000 | Baugh et al. | |
| 6,309,608 B1 | 10/2001 | Zhou et al. | |
| 9,081,001 B2 | 7/2015 | Cook et al. | |
| 10,407,658 B2 | 9/2019 | Newstrom et al. | |
| 2001/0019705 A1 | 9/2001 | Ruediger et al. | |
| 2001/0050276 A1 | 12/2001 | Inami | |
| 2003/0044969 A1 | 3/2003 | Shin et al. | |
| 2003/0072679 A1 | 4/2003 | Johnson et al. | |
| 2003/0153021 A1* | 8/2003 | Lu | C12M 41/36 |
| | | | 435/287.1 |
| 2003/0170147 A1* | 9/2003 | Voegelin | B01L 3/5025 |
| | | | 422/400 |
| 2004/0018122 A1 | 1/2004 | Micklash et al. | |
| 2004/0151621 A1 | 8/2004 | Seto et al. | |
| 2006/0024209 A1 | 2/2006 | Agnew | |
| 2006/0191893 A1 | 8/2006 | Weinfield et al. | |
| 2008/0090287 A1* | 4/2008 | Larsen | C12M 23/12 |
| | | | 435/287.5 |
| 2008/0220481 A1 | 9/2008 | Mortillaro et al. | |
| 2010/0008828 A1 | 1/2010 | Cahilly | |
| 2010/0009335 A1 | 1/2010 | Joseph et al. | |
| 2010/0173400 A1 | 7/2010 | Atwood et al. | |
| 2012/0329143 A1 | 12/2012 | Yamazaki et al. | |
| 2013/0036755 A1 | 2/2013 | Kang | |
| 2013/0059322 A1 | 3/2013 | Hung et al. | |
| 2013/0109081 A1 | 5/2013 | Tsuchiya | |
| 2014/0160559 A1 | 6/2014 | Mermelstein et al. | |
| 2014/0273191 A1 | 9/2014 | Tipgunlakant et al. | |
| 2015/0334774 A1 | 11/2015 | Schryver et al. | |
| 2020/0017817 A1 | 1/2020 | Kelly-Greene et al. | |

FOREIGN PATENT DOCUMENTS

| | | |
|---|---|---|
| CN | 104937093 A | 9/2015 |
| CN | 105518458 A | 4/2016 |
| JP | S57100900 A | 6/1982 |
| JP | S60259178 A | 12/1985 |
| JP | 2001504692 A | 4/2001 |
| JP | 2001521379 A | 11/2001 |
| JP | 2001352969 A | 12/2001 |
| JP | 2004313028 A | 11/2004 |
| JP | 2005502884 A | 1/2005 |
| JP | 2005176839 A | 7/2005 |
| JP | 3133920 U | 7/2007 |
| JP | 2008505629 A | 2/2008 |
| JP | 2008209375 A | 9/2008 |
| JP | 2009507238 A | 2/2009 |
| JP | 2009201509 A | 9/2009 |
| JP | 2009251297 A | 10/2009 |
| JP | 2009284810 A | 12/2009 |
| JP | 2010521148 A | 6/2010 |
| JP | 2010532173 A | 10/2010 |
| JP | 2012529896 A | 11/2012 |
| JP | 2013007688 A | 1/2013 |
| JP | 2016514950 A | 5/2016 |
| JP | 2016529889 A | 9/2016 |
| TW | 201525131 A | 7/2015 |
| WO | WO98/20106 A1 | 11/1996 |
| WO | WO2003/085379 A2 | 10/2003 |
| WO | WO2004/071665 A1 | 8/2004 |
| WO | WO2009/103416 A1 | 8/2009 |
| WO | WO2010/110754 A1 | 9/2010 |
| WO | WO2010/147078 A1 | 12/2010 |
| WO | WO2014/081840 A1 | 5/2014 |
| WO | WO2017/059273 A1 | 4/2017 |

OTHER PUBLICATIONS

Chiou et al.; Massively Parallel Manipulation of Single Cells and Microparticles Using Optical Images; Nature; (436) pp. 370-372; Jul. 2005.

Hsu et al.; Sorting of Differentiated Neurons Using Phototransistor-Based Optoelectronic Tweezers for Cell Replacement Therapy of Neurodegenerative Diseases; Transducers 2009 Conf.; pp. 1598-1601; Jun. 2009.

IBIDI; "Air Pressure Generator"; Product webpage; 2 pages; retrieved from the internet (https://ibidi.com/gas-incubation-systems/137-air-pressure-generator.html) on Aug. 29, 2018.

IBIDI; "Heated Plate, Universal Fit, for 4 μ-Slides"; Product webpage; 4 pages; retrieved from the internet (https://ibidi.com/heating-systems-for-slides-dishes/124-heated-plate-in-multi-well-format-for-4-slides.html) on Aug. 29, 2018.

IBIDI; "Heating Insert μ-Dish 35 mm, high for ibidi Heating System, Universal Fit"; Product webpage; 4 pages; retrieved from the internet (https://ibidi.com/16-ibidi-heating-systems-universal-fit) on Aug. 29, 2018.

IBIDI; "Heating Insert μ-Dish 35 mm, low for ibidi Heating System, Universal Fit"; Product webpage; 4 pages; retrieved from the internet (https://ibidi.com/heating-systems-for-slides-dishes/128-heating-insert-dish-35-mm-low-for-ibidi-heating-system-universal-fit.html) on Aug. 29, 2018.

IBIDI; "Heating Insert μ-Slide for ibidi Heating System, Universal Fit"; Product webpage; 4 pages; retrieved from the internet (https://ibidi.com/heating-systems-for-slides-dishes/130-heating-insert-slide-for-ibidi-heating-system-universal-fit.html) on Aug. 29, 2018.

IBIDI; "Heating Insert Adapter for perfusion assays"; Product webpage; 4 pages; retrieved from the internet (https://ibidi.com/heating-systems-for-slides-dishes/131-heating-insert-adapter-for-perfusion-assays.html) on Aug. 29, 2018.

IBIDI; "Heating Insert LabTek for ibidi Heating System, Universal Fit"; Product webpage; 4 pages; retrieved from the internet (https://ibidi.com/heating-systems-for-slides-dishes/127-heating-insert-for-ibidi-heating-system-universal-fit.html) on Aug. 29, 2018.

IBIDI; "ibidi Gas Incubation System for CO2 and O2"; Product webpage; 9 pages; retrieved from the internet (https://ibidi.com/gas-incubation-systems/136-ibidi-gas-incubation-system-for-co2-and-o2.html) on Aug. 29, 2018.

IBIDI; "ibidi Gas Incubation System for CO2"; Product webpage; 9 pages; retrieved from the internet (https://ibidi.com/gas-incubation-systems/135-ibidi-gas-incubation-system-for-co2.html) on Aug. 29, 2018.

IBIDI; "ibidi Heating System, Multi-Well Plates for Nikon Ti-S-E and TI-S-ER"; Product webpage; 10 pages; retrieved from the internet (https://ibidi.com/heating-systems-for-multiwell-plates/125-ibidi-heating-system-multi-well-plates.html) on Aug. 29, 2018.

IBIDI; "ibidi Heating System, Multi-Well Plates, K-Frame"; Product webpage; 10 pages; retrieved from the internet (https://ibidi.com/heating-systems-for-multiwell-plates/126-ibidi-heating-system-multi-well-plates-k-frame.html) on Aug. 29, 2018.

IBIDI; "ibidi Heating System, Universal Fit, for 1 Chamber"; Product webpage; 11 pages; retrieved from the internet (https://ibidi.com/heating-systems-for-slides-dishes/122-ibidi-heating-system-universal-fit-for-1-chamber.html) on Aug. 29, 2018.

(56) References Cited

OTHER PUBLICATIONS

IBIDI; "ibidi Heating System, Universal Fit, for 4 µ-Slides"; Product webpage; 11 pages; retrieved from the internet (https://ibidi.com/heating-systems-for-slides-dishes/123-ibidi-heating-system-universal-fit-for-4-slides.html) on Aug. 29, 2018.

IBIDI; "Modification Heated Lid ibidi Heating System, Universal Fit, for Perfusion Assays"; Product webpage; 4 pages; retrieved from the internet (https://ibidi.com/heating-systems-for-slides-dishes/132-modification-heated-lid-ibidi-heating-system-universal-fit-for-perfusion-assays.html) on Aug. 29, 2018.

INHECO GMBH; "Single Plate Incubators"; 4 pgs.; Oct. 14, 2017.

Nevill et al.; Integrated Microfluidic Cell Culture and Lysis on a Chip; Lab Chip; (12) pp. 1689-1695; Oct. 2007.

OKOLAB; "Cage Incubator"; Product webpage; 17 pages; retrieved from the internet (http://www.oko-lab.com/live-cell-imaging/cage-incubator) on Aug. 29, 2018.

OKOLAB; "Heating and Cooling"; Product webpage; 14 pages; retrieved from the internet (http://www.oko-lab.com/live-cell-imaging/heating-cooling) on Aug. 29, 2018.

OKOLAB; "Objective Heater"; Product webpage; 4 pages; retrieved from the internet (http://www.oko-lab.com/live-cell-imaging/objective-heater) on Aug. 29, 2018.

OKOLAB; "Stage Top Incubator"; Product webpage; 15 pages; retrieved from the internet (http://www.oko-lab.com/live-cell-imaging/stage-top-digital-gas) on Aug. 29, 2018.

Somaweera et al.; "Generation of a Chemical Gradient Across an Array of 256 Cell Cultures in a Single Chip"; Analyst; 138(19); 14 pgs.; (Author Manuscript); Oct. 2013.

Valley et al.; Optoelectronic Tweezers as a Tool for Parallel Single-Cell Manipulation and Stimulation; IEEE Trans Biomed Circuits Syst.; 3(6); pp. 424-431; Dec. 2009.

Yi et al.; Microfluidics Technology for Manipulation and Analysis of Biological Cells; Anal Chim Acta; (560) pp. 1-23; Feb. 2006.

Corning; Surface areas and guide for recommended medium volumes for corning cell culture vessels; 4 pages; retrieved from the internet (https://www.corning.com/catalog/cls/documents/application-notes/CLS-AN-209.pdf) on Apr. 2, 2021.

Ritchie et al.; Reconstitution of Membrane Proteins in Phospholipid Bilayer Nanodiscs; Methods Enzymol; 464; pp. 211-231; 23 pages; (Author Manuscript); Jan. 2009.

JP2004313028_Kamahori, Machine Translation, Nov. 11, 2004, 31 pages.

JP2009201509A_Isono, Machine Translation, Sep. 10, 2009, 16 pages.

JP2009251297A_Tsuchiya, Machine Translation, Oct. 29, 2009, 15 pages.

Z Report_The international Search Report and the Written Opinion of the International Searching Authority, PCT Application Serial No. PCT/US2016/054829 (dated Feb. 3, 2017), 20 pages.

Z Report_The International Search Report and the Written Opinion of the International Searching Authority, PCT Application Serial No. PCT/US2017/064357 (dated Apr. 5, 2018), 11 pages.

* cited by examiner

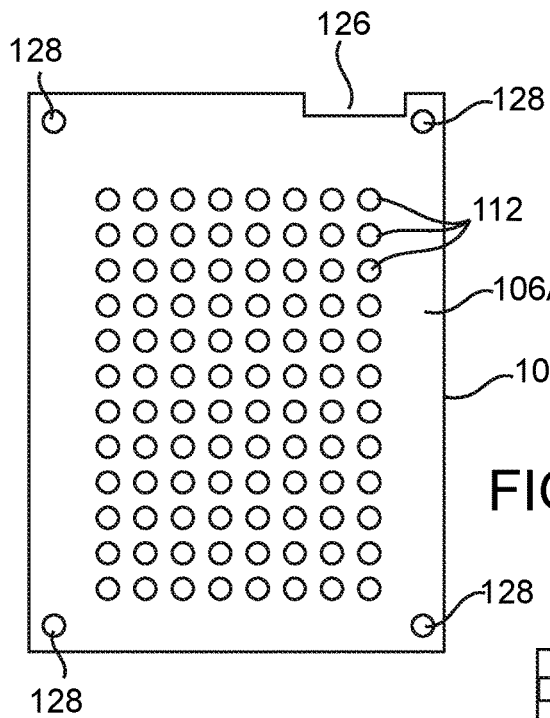
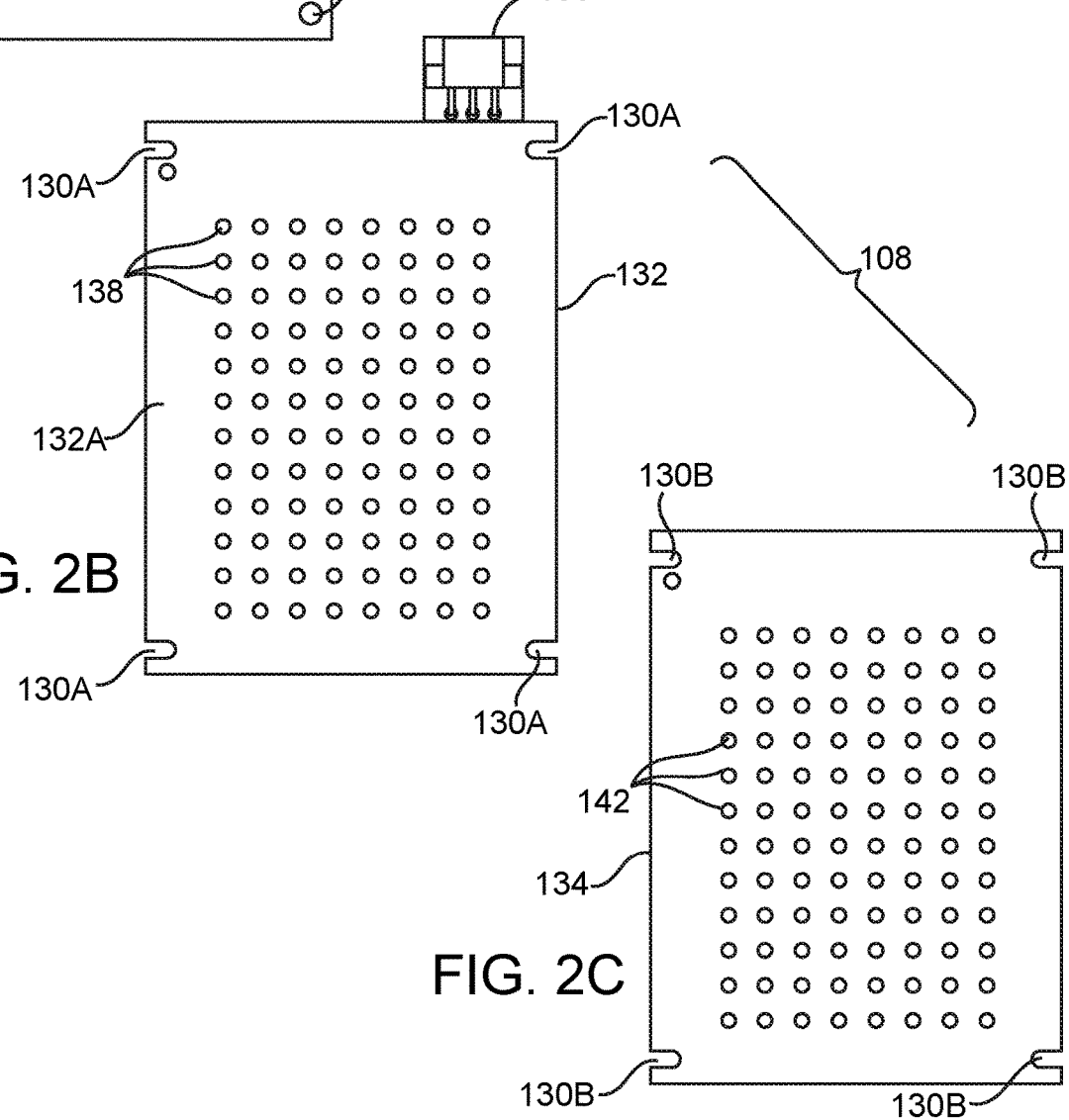

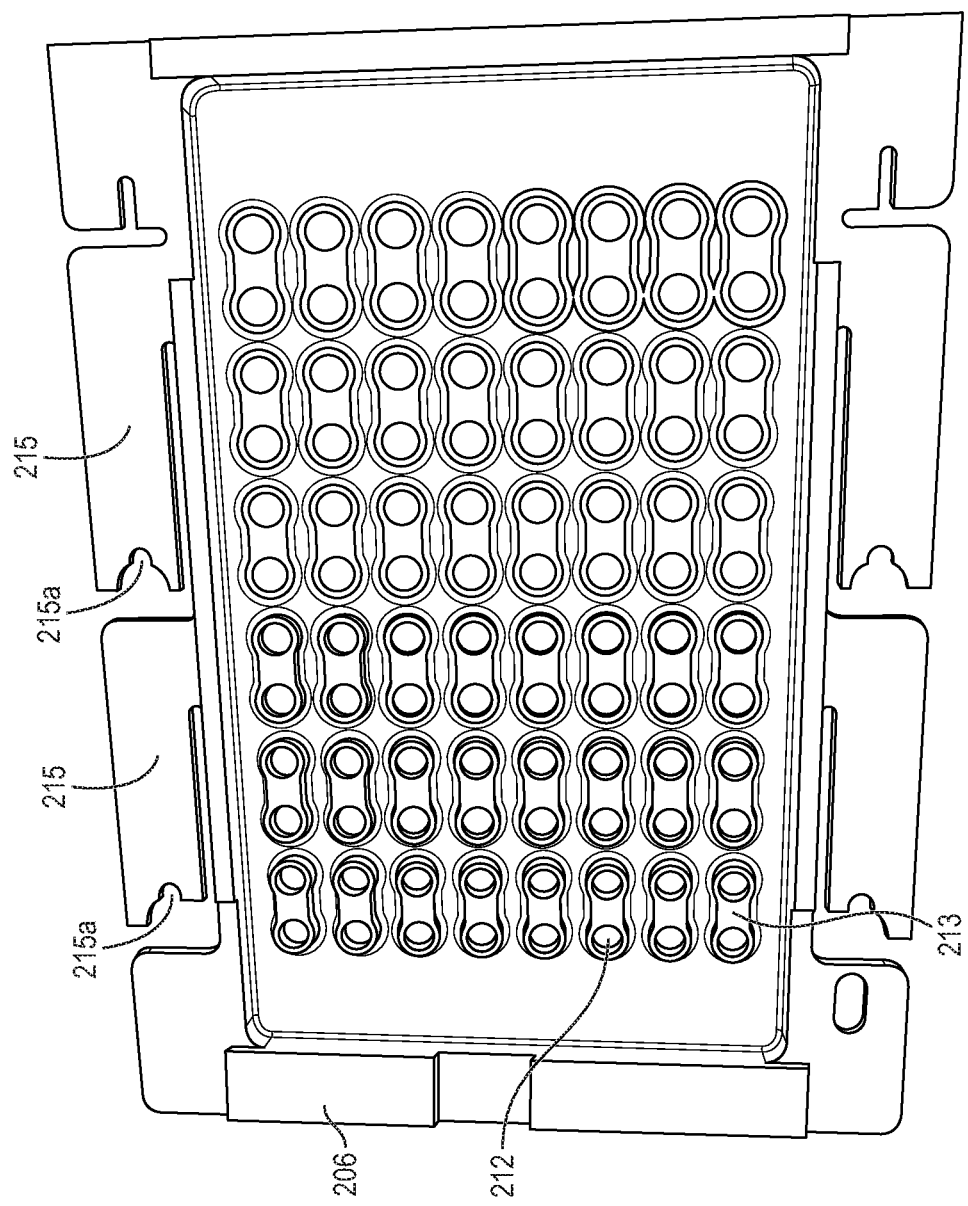

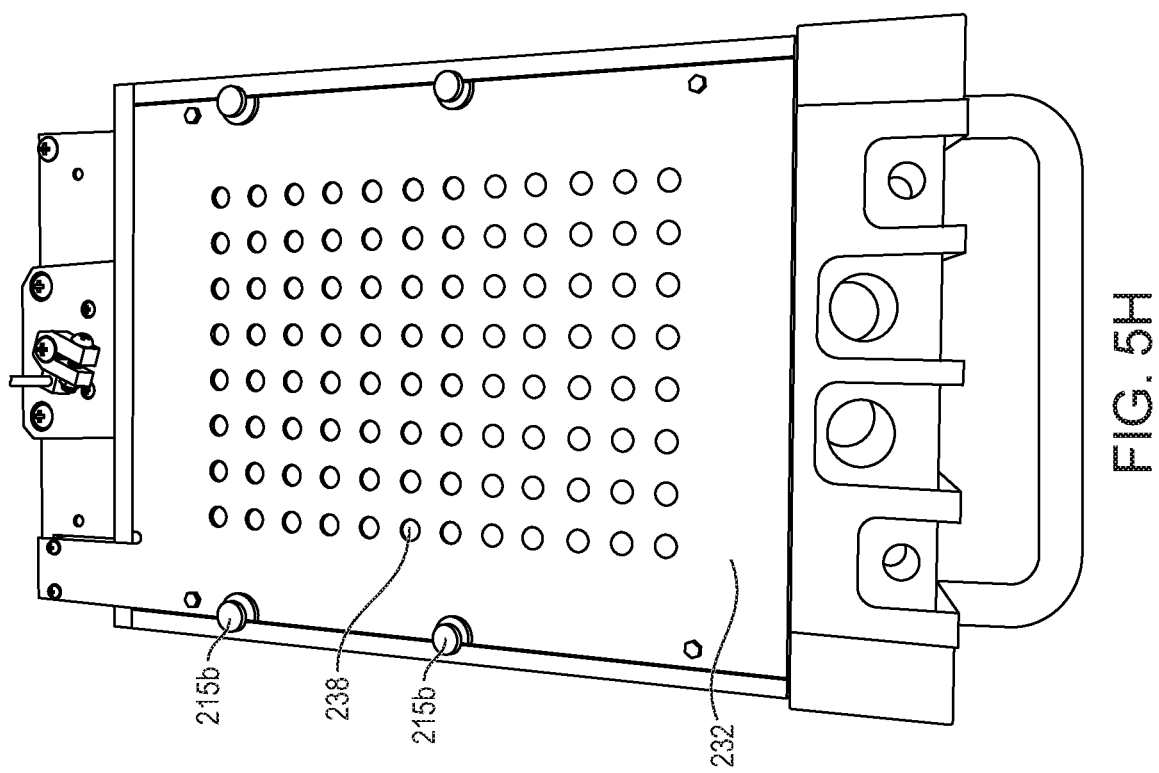

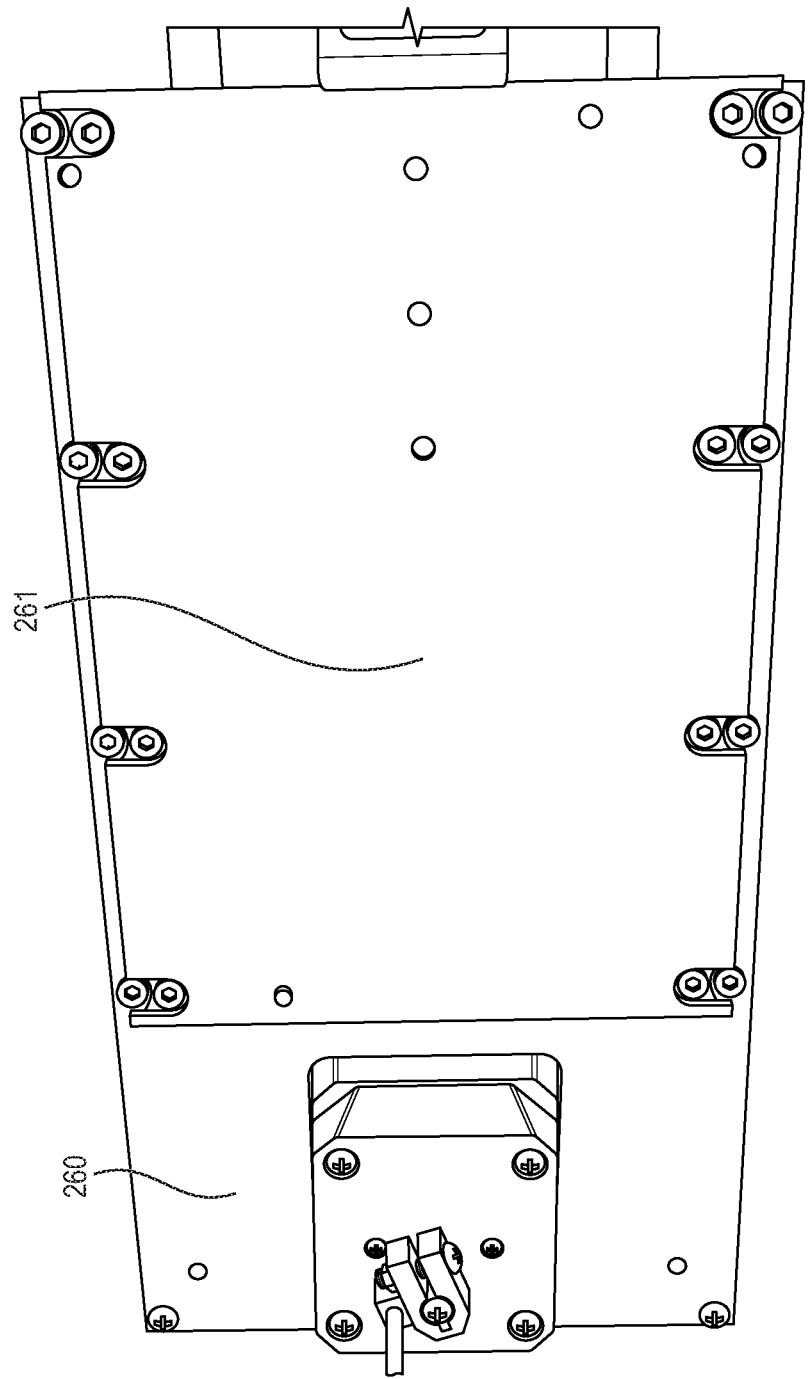

WELL PLATE INCUBATOR

CROSS REFERENCE TO RELATED APPLICATIONS

This application is a continuation of U.S. patent application Ser. No. 15/282,923 titled "Well Plate Incubator" filed on Sep. 30, 2016, which claims the benefit under 35 U.S.C. § 119 of U.S. Patent Application No. 62/235,863 titled "Well-Plate Incubator" filed on Oct. 1, 2015, the disclosure of which is incorporated herein by reference.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Incubators can be used to hold samples containing materials, including micro-objects and other components derived from biological cells, and provide conditions to maintain the viability of biologically related materials. For example, the interior environment of the incubator can have a certain temperature range, humidity, and carbon dioxide content selected to maintain the viability of the materials.

The materials maintained within the incubator can be accessed by opening the incubator. However, opening the incubator, such as by opening a lid of the incubator, can introduce contaminants and disrupt the interior environment of the incubator. Repeated opening can adversely affect the biological viability of the materials within the incubator.

Accessing the interior of the incubator with a robotic arm can also be difficult to automate because of the significant complexity of movement required by the robotic arm in order to open and access the interior of the incubator. Even if the robotic arm is configured to access the incubator after opening the lid, the extra steps can significantly decrease process throughput. Repeated opening of the lid in combination with the use of a robotic arm can adversely affect the materials. One solution that has been developed to address this problem is to locate the robotic arm and incubator within a larger incubator having an internal environment with conditions selected to maintain viability of the materials. However, this solution creates additional problems for the equipment operating within the incubator environment. For example, the tooling and equipment maintained in the environment is subject to additional condensation that can damage or inhibit the robotic arm. Enlarging the incubator environment also greatly increases the complexity and costs of the system.

A need therefore exists for an incubator that addresses many of these issues and that can be easily accessed by a robotic arm or other import/export tip while maintaining the internal incubator environment to support the viability of biological and other materials.

SUMMARY OF THE DISCLOSURE

The present invention relates to incubators having a plurality of openings that can provide access to wells in a cell culture plate supported within the incubator. The incubators can improved access while preventing contamination of the environment within the incubator.

In one aspect of the invention, an incubator is provided, where the incubator includes an enclosure having an internal chamber configured to support a cell culture plate comprising a plurality of wells, the enclosure including a plurality of openings configured to allow access to the wells of the cell culture plate; and a sealing element configured to seal the plurality of openings in the enclosure, the sealing element including a first plurality of openings corresponding to at least a subset of the plurality of openings in the enclosure.

In some embodiments of the incubator, each opening of the plurality of openings in the enclosure may have a diameter of about 1 mm to about 10 mm. In some other embodiments, each opening of the plurality of openings in the enclosure may have a diameter of about 1 mm to about 5 mm, or about 1.0 mm, about 1.5 mm, about 2.0 mm, about 2.5 mm, about 3.0 mm, about 3.5 mm, about 4.0 mm, about 4.5 mm, or about 5.0 mm, or any range defined by one of the foregoing sizes.

In various embodiments of the incubator, the internal chamber of the enclosure may have a volume of about 50 $cm^3$ to about 300 $cm^3$. In other embodiments, the internal chamber may have a volume of about 100 $cm^3$ to about 500 $cm^3$. In yet other embodiments, the internal chamber may have a volume of about 200 $cm^3$ to about 750 $cm^3$. Alternatively, the internal chamber may have a volume of about 400 $cm^3$ to about 1,000 $cm^3$. In further embodiments, the internal chamber may have a volume of about 500 $cm^3$ to about 1500 $cm^3$. In other embodiments, the internal chamber may have a volume of about 750 $cm^3$ to about 2000 $cm^3$.

In various embodiments of the incubator, the cell culture plate may be a 96-well plate. In other embodiments, the cell culture plate may be a 384-well plate. In some other embodiments, the cell culture plate may have 24 or fewer wells (e.g., 12 wells, 6 wells, etc.).

In various embodiments of the incubator, the enclosure may include a base and a lid, the base and the lid defining the internal chamber. In other embodiments, the enclosure may include a base, a lid, and a front plate, the base, the lid, and the front plate defining the internal chamber. The base may be formed from a rigid material having a high thermal conductivity and low thermal capacitance. In some embodiments, the base may be configured with a hollow region forming part or all of the internal chamber of the enclosure. In some embodiments, the base may include a bottom and four walls with one of the four walls having a height that is shorter than the height of the other three walls. In various embodiments, the lid is formed from an insulating plastic. In some embodiments, the lid may include an outer surface (e.g., a surface that interfaces with air located outside of the incubator) and an inner surface within the enclosure (e.g., a surface that interfaces with air located within the inner chamber of the enclosure). The inner surface of the lid may include one or more recesses. In some embodiments, the lid may include one or more connectors configured to sealably connect the lid to the base. In some embodiments, the one or more connectors may include a magnet, a tab (e.g., a flexible tab), and/or a clip.

In various embodiments of the incubator, the plurality of openings in the enclosure may be configured to be in register with the plurality of wells in the cell culture plate. In some embodiments, access to the internal chamber of the enclosure, and any cell culture plate contained therein, may be provided by positioning the sealing element such that one or more of the plurality of openings in the enclosure is in register with one or more openings in the sealing element. In various embodiments, the sealing element may be movable between a closed position, in which the sealing element occludes each of the plurality of openings in the enclosure, and a first open position, in which the first plurality of openings of the sealing element are in register with the at least a subset of the plurality of openings in the enclosure. In some embodiments, the number of openings in the first plurality of openings of the sealing element may be the same as the number of openings in the enclosure. In other embodiments, the number of openings in the first plurality of openings of the sealing element may be less than the number of openings in the enclosure.

In some embodiments, the sealing element may further include a second plurality of openings, the second plurality of openings being different from the first plurality of openings. In some embodiments, the number of openings in the first plurality of openings and/or the second plurality of openings in the sealing element is less than the number of openings in the enclosure. In various embodiments, the sealing element may further include a third plurality of openings, the third plurality of openings being different from the first plurality of openings and the second plurality of openings. In some of the embodiments, the number of openings in the first plurality of openings, the second plurality of openings, and/or the third plurality of openings in the sealing element may be less than the number of openings in the enclosure. For example, the number of openings in each of the first plurality of openings, the second plurality of openings, and the third plurality of openings in the sealing element can be less than the number of openings in the enclosure, while the sum of the first, second, and third pluralities of openings in the sealing element can be equal to the number of openings in the enclosure. In some embodiments, the number of openings in the second plurality of openings in the sealing element may be one-half, one-third, or one-fourth the number of openings in the enclosure. In some embodiments, the number of openings in the third plurality of openings in the sealing element may be one-third or one-fourth the number of openings in the enclosure.

In some embodiments, each of the plurality of openings in the sealing element may have a diameter of about 1 mm to about 10 mm. In other embodiments, each of the plurality of openings in the sealing element has a diameter of about 1 mm to about 5 mm, or about 1.0 mm, about 1.5 mm, about 2.0 mm, about 2.5 mm, about 3.0 mm, about 3.5 mm, about 4.0 mm, about 4.5 mm, about 5.0 mm, or any range defined by one of the foregoing sizes.

In various embodiments of the incubator, the sealing element may be located inside the internal chamber of the enclosure. In various embodiments, the sealing element may be movable between a closed position and a first open position, wherein, when the sealing element is in the closed position, each of the plurality of openings in the enclosure may be occluded, and when the sealing element is in the first open position, a first plurality of openings in the sealing element may be in register with a first subset of the plurality of opening in the enclosure and all other openings (if any) of the plurality of openings in the enclosure may be occluded. In related embodiments, the sealing element may be further movable to a second open position, wherein, when the sealing element is in the second open position, a second plurality of openings in the sealing element (which may be identical to or different than the first plurality of openings in the sealing element) may be in register with a second subset of openings in the enclosure and all other openings of the plurality of openings in the enclosure may be occluded. In some embodiments, the first subset of openings in the enclosure and the second subset of openings in the enclosure may be non-overlapping subsets. In other related embodiments, the sealing element may be further movable to a third open position, wherein when the sealing element is in the third open position, a third plurality of openings in the sealing element (which may be identical to or different than the first plurality and/or second plurality of openings in the sealing element) may be in register with a third subset of openings in the enclosure and all other openings of the plurality of openings in the enclosure may be occluded. In some embodiments, the first, second, and third subsets of openings in the enclosure may be non-overlapping subsets. In some embodiments, the first, second, and third subsets of openings in the enclosure may be overlapping subsets (e.g., partially overlapping).

In various embodiments of the incubator, the incubator may further include a sealing element actuator configured to move the sealing element between a first open position and a closed position. In some embodiments, the sealing element actuator may be configured to move the sealing element between a second open position and the closed position. In some embodiments, the sealing element actuator may be configured to move the sealing element between a third open position and the closed position. In some embodiments, moving the sealing element to the first open position may include aligning openings of the sealing element (e.g., a first plurality of openings) with a first subset of the plurality of openings in the enclosure. In some embodiments, moving the sealing element to the second open position may include aligning openings of the sealing element (e.g., the first plurality of openings or a second plurality of openings) with a second subset of the plurality of openings in the enclosure. In some embodiments, moving the sealing element to the third open position may include aligning openings of the sealing element (e.g., the first plurality of openings, the second plurality of openings, or a third plurality of openings) with a third subset of the plurality of openings in the enclosure. In some embodiments, the sealing element actuator may include a motor or rotary solenoid.

In various embodiments of the incubator, the incubator may further include at least one passage in the enclosure configured for gas entry. In some embodiments, the at least one passage configured for gas entry may be located on a wall of the base, at the same height from a bottom of the base as a side of a cell culture plate held by a support within the inner chamber of the enclosure. In various embodiments of the incubator, the incubator may further include a connector adapted to connect a pressurized gas source to a passage in the enclosure configured for gas entry. In related embodiments, the sealing element may be configured to form a seal with the plurality of openings in the enclosure that allows the enclosure to maintain a pressure in the internal chamber between about 0.0005 psi to about 0.01000 psi above ambient pressure when gas from the pressurized gas source flows into the internal chamber. In various embodiments of the incubator, the incubator may include at least one fluid drain passage in the enclosure configured to drain a fluid reservoir within the enclosure. In some embodiments, the fluid drain passageway may be sealable.

In various embodiments of the incubator, the incubator may further include a printed circuit board (PCB). In some embodiments, the PCB is located proximal to an internal surface of a top (e.g., a lid) of the enclosure. In various embodiments, the PCB includes a plurality of openings in register with the plurality of openings passing through the enclosure. For example, the PCB openings can be in register with a plurality of openings passing through a lid of the enclosure. In some embodiments, the PCB is located immediately adjacent to the sealing element of the incubator. For example, the PCB can have a substantially flat surface that directly contacts a substantially flat surface of the sealing element. In certain embodiments, the sealing element is disposed between the PCB and an internal surface of a lid of the enclosure. In various embodiments, the incubator may further include one or more sensors on the PCB. In some embodiments, each of the one or more sensors is selected from the group consisting of: a temperature sensor, a humidity sensor, an oxygen sensor, and a carbon dioxide sensor.

In various embodiments of the incubator, the incubator may further include a temperature controller configured to maintain a temperature of the internal chamber within a desired range.

In various embodiments of the incubator, the incubator may further include a first heating/cooling device engaged with or otherwise coupled with the enclosure, the first heating/cooling device controlled by the temperature controller. In some embodiments, the first heating/cooling device may be selected from the group consisting of: a resistive heater, a fluid coil configured to circulate a heat exchange fluid, and one or more Peltier devices. In some embodiments, the first heating/cooling device may directly or indirectly contact an outer surface of the bottom of the enclosure. In some embodiments, the first heating/cooling device may contact (directly or indirectly) at least about 75% of the outer surface of the bottom of the enclosure. In some embodiments, the first heating/cooling device may include a fluid coil.

In various embodiments of the incubator, the incubator may further include a second heating/cooling device engaged with or otherwise coupled with the enclosure, the first heating/cooling device controlled by the temperature controller. In some embodiments, the second heating/cooling device may be engaged with a top (e.g., a lid) of the enclosure. In some embodiments, the second heating/cooling device may be located within the enclosure. In some embodiments, the second heating/cooling device may include a plurality of openings that are in register with the plurality of openings in the enclosure. In some embodiments, the second heating/cooling device may include resistive heating elements that are part of a PCB (e.g., the PCB described above and elsewhere herein).

In some embodiments, the resistive heating elements may be located on a side of the PCB facing the internal chamber of the enclosure. In other embodiments, the resistive heating elements may be located within the PCB. For example, the PCB may comprise a multi-layer (e.g., four-layer) construction and the resistive heating elements may reside in internal layers of the PCB.

In various embodiments of the incubator, the incubator may further include a spacer having a plurality of openings. In some embodiments, the plurality of openings on the spacer may be in register with the plurality of openings of the enclosure. In some embodiments, the spacer may be located between the PCB and the sealing element. In other embodiments, the spacer may be located between the sealing element and an internal surface of a lid of the enclosure. In some embodiments, the spacer may be configured to reduce friction between the sealing element and the PCB or the internal surface of the lid of the enclosure when the sealing element moves between an open and a closed position. In some embodiments, the spacer may be configured to improve the seal formed between the sealing element and the PCB or the internal surface of the lid of the enclosure when the sealing element moves between an open and a closed position.

In various embodiments of the incubator, the incubator may further include a support for the cell culture plate. In some embodiments, the support may be configured to slideably move relative to the enclosure from a position within the enclosure to a position outside of the internal chamber of the enclosure. In some embodiments, the support may be formed by one or more internal surfaces of the enclosure.

In various embodiments of the incubator, the incubator may further include an access door attached to the support for the cell culture plate. In some embodiments, the support and access door may form an access assembly including a front plate that sealably interfaces with a portion of the enclosure. In some embodiments, the access assembly may be movably mounted on an enclosure support that supports the enclosure.

In various embodiments of the incubator, the incubator may further include tracks on the enclosure support, wherein the access assembly is configured to slide relative to the tracks on the enclosure support.

In various embodiments of the incubator, the incubator may further include an enclosure support configured to support the enclosure. In various embodiments of the incubator, the incubator may further include one or more adjustable connectors configured to connect the enclosure support to the enclosure.

In various embodiments of the incubator, the incubator may further include an insulation material coupled to the enclosure. In some embodiments, the insulation material may be attached to one or more outer surfaces of the enclosure. In various embodiments, the incubator may be configured to maintain a selected internal temperature, humidity, and gas content within the internal chamber of the enclosure. In various embodiments of the incubator, the incubator may further include a controller configured to maintain the selected internal temperature, humidity, and gas content within the internal chamber of the enclosure.

In another aspect, the invention provides a method for accessing an internal chamber of an incubator. The incubator can be any incubator described above or elsewhere herein. For example, the incubator can comprise an enclosure having a plurality of openings and a sealing element having a plurality of openings corresponding to at least a subset of the plurality of openings in the enclosure. In various embodiments, the method includes the steps of moving the sealing element to an open position to bring the plurality of openings in the sealing element into register with a first subset of openings of the plurality of openings in the enclosure, the plurality of openings in the sealing element and the first subset of the plurality of openings in the enclosure thereby providing a plurality of passages from an exterior of the incubator to the internal chamber of the enclosure; advancing an import/export tip through one or more of the plurality of passages between the exterior of the incubator and the internal chamber of the enclosure; and collecting or depositing a material within the internal chamber of the incubator using the import/export tip. In various embodiments of the method, the material may include a biological micro-object. In some embodiments of the method, collecting or depositing the material may include collecting or depositing the material within a well of a cell culture plate positioned within the internal chamber of the incubator.

In various embodiments of the method, the method may further include the steps of: withdrawing the import/export tip through one or more of the passages between the exterior of the incubator and the internal chamber of the enclosure after collecting or depositing the material; and moving the sealing element to a closed position such that the sealing element covers the plurality of openings in the enclosure.

In some embodiments of the method, the sealing element may be in the open position for an amount of time which is sufficiently short so as to prevent the carbon dioxide content and/or the humidity of the air present in the internal chamber of the enclosure from equilibrating with the carbon dioxide content and/or the humidity of the air surrounding the incubator.

In various embodiments of the method, the method may further include the step of actuating a sealing element actuator to move the sealing element to the open position or closed position. In some embodiments, moving the sealing element between the open position and the closed position may include sliding the sealing element relative to the enclosure. In various embodiments of the method, when the plurality of openings in the sealing element are in the open position, the plurality of openings in the sealing element may be configured to be in register with a plurality of wells in the cell culture plate.

In various embodiments of the method, the incubator may include a support within the internal chamber of the incubator configured to support the cell culture plate. In various embodiments of the method, the method may further include the step of sliding the support, and a cell culture plate resting on the support, from the internal chamber of the enclosure to a position outside of the internal chamber of the enclosure, thereby withdrawing the cell culture plate from the internal chamber of the enclosure. In some embodiments, sliding the support may include sliding an access assembly comprising the support for the cell culture plate and an access door attached to the support. In some embodiments, sliding the support (or access assembly) may include sliding the support (or access assembly) along one or more tracks of an enclosure support that supports the enclosure. In some embodiments, sliding the support (or access assembly) may be performed by a human operator. In other embodiments, sliding the support (or access assembly) is performed robotically.

In various embodiments of the method, the method may further include the step of sliding the support from the internal chamber of the incubator to a position outside of the internal chamber of the enclosure, thereby withdrawing the support from the enclosure. In various embodiments of the method, the method may further include the step of placing a cell culture plate on the support while the support is in the position outside of the internal chamber of enclosure. In some embodiments, placing the cell culture plate may be performed by a human operator. In other embodiments, placing the cell culture plate may be performed robotically. In various embodiments of the method, the method may further include the step of sliding the support, and the cell culture plate placed upon the support, to a position inside the internal chamber of the enclosure. In some embodiments, sliding the support may include sliding an access assembly, wherein the access assembly comprises the support for the cell culture plate and an access door attached to the support. In various embodiments of the method, the step of sliding the support comprises sliding the support or access assembly along one or more tracks of an enclosure support of the incubator. In some embodiments, sliding the support (or access assembly) may be performed by a human operator. In other embodiments, sliding the support (or access assembly) may be performed robotically.

In various embodiments, the method may further include the step of establishing an environment within the internal chamber of the enclosure suitable for supporting a biological micro-object cultured in a cell culture plate positioned within the internal chamber of the enclosure. In various embodiments, the method may further include the step of measuring one or more of a temperature, a humidity, and a carbon dioxide content of the internal chamber of the incubator. In various embodiments, the method may further include the step of controlling one or more of a temperature, a humidity, and a carbon dioxide content of the internal chamber of the incubator. In some embodiments, controlling the temperature may include heating or cooling the internal chamber of the incubator. In some embodiments, controlling the humidity may include providing a humidity source to the internal chamber of the incubator. In some embodiments, controlling the carbon dioxide content may include providing a gas source including carbon dioxide (e.g., a known percentage of carbon dioxide) to the internal chamber of the incubator. In some embodiments, the gas source comprising carbon dioxide may further include oxygen and nitrogen. In some embodiments, providing a gas source including carbon dioxide may include providing a purge gas to the internal chamber.

In various embodiments, collecting or depositing the material is performed with the import/export tip. In some embodiments, the import/export tip comprises a plurality of tips, allowing substantially simultaneous collection of material from a plurality of wells of a cell culture plate or substantially simultaneous deposition of material into a plurality of wells of the cell culture plate. Thus, in various embodiments, the method may further include the step simultaneously collecting or depositing material from/into a plurality of wells in a cell culture plate. In some embodiments, the collecting or depositing may be performed robotically.

In some embodiments, the sealing element, when in the closed position, is capable of maintaining a pressure within the internal chamber that is greater than the ambient air pressure. For example, the pressure within the internal chamber of the enclosure can be between about 0.0005 psi to about 0.0100 psi above ambient pressure. Thus, in various embodiments, the method may further include the step of maintaining a pressure within the internal chamber of the enclosure at a pressure greater than a pressure outside of the incubator when the sealing element is in a closed position. In other embodiments, the method may further include the step of maintaining a pressure within the internal chamber of the enclosure at a pressure greater than a pressure outside of the incubator when the sealing element is in an open position. In some embodiments, maintaining a pressure within the internal chamber when the sealing element is in an open position can include providing a purge gas to the internal chamber.

In some embodiments, each of the plurality of openings in the enclosure may have a diameter of about 1 mm to about 10 mm. In other embodiments, each of the plurality of openings in the enclosure has a diameter of about 1 mm to about 5 mm, or about 1.0 mm, about 1.5 mm, about 2.0 mm, about 2.5 mm, about 3.0 mm, about 3.5 mm, about 4.0 mm, about 4.5 mm, about 5.0 mm, or any range defined by the foregoing values. In some embodiments, each of the plurality of openings in the sealing element may have a diameter of about 1 mm to about 10 mm. In some embodiments, each of the plurality of openings in the sealing element may have a diameter of about 1 mm to about 5 mm, or about 1.0 mm, about 1.5 mm, about 2.0 mm, about 2.5 mm, about 3.0 mm, about 3.5 mm, about 4.0 mm, about 4.5 mm, about 5.0 mm, or any range defined by the foregoing values.

In yet another aspect of the invention, a method is provided for accessing an internal chamber of an incubator, where the incubator comprises an enclosure having a plurality of openings and a sealing element having more than one plurality of openings, wherein each plurality of openings in the sealing element corresponds to at least a subset of the plurality of openings in the enclosure.

In various embodiments, the method includes the steps of: moving the sealing element to a first open position, thereby bringing a first plurality of openings in the sealing element into register with a first subset of the plurality of openings in the enclosure, where the first plurality of openings in the sealing element and the first subset of the plurality of openings in the enclosure provide a first plurality of passages from an exterior of the incubator to the internal chamber of the enclosure; advancing an import/export tip through one or more of the first plurality of passages between the exterior of the incubator and the internal chamber of the enclosure; and collecting or depositing a material the internal chamber of the incubator using the import/export tip. When the sealing element is in the first open position, any openings of the plurality of openings in the enclosure that are not in the first subset of openings can be occluded by the sealing element. In various embodiments, the first plurality of passages may be configured to be in register with a first subset of wells in a cell culture plate positioned within the internal chamber of the enclosure.

In various embodiments of the method, the method may further include the step of moving the sealing element to a second open position, thereby bringing a second plurality of openings in the sealing element into register with a second subset of the plurality of openings in the enclosure, the second plurality of openings in the sealing element and the second subset of the plurality of openings in the enclosure providing a second plurality of passages from an exterior of the incubator to the internal chamber. In some embodiments, the first plurality of openings in the sealing element can be identical to the second plurality of openings in the sealing element. In other embodiments, the first plurality of openings in the sealing element can be different from the second plurality of openings in the sealing element (e.g., the first and second pluralities of openings in the sealing element can be completely non-overlapping or partially over-lapping). When the sealing element is in the second open position, any openings of the plurality of openings in the enclosure that are not in the second subset of openings can be occluded by the sealing element. In various embodiments, the second plurality of passages may be configured to be in register with a second subset of wells in a cell culture plate positioned within the internal chamber of the enclosure.

In various embodiments of the method, the method may further include the step of moving the sealing element to a third open position, thereby bringing a third plurality of openings in the sealing element into register with a third subset of the plurality of openings in the enclosure, the third plurality of openings in the sealing element and the third subset of the plurality of openings in the enclosure providing a third plurality of passages from an exterior of the incubator to the internal chamber of the enclosure. In some embodiments, the third plurality of openings in the sealing element can be identical to the first and/or second pluralities of openings in the sealing element. In other embodiments, the third plurality of openings in the sealing element can be different from the first and/or second plurality of openings in the sealing element (e.g., the first, second, and third pluralities of openings in the sealing element can be completely non-overlapping or partially over-lapping). When the sealing element is in the third open position, any openings of the plurality of openings in the enclosure that are not in the third subset of openings can be occluded by the sealing element. In various embodiments, the third plurality of passages may be configured to be in register with a third subset of wells in a cell culture plate positioned within the internal chamber of the enclosure.

In some embodiments, the number of passages in the first plurality of passages may be the same as the number of wells in the cell culture plate. In some embodiments, the number of passages in each of the first, second, and/or third plurality of passages may be equal to or less than one-half, one-third, one-fourth, one-sixth, or one-twelfth the number of wells in the cell culture plate.

In various embodiments of the method, the method may further include the step of moving the sealing element to a closed position, thereby bringing each of the plurality of the openings in the enclosure to an occluded position.

In another aspect of the invention, an incubation system is provided. The incubation system can include: a well plate incubator, such as described above or elsewhere herein; a robotic sampling component configured to access the well plate incubator to remove/deliver samples; and at least one controller configured to open a plurality of passages in the incubator and to control the robotic sampling component to access, via the plurality of passages, a plurality of wells of a well plate contained within the well plate incubator. In various embodiments, the wells of the well plate may contain a biological material, including a biological micro-object (e.g., a cell).

In some embodiments, the at least one controller may be further configured to close the plurality of passages. In some embodiments, the system may be configured to maintain the well plate incubator under positive pressure. In some embodiments, the at least one controller may be configured to control the robotic sampling component to withdraw a material from one of the plurality of wells of the well plate. In some embodiments, the at least one controller may be configured to control the robotic sample component to deliver the withdrawn material to a microfluidic device. In some embodiments, the at least one controller may be configured to control the robotic sample component to deliver the withdrawn material to an analytical instrument. In some embodiments, the at least one controller may be configured to control the robotic sample component to deliver one or more materials to one or more wells of the well plate contained within the well plate incubator. In some embodiments, the one or more materials may be obtained from a microfluidic device. In other embodiments, the one or more materials may be obtained from an analytical instrument.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 2A-2C illustrate a top view of a lid, a printed circuit board and its associated connector, and an optional spacer, of an incubator, respectively, in accordance with some embodiments.

FIGS. 5A-5B illustrate a lid having flexible tabs that can be part of the enclosures described herein. FIG. 5A illustrates a top surface of the lid, while FIG. 5B shows a view of the bottom surface of the lid.

FIG. 5H illustrates a top view of a portion of an incubator having the lid and the sealing element removed and including a printed circuit board, in accordance with some embodiments.

FIG. 10C illustrates a top view of an enclosure support, in accordance with some embodiments.

DETAILED DESCRIPTION

Figure 1A:
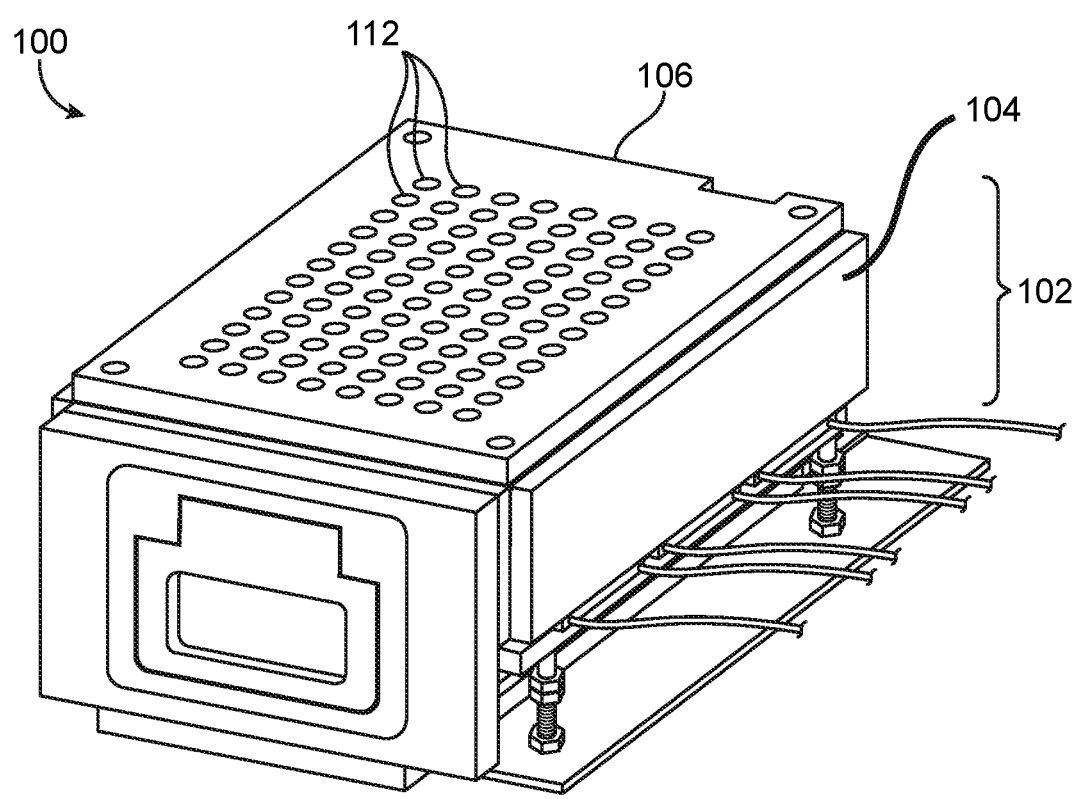
FIGS. 1A-1B illustrate an isometric view and an exploded isometric view of an incubator, respectively, in accordance with some embodiments.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

As used herein, the term "micro-object" can encompass one or more of the following: inanimate micro-objects such as microparticles; microbeads (e.g., polystyrene beads, Luminex™ beads, or the like); magnetic beads; microrods; microwires; quantum dots, and the like; biological micro-objects such as cells (e.g., embryos, oocytes, sperm cells, cells dissociated from a tissue, eukaryotic cells, protist cells, animal cells, mammalian cells, human cells, immunological cells, hybridomas, cultured cells, cells from a cell line, cancer cells, infected cells, transfected and/or transformed cells, reporter cells, prokaryotic cell, and the like); biological organelles; vesicles, or complexes; synthetic vesicles; liposomes (e.g., synthetic or derived from membrane preparations); lipid nanorafts (as described in Ritchie et al. (2009) "Reconstitution of Membrane Proteins in Phospholipid Bilayer Nanodiscs," Methods Enzymol., 464:211-231), and the like; or a combination of inanimate micro-objects and biological micro-objects (e.g., microbeads attached to cells, liposome-coated micro-beads, liposome-coated magnetic beads, or the like). Beads may further have other moieties/molecules covalently or non-covalently attached, such as fluorescent labels, proteins, small molecule signaling moieties, antigens, or chemical/biological species capable of use in an assay.

As used herein, the term "cell" refers to a biological cell, which can be a plant cell, an animal cell (e.g., a mammalian cell), a bacterial cell, a fungal cell, or the like. A mammalian cell can be, for example, from a human, a mouse, a rat, a horse, a goat, a sheep, a cow, a primate, or the like.

As used herein, the term "maintaining (a) cell(s)" refers to providing an environment comprising both fluidic and gaseous components that provide the conditions necessary to keep the cells viable and/or expanding.

As used herein, the term "expanding" when referring to cells, refers to increasing in cell number.

As used herein, "import/export tip" refers to a mechanical delivery device sized to fit within one or more wells of a cell culture plate and deposit/withdraw material and/or media. The import/export tip can comprise, for example, a needle, a pin, or a similar structure having a surface capable of adhering to material and/or media located within or intended for the cell culture plate. The import/export tip can further comprise, for example, a hollow delivery tube having an internal diameter sufficiently large to permit passage of material and/or media located within or intended for the cell culture plate. In some embodiments, the import/export tip may be made from a metal or ceramic material. In some embodiments, the import/export tip may be made from a polymer (e.g., plastic). For example, the import/export tip can comprise plastic tubing, which may or may not be stiffened with an exterior sleeve. In other embodiments, the import/export tip may be a cannula or needle. An import/export tip may be any type of material that is compatible with the material being transferred. The import/export tip may be suitable for autoclaving or it may be disposable.

As used herein, a "microfluidic device" is a device that includes one or more discrete microfluidic circuits configured to hold a fluid, each circuit comprised of interconnected circuit elements, including but not limited to region(s), chamber(s), channel(s), and/or pen(s), and at least two ports configured to allow the fluid (and, optionally, micro-objects suspended in the fluid) to flow into and/or out of the microfluidic device. Typically, a microfluidic circuit of a microfluidic device will hold a volume of fluid of less than about 1 mL, e.g., less than about 750, 500, 250, 200, 150, 100, 75, 50, 25, 20, 15, 10, 9, 8, 7, 6, or 5 µL (or about 2-5, 2-10, 2-15, 2-20, 5-20, 5-30, 5-40, 5-50, 10-50, 10-75, 10-100, 20-100, 20-150, 20-200, 50-200, 50-250, or 50-300 µL).

As used herein, a "nanofluidic device" is a type of microfluidic device having a microfluidic circuit that contains at least one circuit element configured to hold a volume of fluid of less than about 1 µL, e.g., less than about 750, 500, 250, 200, 150, 100, 75, 50, 25, 20, 15, 10, 9, 8, 7, 6, 5, 4, 3, 2, 1 nL or less (or about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL).

As used here, reference numbers in the detailed description of the invention refer not only to a specific embodiment, but are used for clarity and ease of review for the entire scope of the inventive matter. Specific embodiments of each element are shown in the figures and use the same reference number, but such use is in no ways intended to limit the breadth of the inventive matter to single embodiments.

Incubators and methods of using incubators are disclosed herein that improve accessibility to a cell culture plate in an internal chamber within an enclosure of the incubator, while also minimizing the chance of contamination of the internal chamber of the incubator. The incubators described herein can be more easily accessed by a robotic arm or other tool, such as an import/export tip or other sampling device than conventional incubators that require opening a swinging lid or door in order to access the internal chamber of the incubator. The lack of a swinging lid or door that exposes the internal chamber of the incubator to the external environment can greatly decrease the chance of contamination of the incubator.

An incubator can include an enclosure having an internal chamber configured to support a cell culture plate having a plurality of wells. The enclosure can include a plurality of openings configured to allow access to the wells. The incubator can include a sealing element configured to seal the plurality of openings in the enclosure. The sealing element can include a first plurality of openings corresponding to at least a subset of the plurality of openings in the enclosure Enclosure. An incubator 100 includes an enclosure 102. The enclosure 102 can include a base 104 and a lid 106, 206 (see one exemplar in FIGS. 1A-1B and other exemplars in FIGS. 16 and 5C-5E). The base 104 and the lid 106, 206 can define the internal chamber 110 of the incubator 100. In some embodiments, the base 104, lid 106, 206, and a front plate 156 can define the internal chamber 110 of the incubator 100. In some embodiments the base 104 can be formed from a rigid material having a high thermal conductivity and low thermal capacitance. Some suitable materials can include aluminum, brass, ceramics or other copper-containing alloys. Copper-containing alloys can be particularly useful due to antimicrobial properties conferred by the copper content.

Figure 7:
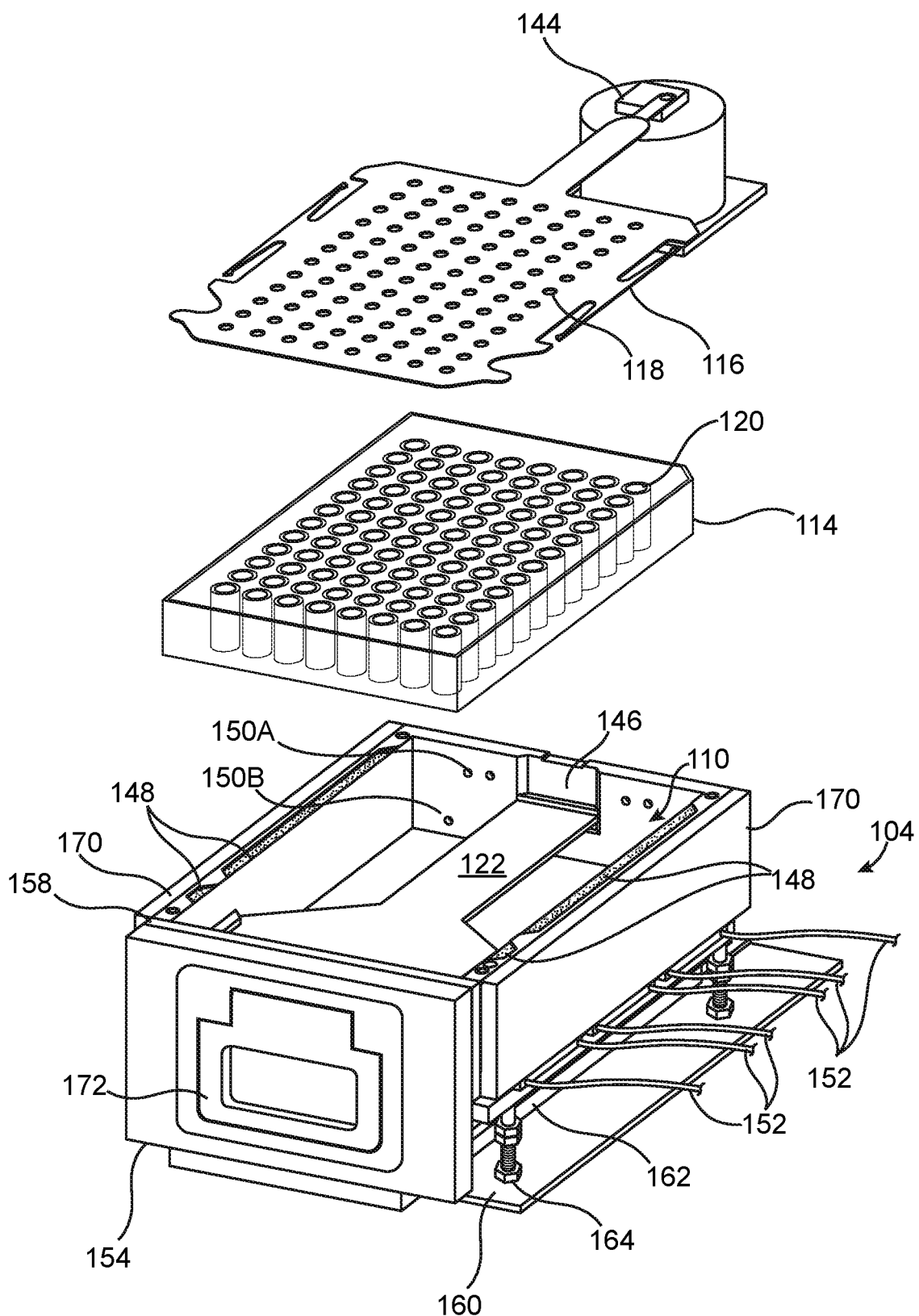
FIG. 7 illustrates an exploded isometric view of a portion of an incubator in accordance with some embodiments.
Figure 8:
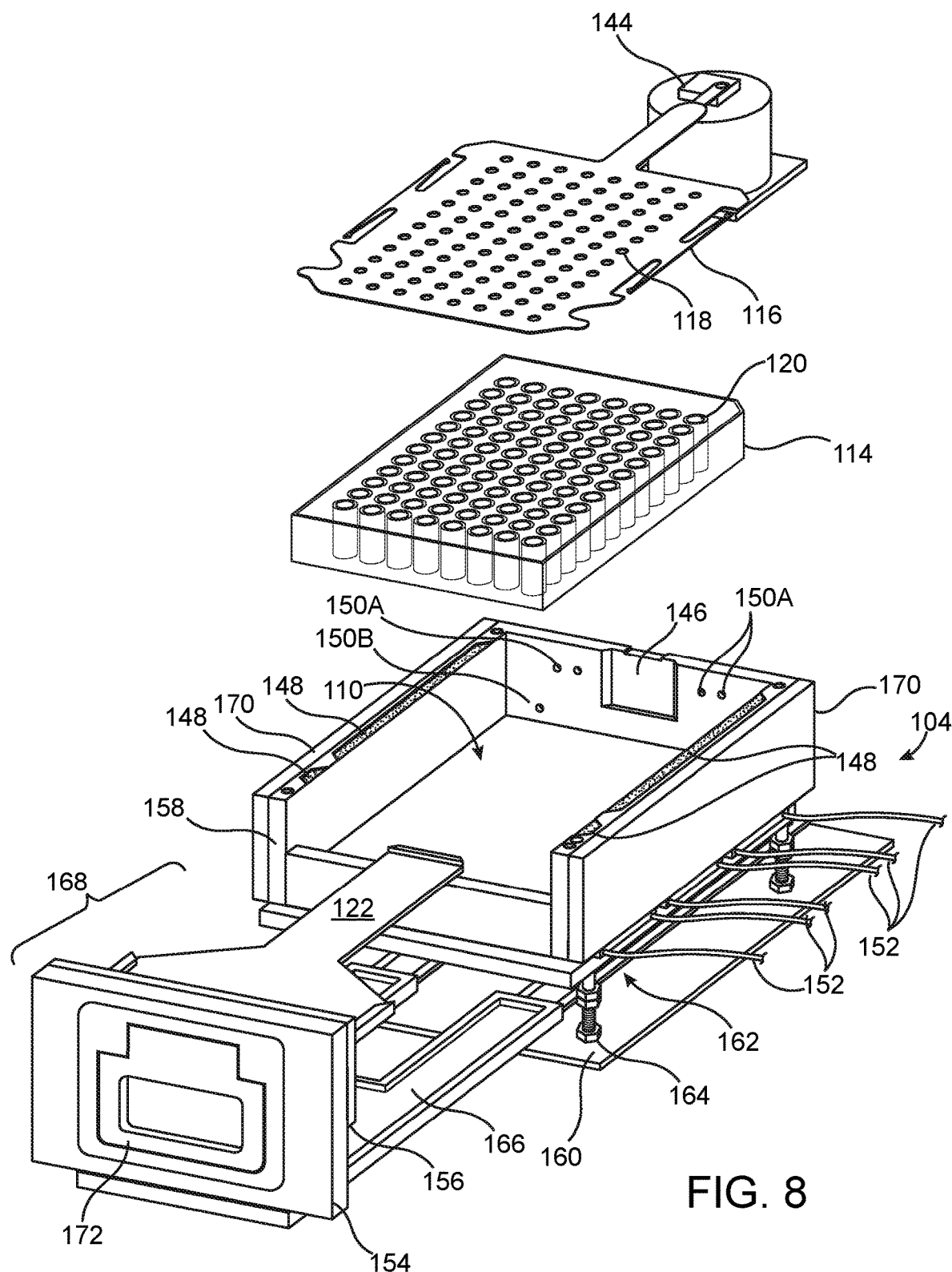
FIG. 8 illustrates an exploded isometric view of a portion of an incubator in accordance with some embodiments.

The incubator 100 can further include an insulation material coupled to the enclosure (See, for example, insulating panels 170 in FIGS. 7-8). The insulation material can be attached to one or more outer surfaces of the enclosure. A variety of plastics may be used to form insulating panels which may be coupled detachably or permanently to the exterior walls of the base 104 or may be fabricated for use as the lid. For example, one class of suitable insulating plastic may be amorphous thermoplastic polyetherimide, which is available in a wide range of formulations, and is available commercially as ULTEM™ (SABIC). The insulating panels may be formed to incorporate one or more recesses, where the recess includes air further insulating the enclosure. In some embodiments, the insulating panel may be about 1 mm, 2 mm, 3 mm, 4 mm, 5 mm, 6 mm, 7 mm, 8 mmm, 9 mm, or about 10 mm thick. The insulating panels may be fabricated to create a recess between an outer surface of the panel and the outer surface of the enclosure to which it is attached. For example, the insulating panels attached to the base 104 of the enclosure 102, may be fabricated to hollow out its inner surface, disposing the inner surface of the insulation panel about 1 mm, 2 mm, 3 mm, 4 mm, 5 mm, 6 mm, 7 mm, 8 mm, 9 mm, 10 mm, or about 11 mm away from the outer surface of the base 102, except where the panel 170 is attached to the base 104. This may create a pocket of air that is about 1 mm, 2 mm, 3 mm, 4 mm, 5 mm, 6 mm, 7 mm, 8 mm, 9 mm, 10 mm, or about 11 mm thick at the sides of the base 104. The insulating panels may be suitable for autoclaving or may be removed from the enclosure prior to autoclaving.

Lid. The lid 106, 206 can include an outer surface exterior to the enclosure 102 and an inner surface within the enclosure 102 (See one exemplar in FIGS. 1A-1B and another exemplar in FIG. 16). The lid 106, 206 may be part of a lid assembly 108 (See one exemplar in FIGS. 3A-C). The inner surface of the lid 106, 206 can include one or more recesses 124. The recesses 124 in the lid 106, 206 can be configured to accommodate parts of the lid assembly 108, such as a printed circuit board (PCB) 132, 232 and/or a spacer 134, each of which is described in additional detail below. In some cases, the recesses 124 can be configured to channel gas flow and/or provide insulation. In some embodiments the inner surface can include one or more recesses that can substantially surround groups 213 of openings 212 (See one exemplar in FIG. 5B). Each group 213 can include two or more (e.g., 3, 4, 6, etc.) openings 212 of the plurality of openings 212. The groups 213 of the openings 212 can improve a seal formed between the lid 206 and the sealing element 116, 216 when the sealing element 116, 216 is in the closed position. For example, the openings 118, 218 in the sealing element 116, 216 can be occluded by the space between the openings 212 of the groups 213. The openings 212 to the left side of the groups 213 can form a first subset of openings while the openings 212 to the right side of the groups 213 can form a second subset of openings. In some embodiments the recesses of the lid 106, 206 can be sealed with a sealing material and/or insulating material. The sealing material can be configured to prevent air within the enclosure from filling the one or more recesses. Thus, the lid 106, 206 can include a plurality of pockets filled with a gas or substantially lacking a gas (e.g., the pockets could include a vacuum or sub-atmospheric pressure). In some embodiments, the sealing material can include an adhesive layer adhered to the inner surface of the lid 106, 206. The adhesive layer can include insulating materials. In some embodiments, the lid 106, 206 is made from a rigid insulating material such as a polymer or plastic. In other embodiments, the lid 106, 206 is made from a rigid material having a high thermal conductivity and low thermal capacitance (e.g., aluminum, copper, brass, other copper-containing alloys, or ceramics). One suitable class of plastic that the lid may be made from is polyetherimide (e.g., ULTEM™), as described above. The lid may be made from a material that can be autoclaved after use.

The lid 106, 206 can include one or more connectors configured to sealably connect the lid 106 to the base 104. Examples of the one or more connectors include a magnet, a flexible tab, a flexible clip, or similar structures. In one example the lid includes flexible tabs 215 that can be configured to engage with a pin 215b to secure the lid 206 to the base (See one exemplar in FIGS. 5C-5E). The seal between the base 104 and the lid 106 does not have to be air-tight.

In some embodiments the lid can include an outer surface 207 (See one exemplar in FIG. 5A) that includes a marking 207a of an instruction such as "pull up to remove". The lid 206 can also include instructions 215c on the compression tabs 215, such as "push to install". The marking 207a and instructions 215c can colored, etched, or adapted to be machine readable by a computer imaging program.

The lid 106 and associated lid assembly 108 can include the plurality of openings 112 in the enclosure 102 providing access to the wells 120 of the cell culture plate 114.

Lid assembly. The lid assembly 108 of the incubator 100 can include a printed circuit board (PCB) 132, 232 (See various exemplars in FIGS. 3B, 3F, 4B and 5H). The PCB 132 can be part of or coupled to the lid 106 of the incubator 100. In another example, the PCB 132 can be positioned between the enclosure and the sealing element 216. For example, the PCB 132 can be located between the sealing element 116 and an internal surface of a top of the enclosure 102, such as the lid 106. Alternatively, the PCB 232 can be positioned proximal to (e.g., adjacent to) a top of the enclosure 102 (e.g., the lid 206), with the sealing element interspersed between the PCB 232 and the top of the enclosure 102 (See an exemplar in FIGS. 3E-F). The PCB 132, 232 can have a substantially flat surface that directly contacts a substantially flat surface of the sealing element 116, 216 and/or a spacer 134. The PCB 132, 232 can include a plurality of openings 138, 238 in register with the plurality of openings 112, 212 of the lid 106, 206 to provide the openings of the enclosure 102. In some embodiments the PCB 132, 232 includes one or more sensors on the PCB 132, 232. The one or more sensors can be selected from the group consisting of: a temperature sensor, a humidity sensor, an oxygen sensor, and a carbon dioxide sensor. In yet other embodiments, the PCB 132, 232 may include resistive heating elements, as described in more detail below. The resistive heating elements can be located on a side of the PCB 132, 232 facing the internal chamber 110 of the enclosure 102 and/or the cell culture plate 114. Alternatively, the resistive heating elements can be located internally in the PCB 132, 232. The PCB 132, 232 can include a multi-layer construction. The multi-layer construction can include the resistive heating elements internally such that the resistive heating elements are not exposed to the incubator environment external to the PCB 132, 232. The multi-layer construction of the PCB 132, 232 can improve the stiffness of the PCB 132, 232 and subsequently improve the seal between the sealing element 116, 2116 and the PCB 132, 232. When one or more sensors and/or resistive heating elements are included in the PCB 132, 232, each of these elements are located such that each element does not interfere with the openings 138, 238 in the PCB 132, 232. In some embodiments, the lid assembly 108 can be removable from the incubator. In some embodiments, the PCB may be designed to be disposable after each use. The PCB 132, 232 may be connected to a controller 174 (see one exemplar in FIG. 17) and/or other components via a connector 136.

Figure 3A:
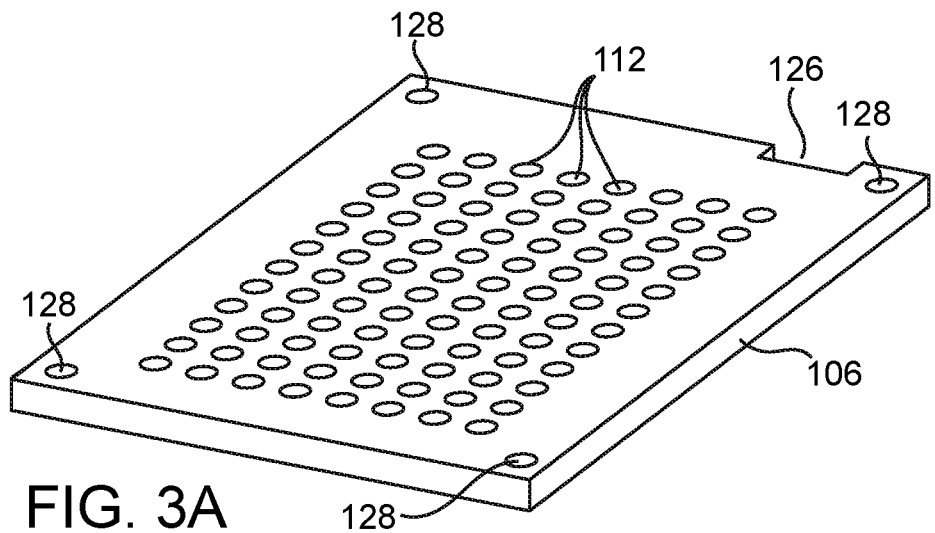
FIGS. 3A-3C illustrate an exploded isometric view showing the top surface of a lid, a printed circuit board and its associated connector, and a spacer, respectively, that can be used in the embodiments of incubators described herein.
Figure 3B:
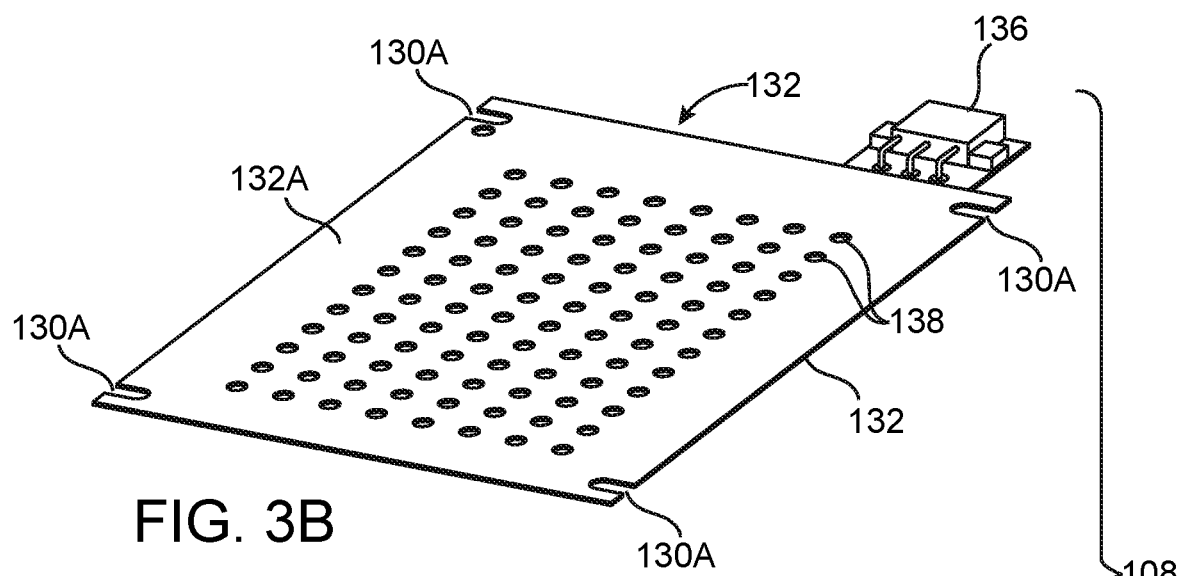
Figure 3C:
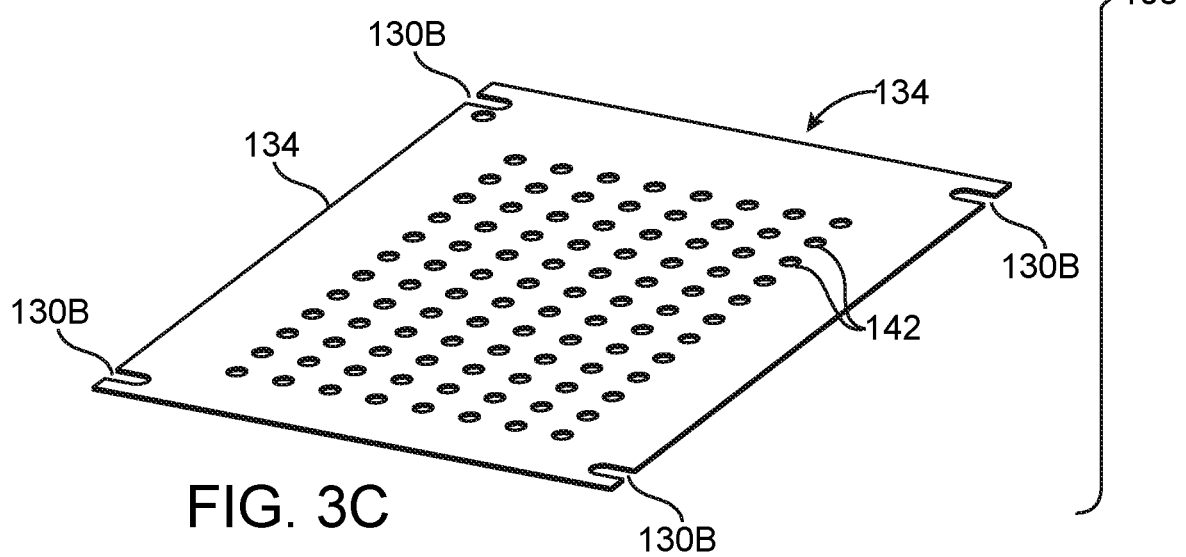

In some embodiments, the incubator 100 may include a spacer 134 as part of the lid assembly 108 (some exemplary embodiments are shown in FIGS. 2C and 3C). The spacer 134 can be configured to reduce friction between the sealing element 116, 216 and the PCB 132, 232 when the sealing element 116, 216 moves between an open and a closed position. The spacer 134 can have a plurality of openings 142. The plurality of openings 142 on the spacer 134 can be in register with the plurality of openings 112, 212 of the lid 106, 206 providing the openings of the enclosure 102. The plurality of openings 142 on the spacer 134 can be in register with the plurality of openings 138, 238 on the PCB 132, 232. In various embodiments, the plurality of openings 142 on the spacer 134 are in register with the plurality of openings 112, 212 of the lid 106, 206 and in register with the plurality of openings 138, 238 on the PCB 132, 232. The spacer 134 can be located between the PCB 132, 232 and the sealing element 116, 216. The spacer 134 may be configured to engage with the sealing element 116, 216, as the sealing element 116, 216 is moved between a closed position to any possible open positions. The spacer 134 may be made of a compressible material such as rubber, silicone, or other polymeric materials which can reduce friction between the sealing element 116, 216 and the PCB 132, 232. In some embodiments the spacer 134 may be detachably assembled so that it may be autoclaved between uses. In other embodiments, the spacer 134 may be disposable after each use.

In some embodiments the spacer 134 is omitted from the lid assembly 108. In some embodiments, an outer surface of the PCB 132, 232 can be coated with Parylene™ by vapor deposition, which can protect the PCB from abrasions caused by movement of the sealing element. Other types of coatings can be used on the PCB, such as urethane-based coatings and other chemicals, materials, and polymers that reduce friction between the sealing element 116, 216 and the PCB 132, 232.

Openings in the enclosure. The number of openings in the enclosure 102, provided by the openings 112, 212 in the lid 106, 206 (some exemplary embodiments are shown in FIGS. 1A-1B and FIGS. 5A-E) and openings (138, and optionally 142) of the associated lid assembly 108 (which may include the PCB 132, 232 and, optionally, spacer 134) may be the same as the number of the wells 120 in the cell culture plate 114. The openings (112, 212, 138, 238, 142) of the lid 106, 206, PCB 132, 232, and optional spacer 134 may be in register with the wells 120 in the cell culture plate 114 within the enclosure 102. In some other embodiments, the number of openings in the enclosure 102 may be different from the number of wells 120 in the cell culture plate 114. This may be used when more than one type of cell culture plate 114 is used in the incubator 100 and changing the enclosure 102 element to have fewer openings is not desired by the operator.

In some embodiments, the enclosure 102 may have 96 openings. In other embodiments, the enclosure 102 may have 384 openings. In some embodiments, the number of openings may be less than 96 or may be more or less than 384. In some embodiments, the enclosure 102 may have 24 or fewer (e.g., 12 or 6) opening. In other embodiments, the enclosure 102 may have 6 or fewer openings.

Figure 10A:
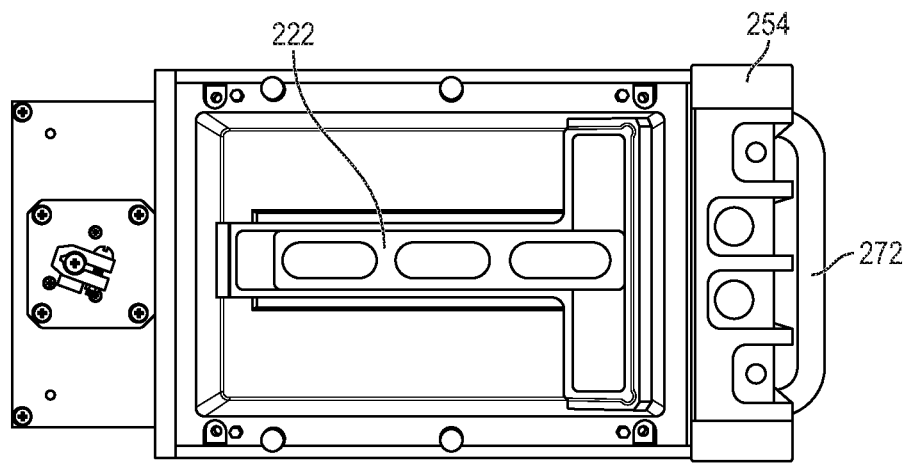
FIGS. 10A-10B illustrate a top view of a portion of an incubator, with a support for a cell culture plate in an open and a closed position, respectively, in accordance with some embodiments.
Figure 17A:
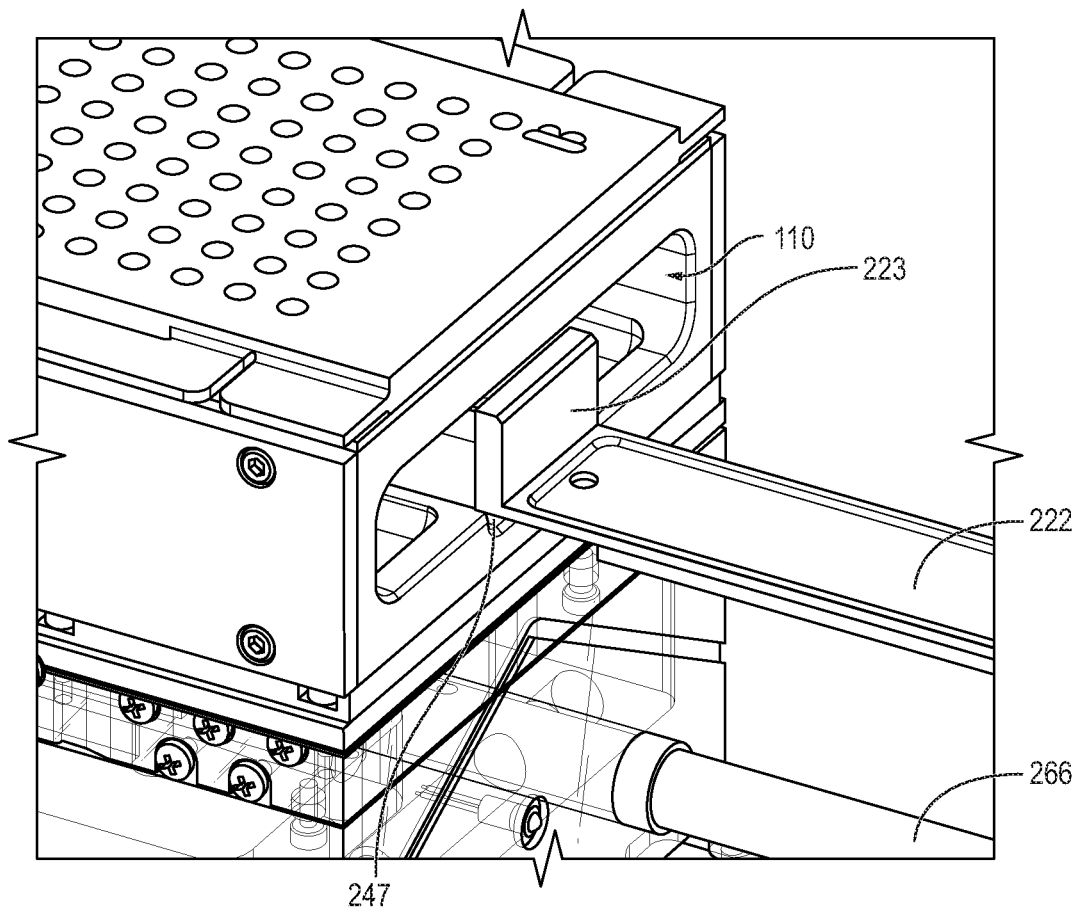
FIGS. 17A-17B illustrate an isometric view of an incubator with a support for a cell culture plate in an open and a closed position, respectively, in accordance with some embodiments.

Base. The base 104 can be configured with a hollow region forming part or all of the internal chamber 110 of the enclosure 102 (one exemplar shown in FIG. 1B and other exemplars are shown in FIGS. 10A and 17A). The base 104 can include a bottom and four walls. The four walls can define the hollow region forming part or all of the internal chamber 110 of the enclosure 102. In some embodiments one of the four walls can have a height that is shorter than the height of the other three walls. In some embodiments, the height of three of the four walls are the same. The base 104 may be made of a rigid material having a high thermal conductivity and low thermal capacitance, and be any of the suitable materials described above. In one embodiment, the base 104 is made from brass or another copper-containing alloy. The base 104 may have insulation panels attached, as described above, and may be autoclaved either while assembled or upon partial or complete disassembly.

In some embodiments the base 104 and the lid 106 are formed of the same material. In other embodiments, the base 104 and lid 106 are formed from different materials.

Figure 5A:
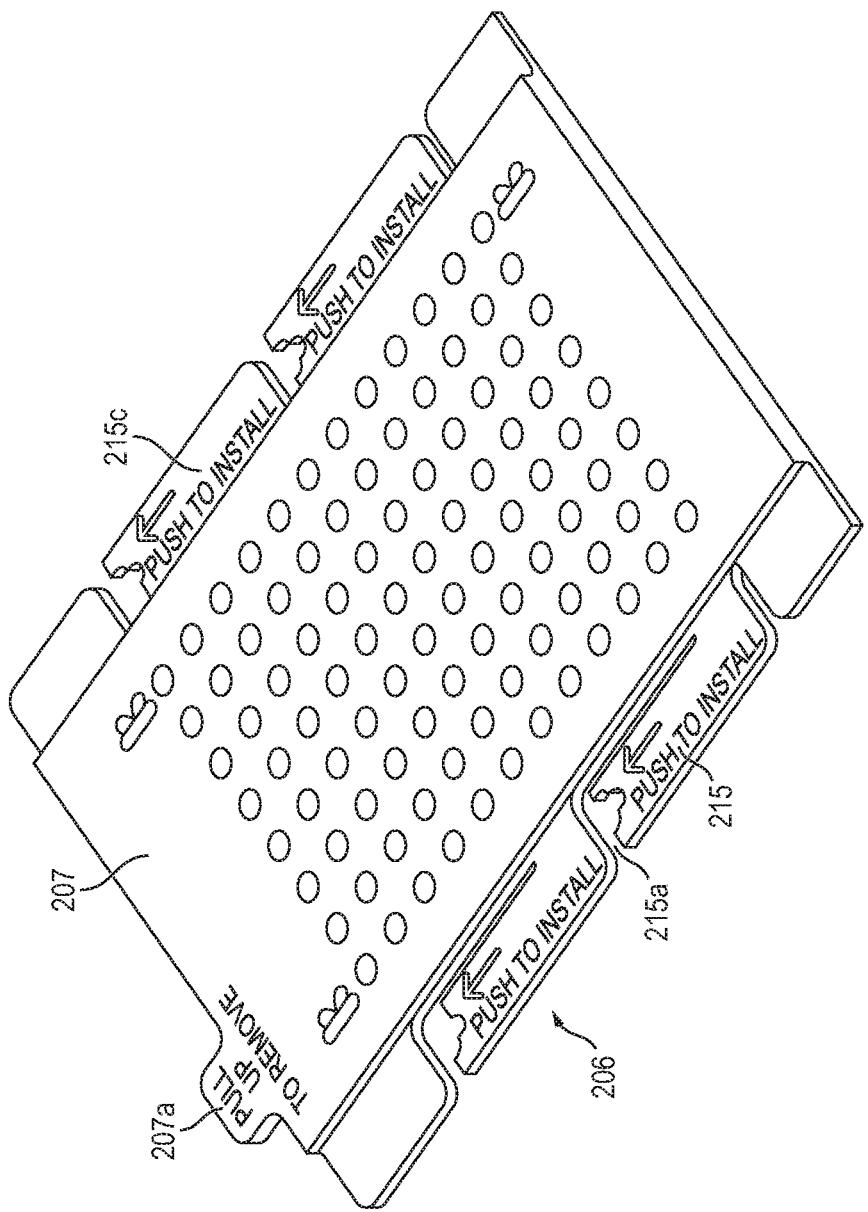

Sealing Element. The incubators 100 described herein include a sealing element 116 (one exemplar is shown in FIG. 1B) and sealing element 216 (one exemplar is shown in FIGS. 5F-5G). The sealing element 116, 216 can be located inside the internal chamber 110 of the enclosure 102. For example, the sealing element 116, 216 can be configured to be located between the cell culture plate 114 and the lid 106, 206 of the incubator 100. The sealing element 116, 216 can be configured to block the openings 112, 212 in the lid 106, 206 of the incubator 100 which provide access to wells 120 of a cell culture plate 114 inside the enclosure 102. For example, the sealing element 116, 216 can be configured to block, occlude, or obstruct a plurality of pathways between wells 120 in the cell culture plate 114 and the openings 112, 212 in the lid 106, 206. The sealing element 116, 216 can include one or more pluralities of openings 118, 218 which may each correspond to a portion or all of the plurality of openings in the enclosure 102. Access to the internal chamber 110 of the enclosure 102 and a cell culture plate 114 within, if present, may be provided by positioning the sealing element 116, 216 such that one or more of the plurality of openings (112, 212, 138, 238, and optionally 142) in the enclosure 102 is in register with one or more openings 118, 218 in the sealing element 116, 216.

The sealing element 116, 216 can be made of a wide variety of materials, including metals or plastic. Examples of suitable metals and plastics include aluminum, brass, and polymers such as ULTEM, PEEK, Teflon, etc. The use of a metal sealing element can improve heat transfer and reduce the likelihood of condensation forming or collecting on the sealing element. In some embodiments, the sealing element 116, 216 is made of aluminum or brass, an inexpensive alternative which allows the sealing element 116, 216 to be disposable or suitable for autoclaving. In other embodiments, a plastic material may be used, which also permits disposability or tolerance to autoclaving.

The sealing element 116, 216 can be movable between a closed position in which the sealing element 116, 216 covers the plurality of openings (112, 212, 138, 238, and optionally 142) in the enclosure 102, and an open position in which the plurality of openings 118, 218 of the sealing element 116, 216 are in register with at least a portion of the plurality of openings (112, 212, 138, 238, and optionally 142) in the enclosure 102. The plurality of openings 118, 218 in the sealing element 116, 216 can be configured to be in register with the plurality of wells 120 in the cell culture plate 114 within the enclosure 102.

In some embodiments, a first plurality of openings 118, 218 in the sealing element 116, 216 can be the same number as the plurality of the openings (112, 212, 138, 238, and optionally 142) in the enclosure 102. In other embodiments, a first plurality of openings 118, 218 in the sealing element 116, 216 can be a number less than the plurality of the openings (112, 212, 138, 238, and optionally 142) in the enclosure 102. In some embodiments, the number of openings in the first plurality of openings in the sealing element 116, 216 is one-half, one-third, one-fourth, one-sixth, one-twelfth, or fewer the number of openings (112, 212, 138, 238, and optionally 142) in the enclosure 102.

Figure 5E:
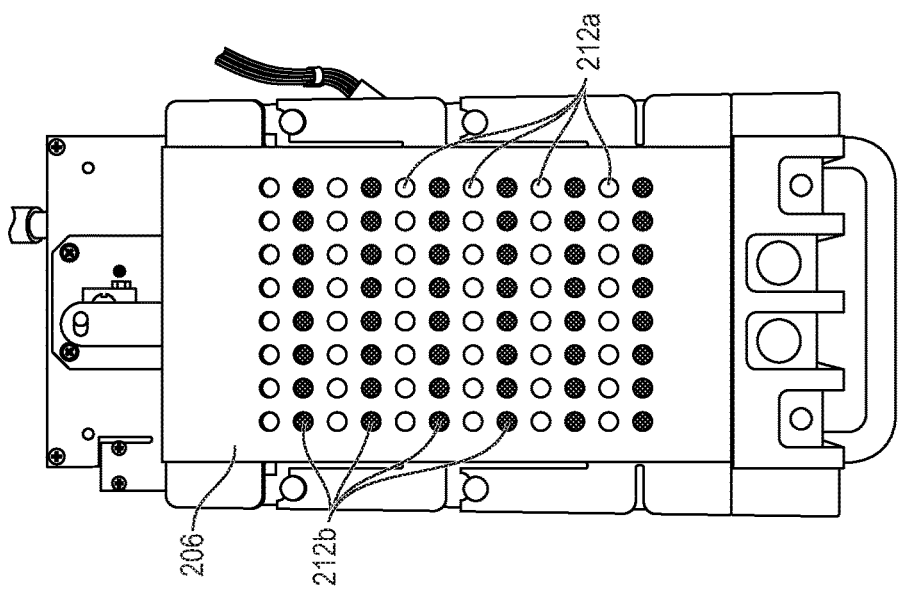
FIGS. 5C-5E illustrate a top view of an incubator having the sealing element in a closed position, a first open position, and a second open position, respectively, in accordance with some embodiments.
Figure 5D:
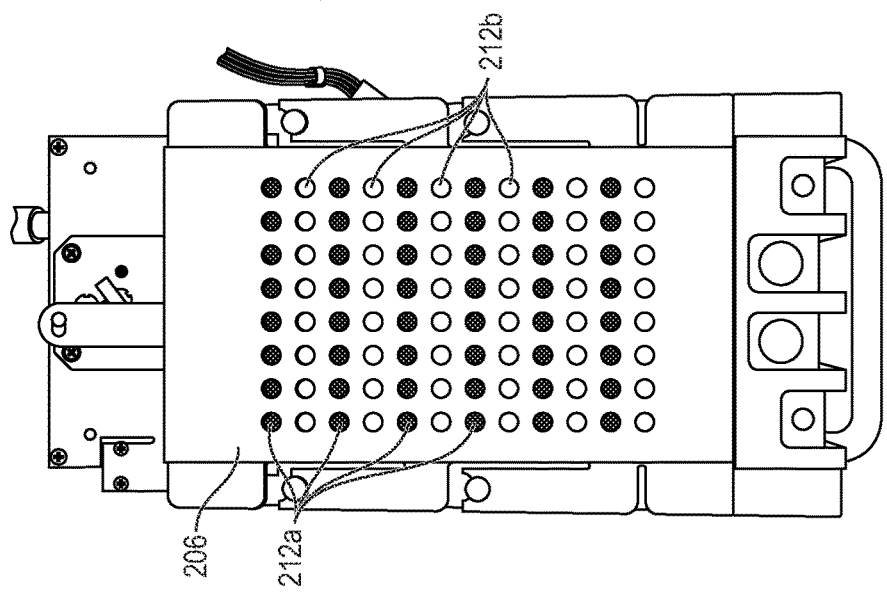
Figure 5C:
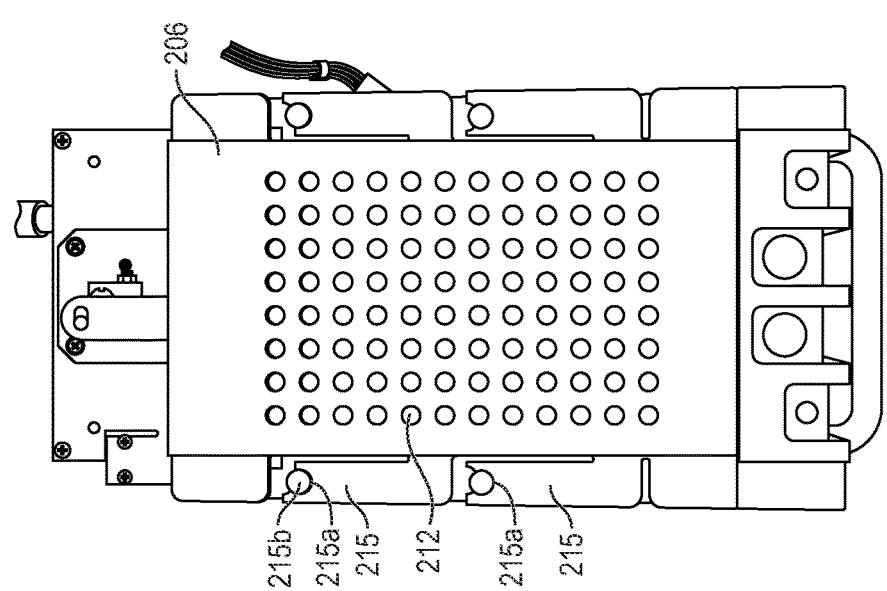
Figure 5F:
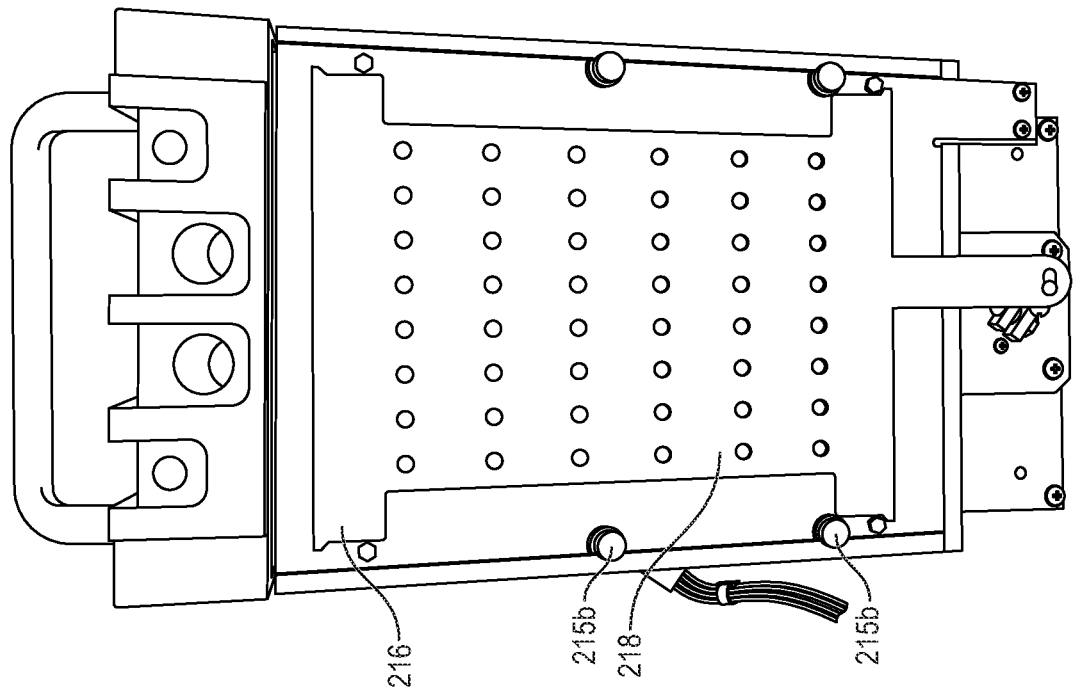
FIGS. 5F-5G illustrate a top view of a portion of an incubator having the lid removed, with the sealing element in a closed position and an open position, respectively, in accordance with some embodiments.
Figure 5G:
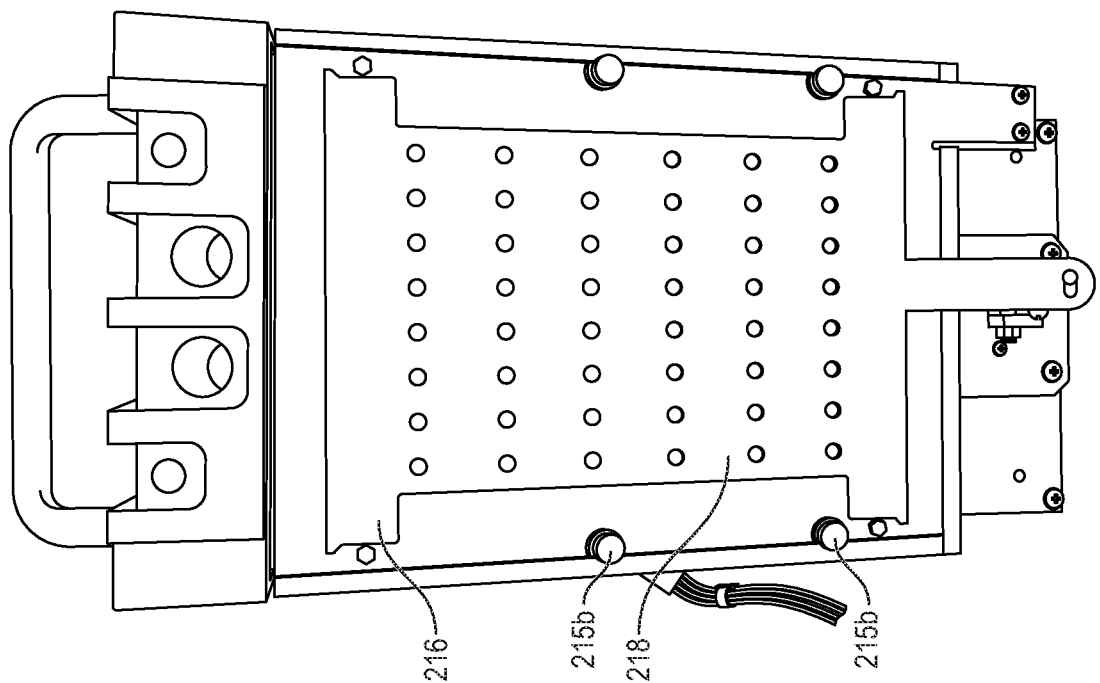

FIGS. 5C-E illustrate first and second subsets of openings 212a, 212b (including 238 and optionally 142) in the enclosure 102 which can provide access to a cell culture plate 114 located within the enclosure 102 when the sealing element 116, 216 is in a first open position and a second open position, respectively. FIG. 5C illustrates the sealing element 216 in a closed position such that the openings 212 of the lid 206 are occluded. FIG. 5D illustrates the sealing element 216 in a first open position such that a first plurality of openings 218 (not shown) in the sealing element 216 are in register with the rows of openings 212a of the lid 206, resulting in the rows of openings 212a being open, while the rows of openings 212b are occluded. FIG. 5E illustrates the sealing element 216 in a second open position such that the first plurality of openings 218 (not shown) in the sealing element 218 are in register with the rows of openings 212b of the lid 206, resulting in the rows of openings 212b being open, while the rows of openings 212a of the lid 206 are occluded.

In some embodiments, the sealing element 116, 216 may further have a second plurality of openings 118, 218 which may be different from the first plurality of openings 118, 218. For example, the second plurality of openings 118, 218 may be in a physically different location from the first plurality of openings 118, 218. The first and second plurality of openings 118, 218 may correspond to subsets of the plurality of openings (112, 212, 138, 238, and optionally 142) in the enclosure 102, e.g., the number of openings in the first and/or second plurality of openings 118, 218 in the sealing element 116, 216 may be fewer than the number of openings (112, 212, 138, 238, and optionally 142) in the enclosure 102. In some embodiments, the number of openings in the first and/or second plurality of openings 118, 218 in the sealing element 116, 216 is one-half, one-third, one-fourth, one-sixth, one-twelfth, or fewer the number of openings (112, 212, 138, 238, and optionally 142) in the enclosure 102.

In some embodiments, the sealing element 116, 216 may further have a third plurality of openings 118, 218, which may be different from the first and/or second plurality. For example, the third plurality of openings 118, 218 may be in a physically different location from the first plurality and/or second plurality of openings 118, 218. In some embodiments the number of openings in the third plurality of openings 118, 218 in the sealing element 116, 216 is one-half, one-third, one-fourth, one-sixth, one-twelfth, or fewer the number of openings (112, 212, 138, 238, and optionally 142) in the enclosure 102. In some embodiments, the number of openings in the first, second, and/or third plurality of openings 118, 218 in the sealing element 116, 216 is one-half, one-third, one-fourth, one-sixth, one-twelfth, or fewer the number of openings (112, 212, 138, 238, and optionally 142) in the enclosure 102.

When the sealing element 116, 216 is moved between a closed position, in which the sealing element 116, 216 covers the plurality of openings (112, 212, 138, 238, and optionally 142) in the enclosure 102, to the first open position, then the first plurality of openings 118, 218 of the sealing element 116, 216 come into register with a first subset of the plurality of openings (112, 212, 138, 238, and optionally 142) in the enclosure 102, and all other openings in the enclosure 102 that are not in the first subset are occluded. When the sealing element 116, 216 has a second plurality of openings 118, 218, the sealing element 116, 216 may be further moved from the closed position or the first open position to a second open position, wherein the second plurality of openings 118, 218 of the sealing element 116, 216 come into register with a second subset of the plurality of openings (112, 212, 138, 238, and optionally 142) in the enclosure 102, and all other openings in the enclosure 102 that are not in the second subset are occluded. When the sealing element 116, 216 has a third (or further) plurality of openings 118, 218, the sealing element 116, 216 may be moved from the closed position, first open position, or the second open position to a third (or further) open position, wherein the third (or further) plurality of openings 118, 218 in the sealing element 116, 216 come into register with a third (or further) subset of the plurality of openings (112, 212, 138, 238, and optionally 142) in the enclosure 102, and all other openings in the enclosure 102 that are not in the third (or further) subset are occluded. The subset of the openings (112, 212, 138, 238, and optionally 142) in the enclosure 102 opened by moving the sealing element 116, 216 to the first, second, third, or further open position may be non-overlapping with the subset of openings (112, 212, 138, 238, and optionally 142) in the enclosure 102 opened by moving the sealing element 116, 216 to one or all of the other open positions.

Size(s) of openings in the enclosure and the sealing element. The plurality of openings (112, 212, 138, 238, and optionally 142) in the enclosure 102 (which includes openings in the lid 106, 206 and the openings in the elements making up the lid assembly 108) and the one or more pluralities of openings 118, 218 in the sealing element 116, 216 can be sized to allow for an import/export tip to access individual wells 120 in the cell culture plate 114. In some cases the openings can be sized to correspond to the size and shape of the wells 120 in the cell culture plate 114. In other embodiments, the plurality(ies) of openings (112, 212, 138, 238, and optionally 142) in the enclosure 102 and openings 118, 218 of the sealing element 116, 216 can be sized just sufficiently large to permit the import/export tip to access the individual wells 120 in the cell culture plate 114 without necessarily being of the same size or shape as the wells 120. For instance an opening may be octagonal while the well 120 may be round or the opening may be slightly smaller than the well 120, while still permitting the import/export tip to access the well 120. In some embodiments the openings (112, 212, 118, 218, 138, 238, and optionally 142) can be sized to restrict the vapor phase in the internal chamber 110 of the incubator 100 from passing through the openings to the exterior of the incubator 100.

In various embodiments, the plurality(ies) of openings (112, 212, 118, 218, 138, 238, and optionally 142) in the enclosure 102 and/or the sealing element 116 may independently have a diameter of about 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.2 mm, 2.4 mm, 2.6 mm, 2.8 mm, 3.0 mm, 3.2 mm, 3.4 mm, 3.6 mm, 3.8 mm, 4.0 mm, 4.2 mm, 4.4 mm, 4.6 mm, 4.8 mm, 5.0 mm, 5.2 mm, 5.4 mm, 5.6 mm. 5.8 mm. 6.0 mm, 6.2 mm, 6.4 mm, 6.6 mm, 6.8 mm, 7.0 mm, 7.2 mm. 7.4 mm. 7.6 mm. 7.8 mm, 8.0 mm, 8.2 mm, 8.4 mm, 8.6 mm, 8.8 mm, 9.0 mm, 9.2 mm, 9.4 mm, 9.6 mm, 9.8 mm, or about 10.0 mm. In some embodiments the plurality(ies) of openings in the enclosure 102 and/or the sealing element 116, 216 may independently have a diameter of about 1 mm to about 10 mm. In some embodiments the plurality(ies) of openings in the enclosure 102 and/or the sealing element 116, 216 may independently have a diameter of about 1 mm to about 5 mm. In some embodiments the plurality(ies) of openings in the enclosure 102 and/or the sealing element 116, 216 may independently have a diameter of about 1.5 mm to about 4.5 mm. In some embodiments the plurality(ies) of openings in the enclosure 102 and/or the sealing element 116, 216 may independently have a diameter of about 1.7 mm to about 4.0 mm. In some embodiments the plurality(ies) of openings in the enclosure 102 and/or the sealing element 116, 216 may independently have a diameter of about 1.7 mm to about 1.8 mm. In some embodiments the plurality(ies) of openings in the enclosure 102 and/or the sealing element 116, 216 may independently have a diameter of less than about 10 mm and more than about 1 mm. In some embodiments the plurality(ies) of openings in the enclosure 102 and/or the sealing element 116, 216 may independently have a diameter of less than about 5 mm and more than about 1 mm. In some embodiments the plurality(ies) of openings in the enclosure 102 and/or the sealing element 116, 216 may independently have a diameter of less than about 4 mm and more than about 1 mm. In some embodiments the plurality(ies) of openings in the enclosure 102 and/or the sealing element 116, 216 may independently have a diameter of less than about 3 mm and more than about 1 mm. In some embodiments the plurality(ies) of openings in the enclosure 102 and/or the sealing element 116, 216 may independently have a diameter of less than about 2 mm and more than about 1 mm.

The diameter of each of the plurality(ies) of openings (112, 212, 118, 218, 138, 238, and optionally 142) in the enclosure 102 and/or the sealing element 116 can be selected based on the process conditions and the properties of the incubator 100 and cell culture plate 114 used with the incubator 100. Examples of process conditions and properties of the incubator 100 include: size and number of openings (112, 212, 118, 218, 138, 238, and optionally 142), a desired vapor flow rate through the openings, cell culture plate 114 configuration including number of wells 120, a desired positive pressure operating range for the internal chamber 110 of the incubator 100, purge gas composition, etc. For example, when a cell culture plate 114 with 96 wells 120 is used with the incubator 100, the openings (112, 212, 118, 218, 138, 238, and optionally 142) in the enclosure 102 and/or the sealing element 116, 216 can each be sized with a diameter of about 1.5 mm to about 4 mm, about 1.7 mm to about 4 mm, or about 1.726 mm to about 4 mm. For example, when a cell culture plate 114 with 384 wells 120 is used with the incubator 100, the openings (112, 212, 118, 218, 138, 238, and optionally 142) in the enclosure 102 and/or the sealing element 116, 216 can each be sized with a diameter of about 1.5 mm to about 2.5 mm, about 1.7 mm to about 2.0 mm, or about 1.726 mm to about 1.8 mm.

The plurality of openings (112, 212, 138, 238, and optionally 142) in the enclosure 102 may have the same diameter size as the size of the diameter of the one or more pluralities of openings 118, 218 in the sealing element 116, 216. The plurality of openings (112, 212, 138, 238, and optionally 142) in the enclosure 102 and the one or more pluralities of openings 118, 218 in the sealing element 116, 216 can include multiple different sizes of openings. A first subset of the plurality(ies) of openings of the enclosure 102 and/or the sealing element 116, 216 can have a first size. A second subset of the plurality(ies) of openings of the enclosure 102 and/or the sealing element 116, 216 can have a second size. In some cases, a third subset of the plurality(ies) of openings of the enclosure 102 and/or the sealing element 116, 216 can have a third size. The first size, second size, and third size can be different. In some embodiments, the size of the openings (112, 212, 138, 238, and optionally 142) of the enclosure 102 is a first size and the size of the openings 118, 218 in the sealing element 116, 216 is a second size, where the second size is different from the first size, as long as the import/export tip can enter.

The seal between the sealing element 116, 216 and other structures in the incubator 100 does not have to be air tight. The seal can be configured to allow some gas flow from the internal chamber 110 through the openings (112, 212, 138, 238, and optionally 142) to the exterior of the incubator 100. For example, a pressurized gas source can be provided to provide a purge gas to the internal chamber 110. A small gas flow of the purge gas can pass through the internal chamber 110 of the enclosure 102 and exit through the openings 112, 212 in the lid 106, 206 while the sealing element 116, 216 is in the closed position to seal the openings 112, 212 in the lid 106, 206. In some embodiments a small positive pressure can be maintained within the internal chamber 110 to prevent or minimize the chance of contamination of the environment in the internal chamber 110. In some embodiments the sealing element 116, 216 is configured to form a seal with the plurality of openings (112, 212, 138, 238, and optionally 142) in the enclosure 102 that allows the enclosure 102 to maintain a pressure between about 0.0005 psi to about 0.01000 psi above ambient pressure in the internal chamber 110 when gas from the pressurized gas source flows into the internal chamber 110.

Internal chamber of the enclosure. The internal chamber 110 volume can be varied to accommodate a cell culture plate 114 having a desired size. In some embodiments the internal chamber 110 has a volume of about 50 cm$^3$ to about 300 cm$^3$. In some embodiments the internal chamber 110 has a volume of about 100 cm$^3$ to about 500 cm$^3$. In some embodiments the internal chamber 110 has a volume of about 200 cm$^3$ to about 750 cm$^3$. In some embodiments the internal chamber 110 has a volume of about 400 cm$^3$ to about 1,000 cm$^3$. In some embodiments the internal chamber 110 has a volume of about 500 cm$^3$ to about 1500 cm$^3$. In some embodiments the internal chamber 110 has a volume of about 750 cm$^3$ to about 2000 cm$^3$.

An incubator 100 as described herein can accommodate cell cultures plates of varying sizes within the enclosure 102. In some embodiments the cell culture plate 114 is a 96-well plate. The 96-well plate can have an 8 well by 12 well configuration. In some embodiments the cell culture plate 114 is a 384-well plate. In some embodiments the cell culture plate 114 can have less than 96 wells. For example a cell culture plate 114 with 12 or fewer wells can be used. In some embodiments the cell culture plate 114 has 6 or fewer wells. The cell culture plates may have either a rounded bottom, which includes a U-shaped bottom, V-shaped, or flat shaped bottom to each of the wells in the culture plate.

Figure 6A:
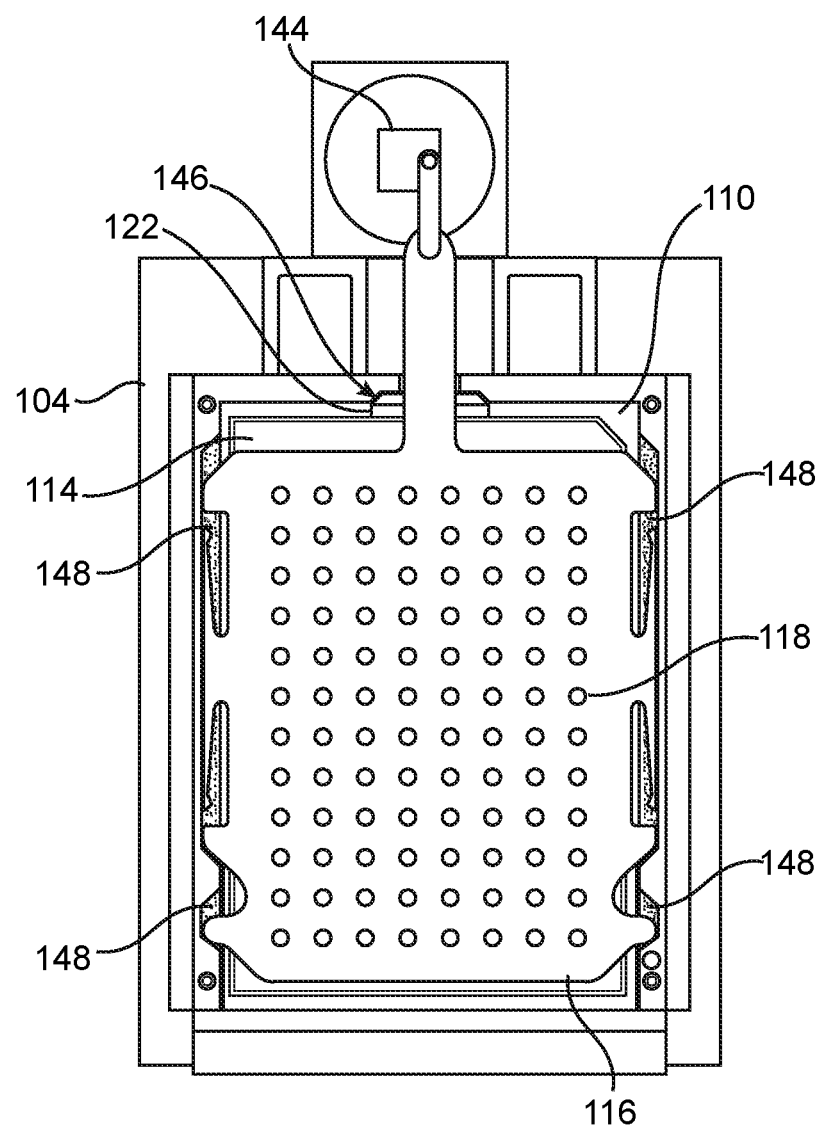
FIGS. 6A-6B illustrate a top view of a portion of an incubator having the sealing element in an open position and closed position, respectively, in accordance with some embodiments.
Figure 6B:
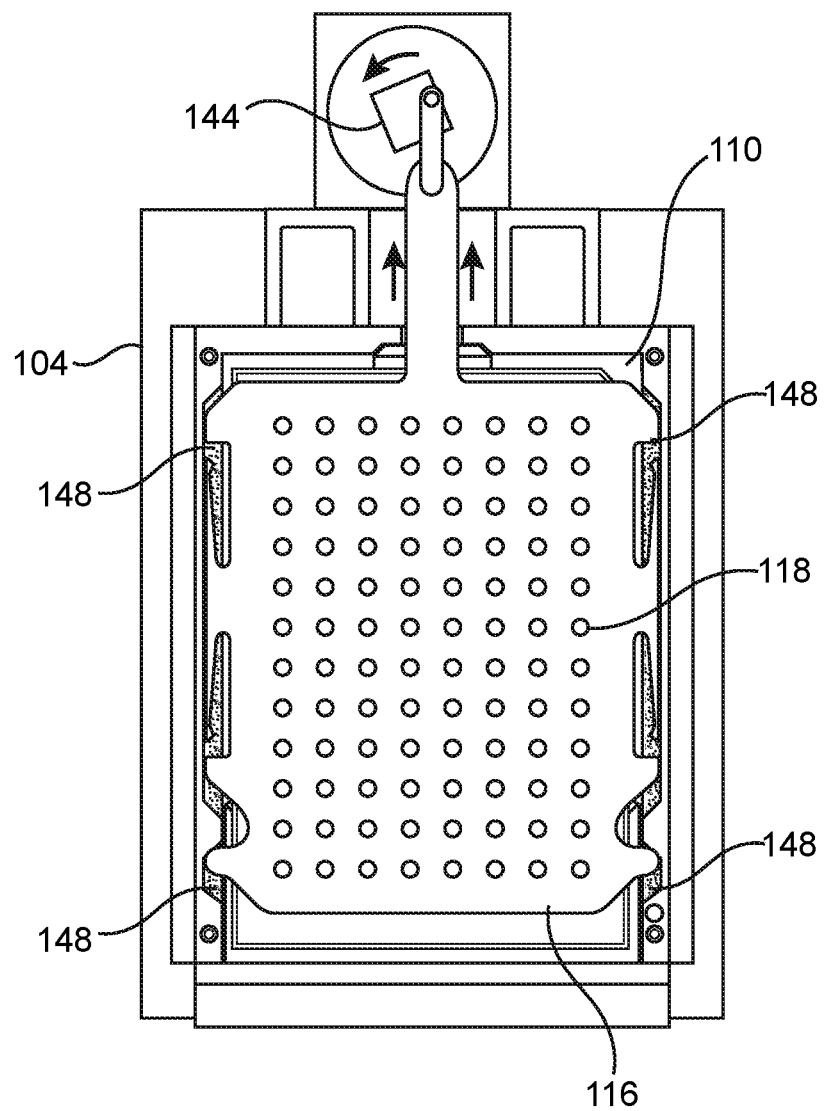
Figure 14:
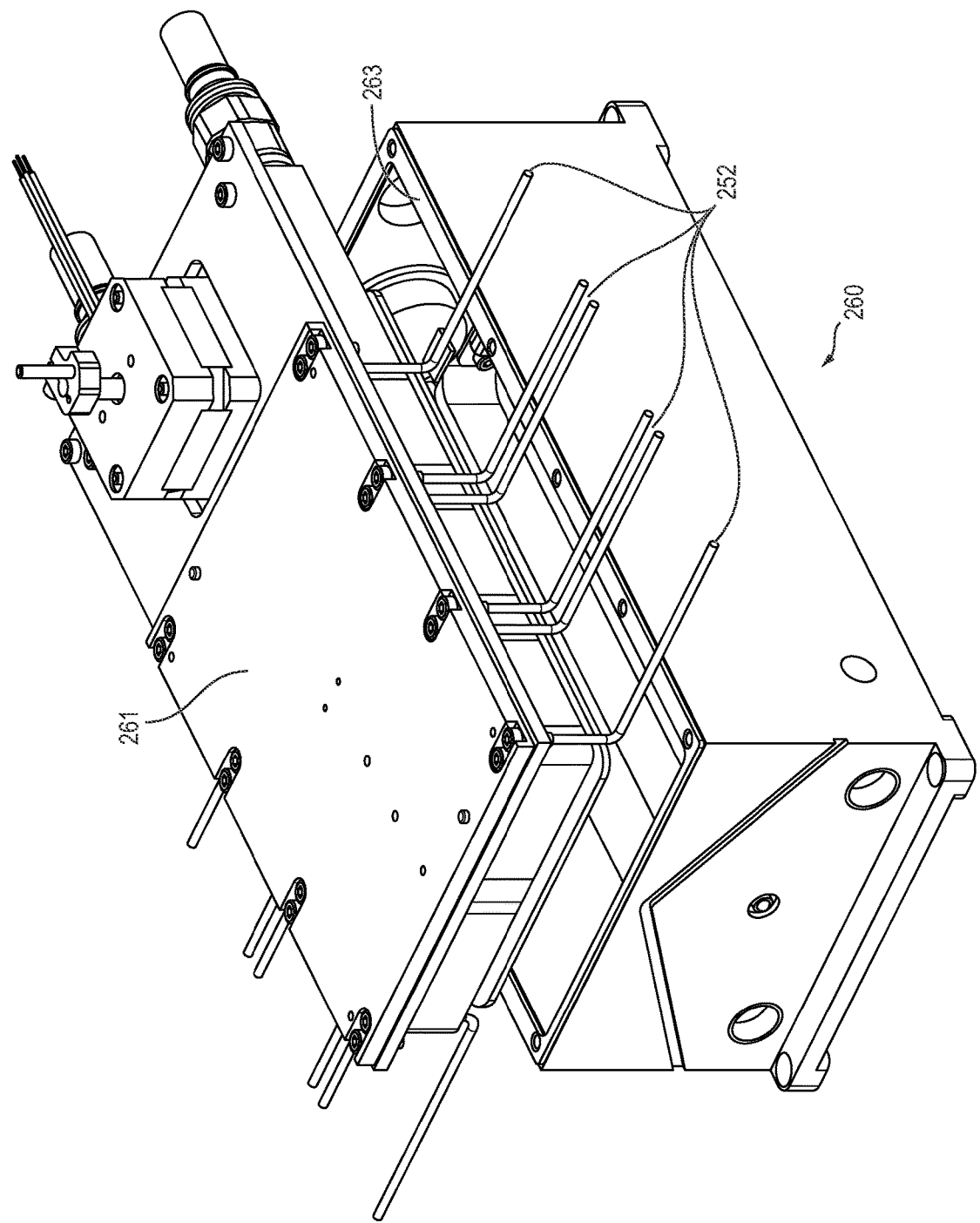
FIG. 14 illustrates an exploded view of an enclosure support of an incubator, in accordance with some embodiments.
Figure 16:
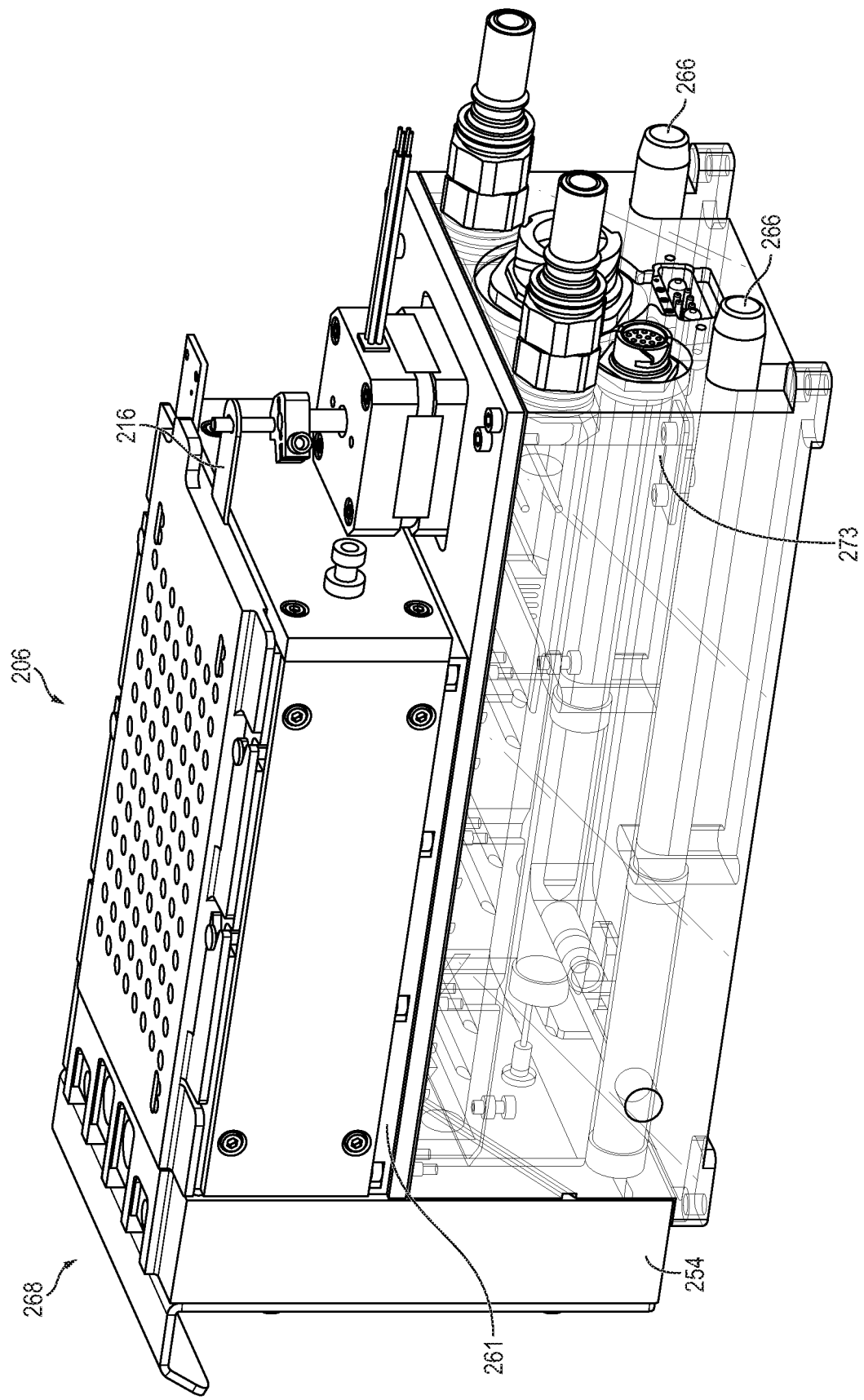
FIG. 16 illustrates a side view of an incubator, in accordance with some embodiments.

Sealing Element Actuator. The incubator 100 can include a sealing element actuator 144 (an exemplar is shown in FIGS. 6A-B and another exemplar is shown in FIGS. 14 and 16). The sealing element actuator 144 can be configured to move the sealing element between an open and a closed position. The sealing element actuator 144 can include a motor or rotary solenoid or similar actuator. For example, in some cases a stepper motor could be used. The stepper motor can, for example, operate with a 0.5 hz frequency. Alternatively, a rotary solenoid can be used that operates with a 60 hz frequency.

In some embodiments, the actuator 144 may be configured to move the sealing element 116/216 between the closed position and an open position. In some embodiments the actuator 144 can be configured to move the sealing element 116, 216 between the closed position and a plurality of open positions. For example, the actuator 144 can be configured to move the sealing element 116, 216 between the closed position and a first open position and a second open position. In some embodiments the actuator 144 can be further configured to move the sealing element 116, 216 to a third (or further) open position. The actuator 144 may be configured to move the sealing element 116, 216 between a first open position and the closed position. The actuator 144 may then be configured to move the sealing element 116, 216 between a second open position and the closed position. The actuator 144 may further be configured to move the sealing element 116, 216 between a third open position and the closed position.

Figure 18:
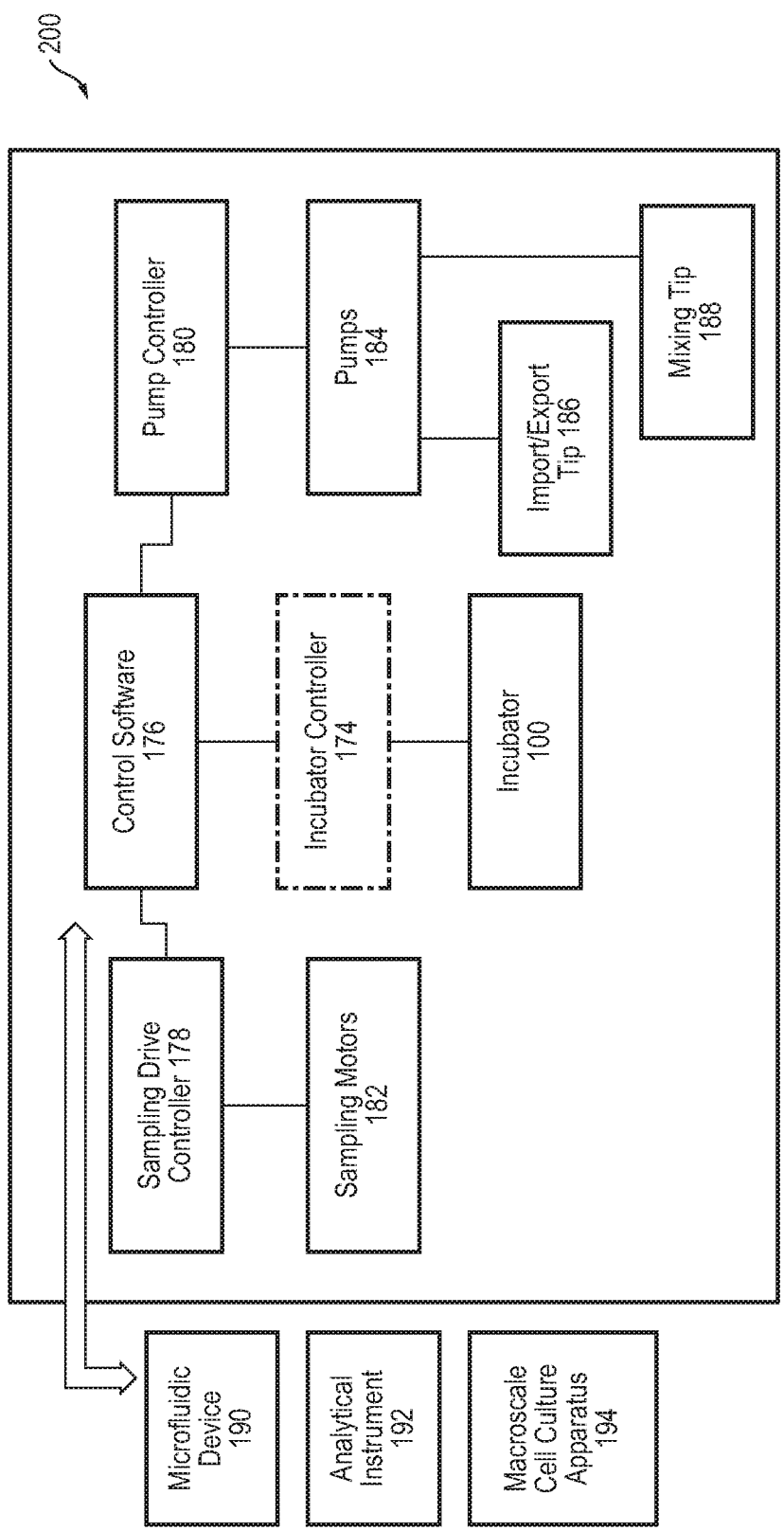
FIG. 18 illustrates a schematic representation of a system for incubation having continuous access for export/import.

The incubator 100 can be configured to maintain a selected internal temperature, humidity, and gas content within the internal chamber 110 of the enclosure 102. The incubator 100 can include a controller 174 (an exemplar is shown in FIG. 18) configured to maintain the selected internal temperature, humidity, and gas content within the internal chamber 110 of the enclosure 102. The internal temperature, humidity, and gas content within the internal chamber 110 of the enclosure 102 can be selected to maintain the materials within the incubator 100. In some embodiments, the temperature may be maintained in a range from about 4° C. to about 40° C. In some embodiments the temperature can be maintained between about 4° C. to about 39° C., about 15° C. to about 39° C., about 20° C. to about 38° C., about 25° C. to about 38° C., or about 30° C. to about 38° C. In some embodiments the relative humidity is maintained above about 60%, 70%, 80%, or above about 90%. In some embodiments, the relative humidity is maintained at about 70%, 75%, 80%, 85%, 90%, or about 95%. In some embodiments the carbon dioxide content is maintained around 1%, 2%, 3%, 4% or around 5%.

Figure 4A:
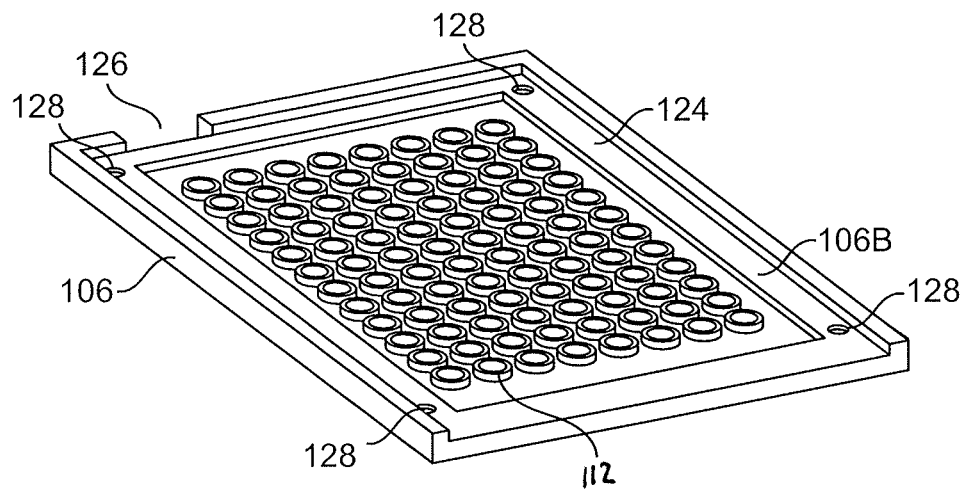
FIGS. 4A-4B illustrate an exploded isometric view of bottom surfaces of a lid and a printed circuit board and its associated connector, respectively, that can be used in some of the embodiments of incubators described herein.
Figure 4B:
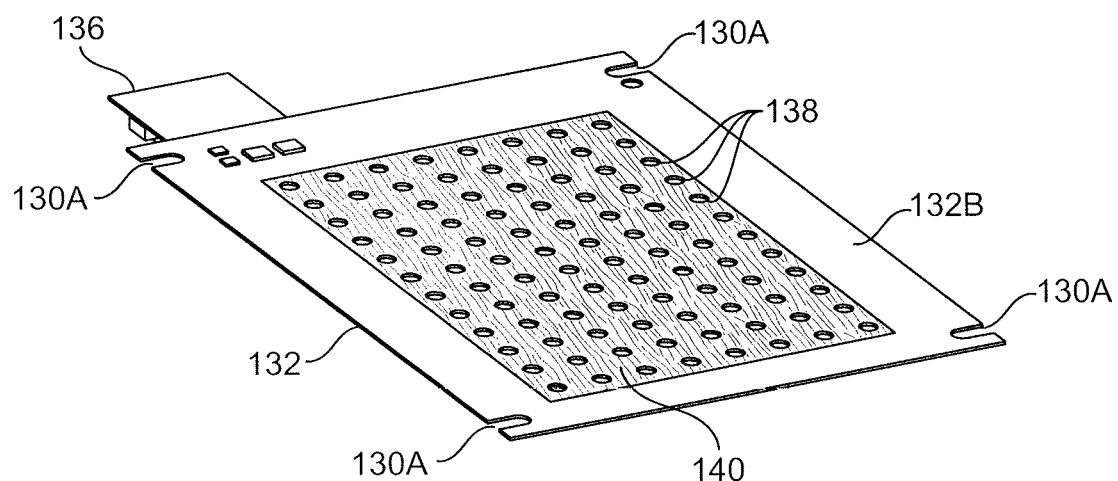

In some embodiments the incubator 100 may include a temperature controller 174 (an exemplar is shown in FIG. 18) configured to maintain a temperature of the internal chamber 110 within a desired range (FIG. 2B, 3B, 4B). The incubator 100 can include a first heating/cooling device engaged with a bottom of the enclosure 102, such as the base 104. Alternatively, the first heating/cooling device can be engaged with a thermally conductive layer that contacts directly or indirectly with the enclosure 102 of the incubator 100. The first heating/cooling device can provide heating or cooling to the thermally conductive layer. The thermally conductive layer can provide heating or cooling to a portion of the enclosure 102. The thermally conductive layer can be made of a thermally conductive material (e.g., aluminum, copper, brass, other copper-containing alloys, or a ceramic), as discussed above. The use of the thermally conductive layer can improve the uniformity of the heat transfer to the enclosure 102. The first heating/cooling device can be controlled by the temperature controller 174. Examples of heating/cooling devices include: a resistive heater, a fluid coil configured to circulate a heat exchange fluid, one or more Peltier devices, and the like. In some embodiments, the fluid coil includes access ports on its exterior to permit entry of fluid for cooling/heating by a Peltier device. In some embodiments having a fluid coil, the heating/cooling device is a separate component from the base 104. In embodiments having a heating/cooling device separable from the base, disassembly is possible to permit autoclaving. In other embodiments, the first heating/cooling device can be integral with the enclosure 102. For example, a fluid coil can be integral with the base 104 of the enclosure 102. The temperature controller 174 can include or receive input from one or more temperature sensors. The temperature sensors can be attached to the PCB 132, 232, a portion of the enclosure 102 (e.g., the base 104), and/or the first heating/cooling device. Examples of temperature sensors include thermistors and/or integrated circuits. Integrated circuits can have less electrical noise and an accuracy of +/−0.25° C. without the need for calibration.

The first heating/cooling device can directly contact (or indirectly provide heat transfer to) an outer surface of the bottom of the enclosure 102, such as the base 104. In some embodiments the first heating/cooling device contacts at least about 75% of the outer surface of the bottom of the enclosure 102. In some embodiments the first heating/cooling device contacts at least about 80% of the outer surface of the bottom of the enclosure 102. In some embodiments the first heating/cooling device contacts at least about 85% of the outer surface of the bottom of the enclosure 102. In some embodiments the first heating/cooling device contacts at least about 90% of the outer surface of the bottom of the enclosure 102. In some embodiments the first heating/cooling device contacts at least about 95% of the outer surface of the bottom of the enclosure 102. In some embodiments, the first heating/cooling device can maintain a temperature in the internal chamber 110 of the enclosure 102 in a range from about 4° C. to about 40° C., about 4° C. to about 39° C., about 4° C. to about 38° C., or about 4° C. to about 37° C. In some embodiments the temperature can be maintained between about 10° C. to about 37° C., about 15° C. to about 39° C., about 20° C. to about 38° C., about 25° C. to about 38° C., about 30° C. to about 38° C. In other embodiments, the first heating/cooling device can maintain a temperature in the internal chamber 110 of the enclosure 102 at about 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. In some embodiments the internal chamber 110 of the enclosure is maintained at about 37° C.

The incubators 100 described herein can include a second heating/cooling device engaged with a top of the enclosure 102, such as a portion of the lid 106, 206 or lid assembly 108 or the PCB 132, 232. The second heating/cooling device can be within the enclosure 102. Examples of heating/cooling devices include: a resistive heater, a fluid coil configured to circulate a heat exchange fluid, and one or more Peltier devices, and the like. In some embodiments, the second heating/cooling device may be a resistive heater. In some embodiments, the second heating/cooling device is part of the PCB 132, 232, which is engaged with the top of the enclosure 102, such as the lid 106, 206. The second heating/cooling device can be controlled by the temperature controller 174 (FIG. 18). The second heating/cooling device can include a plurality of openings 138, 238 that are in register with the plurality of openings (112, 212, 138, 238, and optionally 142) in the enclosure 102. The second heating/cooling device can include resistive heating elements that are part of the PCB 132, 232. The resistive heating elements 140 can be located on a side of the PCB 132, 232 facing the internal chamber 110 of the enclosure 102 and/or the cell culture plate 114 (FIG. 4B) or internal to the PCB 132, 232. In some embodiments, the second heating/cooling device can maintain a temperature in a range from about 4° C. to about 40° C., about 4° C. to about 39° C., about 4° C. to about 38° C., or about 4° C. to about 37° C. In some embodiments the temperature can be maintained between about 10° C. to about 37° C., about 15° C. to about 39° C., about 20° C. to about 38° C., about 25° C. to about 38° C., or about 30° C. to about 38° C. In various embodiments, the second heating/cooling device may maintain a temperature that is 0.1° C., 0.2° C., 0.3° C., 0.4° C., 0.5° C., 0.6° C., 0.7° C., 0.8° C., 0.9° C., 1.0° C., 1.1° C., 1.2° C., 1.3° C., 1.4° C., 1.5° C., 1.7° C., 1.9° C., 2.0° C., 2.3° C., 2.5° C., 2.7° C., 2.9° C., 3.0° C., 3.3° C., 3.5° C., 3.7° C., 3.9° C., 4.0° C., 4.3° C., 4.5° C., 4.7° C., 4.9° C. or 5.0° C. higher than the first heating/cooling device. When the second heating/cooling device maintains a temperature that is higher than the temperature maintained by the first heating/cooling device, condensation near the top of the internal chamber 110, and hence on the cell culture plate 114, may be prevented.

Cell culture plate support. The incubators 100 disclosed herein can include a support 122, 222 for the cell culture plate 114, 224 (an exemplar is shown in FIG. 1B, FIGS. 7-8 and in FIGS. 10A-10B). The cell culture plate support 122, 222 can be configured to slideably move relative to the enclosure 102 from a position within the enclosure 102 to a position outside of the internal chamber 110 of the enclosure 102. The illustrated supports 122, 222 have a T-shape, although other shapes can be used to support the cell culture plate 114. The support 122, 222 for the cell culture plate 114 can be attached to an access door 154 on the incubator 100, either directly or engaged through one or more intervening structures or parts, such as the biased connections 255 (FIGS. 11A-11C). The culture plate support 122, 222 may be made of a plastic. In some embodiments, the culture plate support 122, 222 may be made of metal, which may be brass, in one non-limiting example. The support can also include a distal lip 223 on the support 222 for the cell culture plate 114 (See one exemplar in FIGS. 17A-17B).

In some embodiments the support 122, 222 for the cell culture plate 114 and the access door 154, 254 can form an access assembly 168, 268 (an exemplar is shown in FIG. 8 and in FIGS. 11A-11B). The access assembly 168, 268 can include a front plate 156, 256 that sealably interfaces with a portion of the enclosure 102 as shown in FIGS. 7-9 and 10A. The access assembly 168, 268 can include a floating connection between the front plate and the access door. For example, a biased connection 255 between the front plate and the access door can be configured to provide a compressive force to the front plate to seal the front plate relative to a portion of the enclosure 102 (See one exemplar in FIGS. 11A-11B). The access assembly may be configured such that the cell culture support 122, 222 maintains the cell culture plate 114 at a height within the enclosure 102 such that the passages 150A introducing the environmental or purging gas(es) are at the same height, relative to the bottom and top of the enclosure, as the cell culture plate 114. (See description below.) Keeping the gas entry at the same level as the cell culture plate provides optimized humidity control, optimized gas circulation and prevents condensation on the cell culture plate. Accordingly the support notch 146 may be configured to support the side of the cell culture support at the same height at the passages for gas 150A. In some embodiments, the top of the cell culture plate 114 is at least about 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or about 20 mm from the top of the internal chamber 110 of the enclosure 102. In some embodiments, the lower surface of the cell culture plate support is at least about 0 mm, 1 mm, 2 mm, 3 mm, 4 mm, 5 mm, 6 mm, 7 mm, 8 mm, 9 mm, or about 10 mm from the bottom inner surface of the internal chamber 110 of the enclosure 102.

The access assembly 168, 268 may include track guides 166 or rails 266 to permit the access assembly 168, 268 to slide open or shut, permitting access to the cell culture plate 114. The track guides 166 or rails 266 can be configured to slide relative to tracks 162, 262 on an enclosure support 160, 260. The movement of the access assembly 168, 268 may be directed by a controller 174 (See FIG. 18), which may be included as part of incubator 100.

The access assembly 168, 268 can be movably mounted on an enclosure support 160, 260 that also supports the enclosure 102. The enclosure support 160 can include tracks 162 such that the access assembly 168 may slide on track guides 166 relative to the tracks 162 on the enclosure support 160. The track guides 166 can have various cross-sectional shapes. In one example the track guides can have a flat surface with a rectangular or square cross sectional shape as shown in FIG. 8. In some embodiments the track guides 166 can have a circular or rounded cross-sectional shape such as the rails 266 illustrated in FIGS. 10B, 11A, and 11B. The front plate 156, 256 of the access door 154, 254 may be made of a metal or a plastic, similarly to the materials described above as suitable for the enclosure 102. In some embodiments, the front plate 156, 256 is made of a material having high thermal conductivity (e.g., aluminum, copper, brass, a copper-containing alloy, or a ceramic). The access door 154, 254 may be made of metal or plastic, and may have a handle 172, 272. The culture plate support may be detachable from the access door 154, 254 for cleaning, for example, by autoclaving. The front plate 156, 256 and access door 154, 254 may also be cleaned by autoclaving, either as assembled or with disassembly.

The track guides/rails of the access assembly 168, 268 can include one or more stops or engagement surfaces to help hold the access assembly 168, 268 in one or more discrete positions, such as open and closed positions. The track guides 166 or rails 266 can include an engagement surface configured to engage with a complementary structure of the enclosure support 160, 260 to secure a position of the access assembly 168, 268 relative to the enclosure support 160, 260. The position of the access assembly 168, 268 can correspond to an open or closed position of the access assembly 168, 268. In some embodiments the incubator can include a door switch configured to mechanically, electronically, or magnetically engage with a complementary structure of the access assembly 168, 268.

In some embodiments the support 122 for the cell culture plate 114 can be one or more internal surfaces or features mounted on or fabricated as part of the internal surface of the enclosure 102. For example, one or more projections can extend from the sides of the enclosure 102 towards the internal chamber 110 to support the cell culture plate 114 within the internal chamber 110. In another example, the internal surface of the enclosure 102 may be notched to provide a resting support 146, 246, 247 (exemplars shown in FIGS. 7, 17A, and 17B) for a portion of the culture plate support 122, 222 opposite to its attachment to the front plate 156, 256 (an exemplar is shown in FIG. 7). When the cell culture plate 114 is placed on the support 122, 222 within the enclosure 102, the openings (112, 212, 138, 238, and optionally 142) in the enclosure 102 may be in register with the wells 120 in the cell culture plate 114.

The incubator 100 can include at least one passage 150A in the enclosure 102 configured for gas entry (an exemplar is shown in FIGS. 7-8). The passage can be used to supply a purge gas or other gas selected to maintain the desired internal environment within the incubator 100. In some embodiments, the gas entry passage(s) 150A may be formed through a wall of the base 104. In some embodiments, the gas entry passage(s) 150A is at least about 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm from the top of the internal chamber 110 of the enclosure 102. In some embodiments, the gas entry passage(s) 150A are located at a height on a side of the base that is equivalent to the height of a side of the cell culture plate 114 when supported within the enclosure 102. The gas may be provided to maintain a positive pressure within the internal chamber 110. For example, the pressure of the internal chamber 110 can be maintained between about 0.0005 psi to about 0.01000 psi above ambient pressure. Clean rooms typically use a positive pressure of about 0.0072 psi or less. In some embodiments the pressure of the internal chamber 110 can be maintained less than about 0.0072 psi above ambient pressure. In some embodiments the pressure of the internal chamber 110 can be maintained above about 0.0072 psi above the ambient pressure. In some cases, the flow rate of the gas can be less than or about 10 liters per hour, 9 liters per hour, 8 liters per hour, 7 liters per hour, 6 liters per hour, 5 liters per hour, 4 liters per hour, 3 liters per hour, 2 liters per hour, or 1 liter per hour. The flow rate may be more than about 0.5 liter per hour. In some embodiments the flow rate can be about 1 liter/hour to about 10 liters/hour.

The purge or environmental gas may be conditioned to provide a desired humidity as well as a desired mixture of gases. In some embodiments the environmental gas is conditioned to provide a relative humidity above about 50%, 60%, 70%, 75%, 80%, 85%, or above about 90%. In some embodiments, the gas is conditioned to provide a relative humidity of about 70%, 75%, 80%, 85%, 90%, or about 95%. In some embodiments the environmental gas is conditioned to provide a carbon dioxide content of around 1%, 2%, 3%, 4% or around 5%.

In some embodiments the internal chamber 110 of the enclosure 102 can include a reservoir configured to hold a fluid, such as a fluid reservoir. The incubator 100 can include at least one fluid drain passage 150B in the enclosure 102 configured to drain the fluid reservoir within the enclosure 102 or drain the enclosure 102 itself (an exemplar is shown FIGS. 7-8). In some cases, the fluid can be used to provide humidity to the internal chamber 110. In some cases, the fluid can be used to control the temperature of the internal chamber 110. In some embodiments, the fluid drain passage 150B may be formed through a side wall of the base 104. The fluid drain passage 150B can be sealable.

The incubator 100 may include electrical connections 152, 252 to power the sealing actuator 144, heat and cool the enclosure 102, open and shut the culture plate support 122, 222, and/or operate the sensors of the PCB 132, 232, amongst other operations (an exemplar is shown in FIG. 8 and another in FIG. 14). The electrical connections 152, 252 may be connected to the first heating/cooling device contacting the bottom side of the base 104, enclosure support 160, 260, enclosure 102, PCB 132, 232, sealing element 116, 216 or other components of the lid assembly 108.

The incubator 100 can include an enclosure support 160, 260 configured to support the enclosure 102 (See one exemplar in FIGS. 7-8 and another exemplar in FIG. 14). One or more adjustable connectors on support legs 164 can be configured to connect the enclosure support 160 to the enclosure 102.

The incubators described herein can be configured to reduce or minimize the formation of condensation within the enclosure or on other parts of the incubator. The lid 106, 206 can be designed to minimize the formation of condensation on parts of the lid while also making the lid easy to clean using autoclaving or other cleaning methods. In one example, the lower side of the lid can have some of the recesses filled with a foam cell polymer that is in register with the openings 112, 212 of the lid 106, 206. In another example, portions of the recesses can be filed with materials such as a hydrophobic material like Parylene™ and/or with Kapton™ sheets or tapes. In yet another example, some of the recesses could be sealed using a thin metal sheet. In yet another example the structure of the lid could be inverted so that the textured side faces the exterior of the incubator. In another example the interior surface of the lid 106, 206 can be shaped to include additional flat section to improve sealing. In some cases, the PCB 132, 232 could be used to heat the lid to a slightly higher temperature, e.g., up to about 40° C. to reduce condensation on the lid 106, 206. In other cases, a positive pressure within the enclosure can be used to add a controlled leak across the lid 106, 206. The contour of the interior of the lid 106, 206 could also be shaped to channel and control drainage of any condensation formed on the lid 106, 206. The PCB 132, 232 can also include a conformal coating to reduce or minimize corrosion on the PCB 132, 232 from condensation.

The incubators 100 as described herein may be further be understood by examining the details in FIGS. 1-17. While FIGS. 1-17 illustrate various features of exemplary incubators, it is to be understood that the Figures are for illustration purposes only and in no way limit the invention to the embodiment shown explicitly. Variations of each element of the incubator 100 may be made as described throughout the description herein.

Figure 1B:
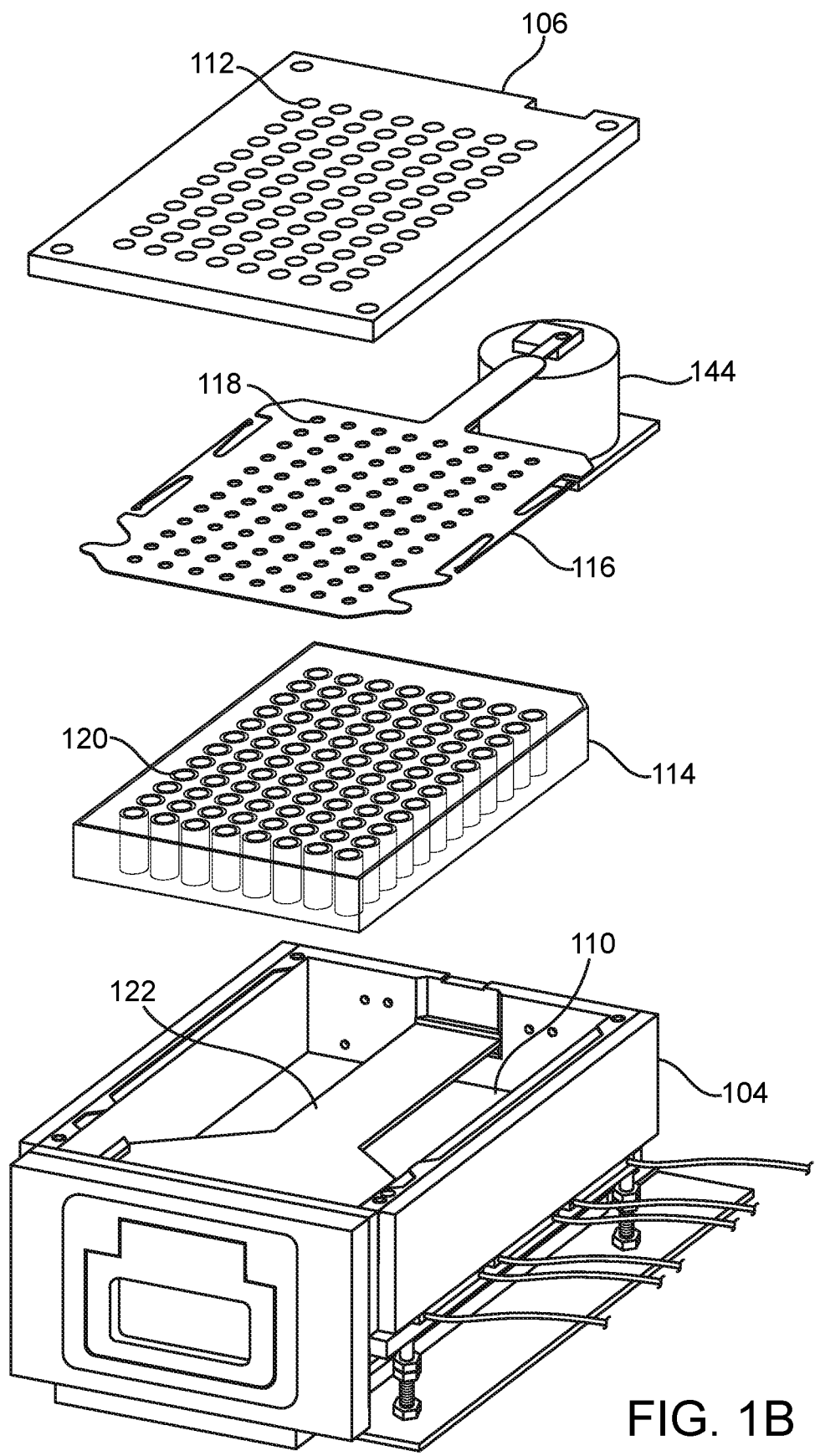

FIGS. 1A-1B illustrate an isometric view and an exploded isometric view of an incubator 100, respectively, in accordance with some embodiments. The incubator 100 includes an enclosure 102 where the enclosure 102 includes a base 104 and lid 106. The base 104 and lid 106 can define the enclosure 102 having an internal chamber 110. The lid 106 includes a plurality of openings 112. The internal chamber 110 is sized to receive a cell culture plate 114. The incubator 100 includes a sealing element 116 with a plurality of openings 118, which is illustrated with a sealing element actuator 144. The illustrated cell culture plate 114 includes a plurality of wells 120. The illustrated cell culture plate 114 has an 8 by 12 arrangement of 96 wells 120. The openings 112 of the lid 106, openings 118 of the sealing element 116, and wells 120 of the cell culture plate 114 can be configured to be in register. The incubator 100 includes a support 122 for the cell culture plate 114.

FIGS. 2A-2C illustrate a top view of a lid 106 and lid assembly 108 of an incubator 100, the lid assembly 108 including printed circuit board (PCB) 132 and an optional spacer 134 respectively, in accordance with some embodiments. FIGS. 3A-3C illustrate an exploded isometric view of the top sides of the lid 106, PCB 132 and spacer 134, respectively, that can be used in the embodiments of incubators 100 described herein. FIG. 2A shows a top side 106A of the lid 106. The openings 112 of the lid 106 extend through the thickness of the lid 106. The lid 106 also includes a cut out 126 to accommodate another portion of the incubator 100, such as the connector 136 of the printed circuit board 130. The lid 106 includes connector openings 128 that can be used to removably attach the lid 106 to the base 104. FIG. 2B shows a top view of a printed circuit board (PCB) 132 and connector 136. The PCB 132 includes openings 138. The openings 138 can be configured to be in register with the openings 112 on the lid 106. Cutouts 130A can be used to place PCB 132 in register with the lid 106, allowing connectors to align connector openings 128 to attach the lid 106 and PCB 132 to the base 104. FIG. 2C shows a top view of the spacer 134. The openings 142 can be configured to be in register with openings 112 on the lid and also with openings 138 on the PCB 132. Cutouts 130B of the spacer 134 can be used to place PCB 132 in register with the lid 106 and the PCB 132, allowing connectors to align connector openings 128 to attach the lid 106, PCB 132, and spacer 134 to the base 104.

Figure 3D:
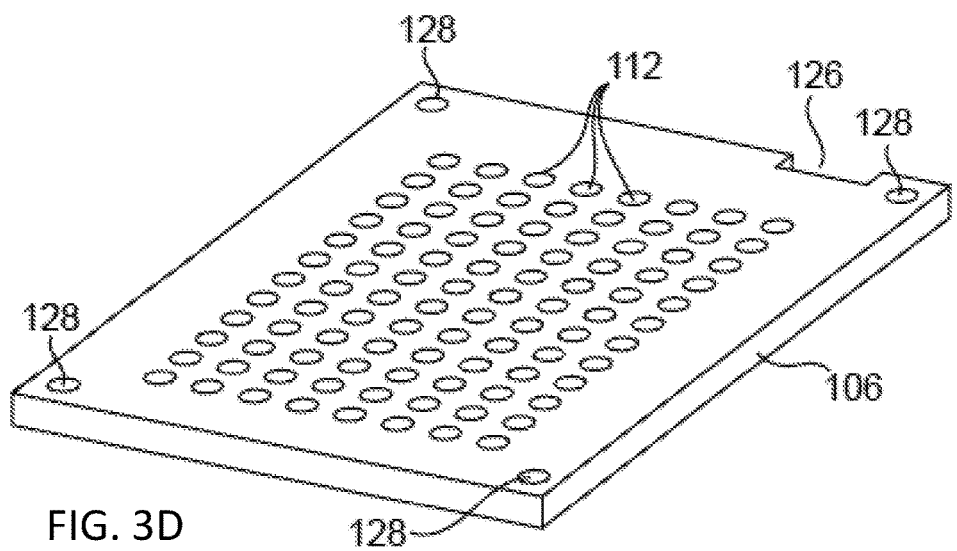
FIGS. 3D-3F illustrate an exploded isometric view showing the top surface of a lid, a sealing element, and a printed circuit board and its associated connector, respectively, that can be used in the embodiments of incubators described herein.
Figure 3E:
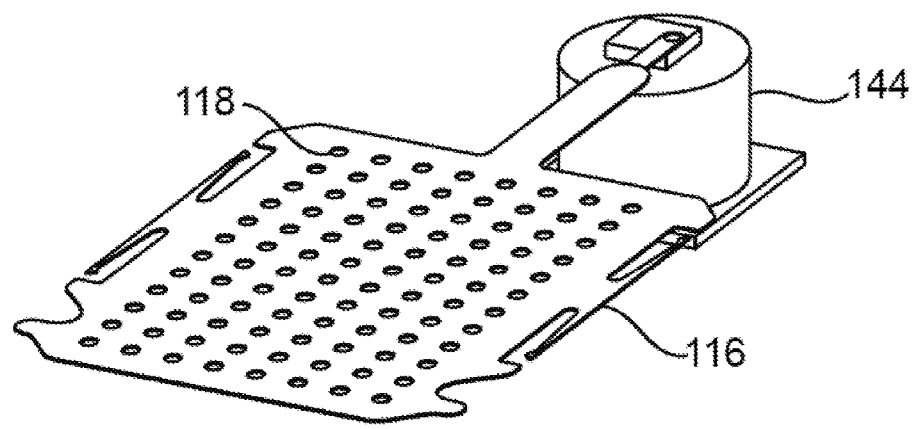
Figure 3F:
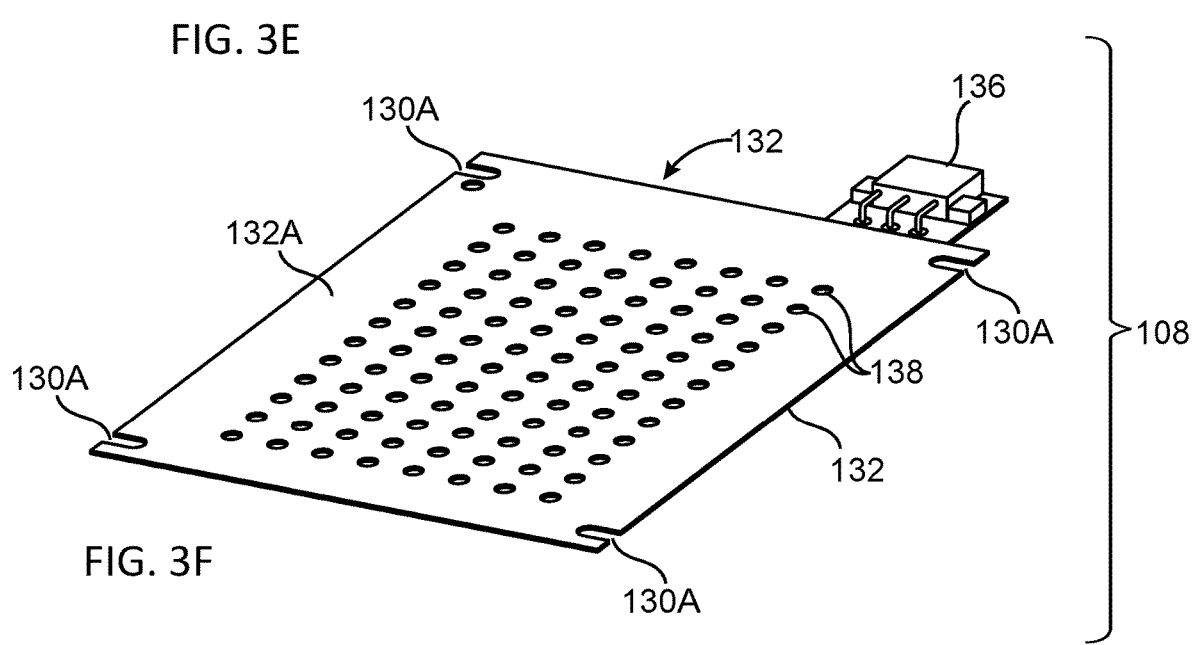

FIGS. 3D-3F illustrate an exploded isometric view showing the top surface of a lid 106, a sealing element 116, and a printed circuit board 132 and its associated connector, respectively, that can be used in the embodiments of incubators described herein. In contrast to FIGS. 3A-3C, the configuration illustrated in FIGS. 3D-3F omits the spacer 134 and positions the sealing element 116 between the lid 106 and PCB 132. Positioning the sealing element 116 between the lid and PCB 132 can improve the overall seal because the sealing element can form a seal between each of the lid 106 and PCB 132.

FIGS. 4A-B illustrate an exploded, isometric view of the bottom side of the lid 106 and PCB 132. In FIG. 4A, the bottom side 106B of the lid 106 includes a recess 124 around a portion of a perimeter of the lid 106. An upper side 132A of the PCB 132 (FIG. 3A) can be configured to engage with the bottom side 106B of the lid 106. For example, the recess 124 of the lid 106 can be sized and shaped to receive the PCB 132. When the lid 106 and PCB 132 are engaged, openings 112 and 138 may be aligned. The notch 126 may be sized to permit the connector 136 to fit when the lid 106 and PCB 132 are engaged. Connector openings 128 may be used to align the lid 106 to the base 102. The openings 112 in the lid 106, may have raised rings around the openings on the bottom side 106B of the lid 106.

As shown in FIG. 4B, the bottom side 132B of the PCB 132 is illustrated. Cutouts 130B can be used to align the PCB 132 when engaged with the lid 106 as the lid 106 is attached to the base 104. A controller 174 (See FIG. 18) can control a heater 140 which is fabricated upon a bottom surface 132B on the PCB 132. The heater 140 can be engaged with the PCB 132 or integrally formed with the PCB 132 such that it does not obstruct the openings 138. The PCB 132 can include a plurality of sensors as discussed above, and can be present in any combination of temperature, humidity and/or gaseous phase sensors.

FIGS. 2A-C, 3A-F, and 4A-B taken together show various relationships between the lid, PCB 132 and optional spacer 134 for alignment and order of mounting and for alignment of the openings in the lid and components of the lid assembly 108.

FIG. 5A illustrates a lid 206 that can be used in the embodiments of incubators described herein. The lid 206 includes a lid cover 207. The outer surface 207 of the lid 206 includes a marking 207a of an instruction such as "pull up to remove" on the lid cover 207. The lid 206 also includes instructions 215c on the compression tabs 215, such as "push to install". The marking 207a and instructions 215c can colored, etched, or adapted to be machine readable by a computer imaging program.

The lid can include various protrusions and contouring on the underside of the lid. FIG. 4A and FIG. 5B illustrate different lid configurations. FIG. 5B illustrates a view of a bottom surface of a lid 206 of an incubator in accordance with some embodiments. The lid 206 includes a plurality of openings 212. The lid 206 includes a patterned surface that includes a plurality of recesses that substantially surround groups 213 of openings 212. The sealing element 116, 216 can move between the closed and different open positions to allow a tool to access the wells 120 of the cell culture plate 114. The groups 213 of the openings 212 can improve a seal formed between the lid 206 and the sealing element 116, 216 when the sealing element 116, 216 is in the closed position. For example, the openings 118, 218 in the sealing element 116, 216 can be occluded by the space between the openings 212 of the groups 213. The openings 212 to the left side of the groups 213 can form a first subset of openings while the openings 212 to the right side of the groups 213 can form a second subset of openings 212.

FIGS. 5C-5E illustrate a top view of an incubator with a sealing element at various positions in accordance with some embodiments. FIG. 5C illustrates the sealing element 216 in a closed position such that the openings 212 of the lid 206 are occluded. FIG. 5D illustrates the sealing element 216 in a first open position such that the openings 212 of the lid 206 are open in every other row of openings 212 with the other rows of openings 212 occluded. FIG. 5E illustrates the sealing element 216 in a second open position such that the openings 212a of the lid 206 are open in every other row of openings 212 with the other rows of openings 212b occluded. The open openings 212 and occluded openings 212 are reversed between the first open position (FIG. 12B) and second open position (FIG. 12C). In FIG. 5E the openings 212b are open and 212a are occluded. The lid 206 also includes four compression tabs 215 with each tab having a surface 215a adapted to engage a pin 215b to secure the lid to the incubator. The compression tab 215 surface 215a can flex downward to engage the pin 215b to provide a pressure to hold the lid 206 in place.

FIG. 5F-5G illustrate a top view of a sealing element 216 of an incubator at various positions in accordance with some embodiments. FIG. 5F shows the sealing element 216 at a closed position such that the openings 218 are not in register with openings 212a/212b of the lid 206 (not shown). FIG. 5G shows the sealing element 216 at a first open position such that the openings 218 are in register with a first subset of openings 212 of the lid 206 (not shown). The illustrated sealing element 216 has six rows of openings 218. The sealing element 216 can be used with the lids 206 illustrated in FIGS. 5C-5E with 12 rows of openings 212. The sealing element 216 can be moved between the closed, first open, and second open position depending on the desired well 120 access for the cell culture plate 120. The illustrated sealing element 216 can be positioned between the lid 206 and PCB 232. Positioning the sealing element 216 between the lid 206 and PCB 232 can improve the overall seal because a seal can be formed between the sealing element 216 and lid 206 and a second seal formed between the sealing element 216 and PCB 232.

FIG. 5H illustrates a top view of an incubator including a printed circuit board (PCB) 232 with openings 238 in accordance with some embodiments. The incubator is shown with the lid 206 and sealing element 216 removed to expose the PCB 232. The PCB 232 can include a multi-layer construction. For example, in one embodiment the PCB 232 can include a four-layer board. Heating elements or devices, such as copper layers, can be internal layers of the PCB 232 to protect the heating elements from exposure to moisture in the air within the enclosure. The use of a multi-layer construction for the PCB 232 can result in a thicker and less flexible PCB 232. The less flexible PCB 232 can improve the seal formed between the PCB 232 and the sealing element 216.

FIGS. 6A and 6B illustrate a top view of a portion of an incubator 100 in accordance with some embodiments. The top view of the incubator 100 shows the base 104 and sealing element 116. The sealing element 116 includes sealing element openings 118. The sealing element 116 can be moved with a sealing element actuator 144. Within the internal chamber 110, the end of the cell culture plate support 122 distal to a front side of the base 104 resting upon support notch 146 is visible. A culture plate 114 is present in this view. Notches 148 in the upper inner edge of the base 104 permit movement of the sealing element 116 as it is actuated between a closed positon and one or more open positions. Other arrangements of notches 148 are possible to support actuation to more than one open position.

The sealing element 116 is in a first position in FIG. 6A and a second retracted position in FIG. 6B. The sealing element actuator 144 is illustrated as rotating to retract the sealing element 116 in FIG. 6B. Movement of the sealing element 116 is facilitated by notches 148 on an inner upper edge of the base 104. The first position and second retracted position can correspond to open and closed positions for the sealing element 116. In the open position the sealing element 116 openings 118 line up with the wells 120 (not shown) of the cell culture plate 114 (not labelled in FIG. 6B) and the lid openings 112 (not shown in this view) such that an import/export tip (not shown) can be used to pass through the openings (112, 118) to access the wells 120 from the exterior of the incubator 100. In the closed position the sealing element 116 blocks or partially obscures the openings 112 of the lid 106 (not shown in this view). It is not required that sealing element 116 form an air tight seal for the openings 112 of the lid 106. For example, in some cases the sealing element 116 can allow a purge gas to flow out of the interior chamber 110 of the incubator 100.

FIGS. 7-8 illustrate an exploded isometric view of a portion of an incubator 100, showing the sealing element 116 having openings 118 connected to actuator 144; a cell culture plate 114 with wells 120; and base 104 with an access door 154 in a closed and an open position, respectively. Visible in the view of the base 104 in FIGS. 7 and 8 is internal chamber 110, support notch 146 upon which cell culture plate support 122 rests when the incubator 100 is in the closed position. Support notch 146 may be formed in the inner surface of the base 104 within the enclosure 102. Passages 150A and 150B are connected through the side of the base 104 for gaseous input and fluid drainage, respectively. The passages 150A and 150B can be sealable. Notches 148 are formed in the upper inner surface of the base 104 for movement of the sealing element 116. Electrical connections 152 are shown connecting to the side of the base 104. The cell culture plate support 122 and access door 154 can form an access assembly 168 (FIG. 8). Access door 154 may have a handle 172. The access assembly 168 can also include a front plate 156 that sealably interfaces with a front portion 158 of the enclosure 102 of the incubator 100. The access assembly 168 may also include access track guides 166 to support the movement of the cell culture plate 114 and support in and out of the enclosure 102. The illustrated access assembly 168 has the cell culture plate support 122 mounted on the front plate 156 of the access door 154. Insulation panels 170 may be attached to the base 104.

Figure 9:
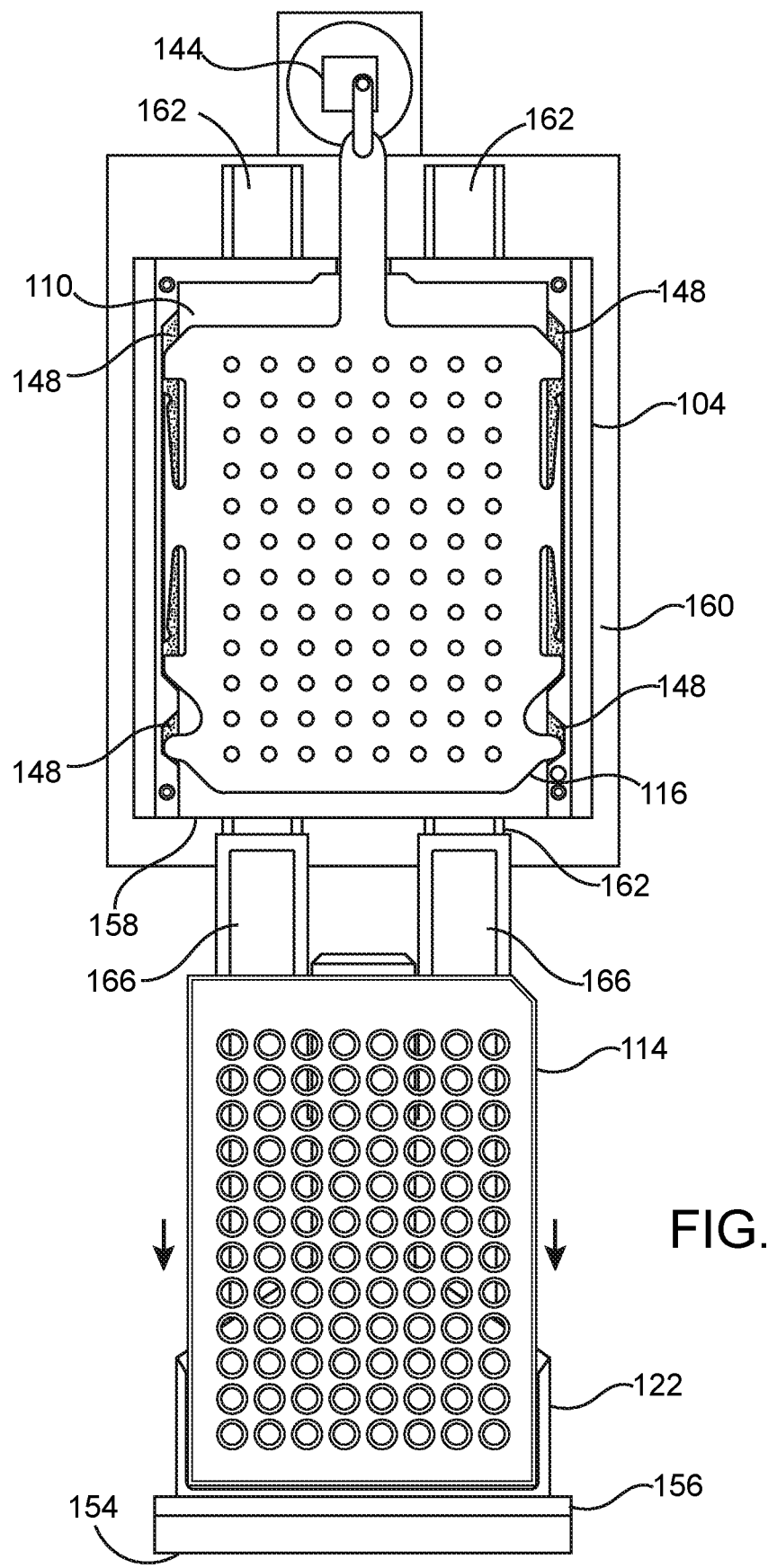
FIG. 9 illustrates a top view of a portion of an incubator in accordance with some embodiments.

The assembly 164 can be mounted on an enclosure support 160 that supports the enclosure 102. The enclosure support 160 can include tracks 162 that can allow the access assembly 168 to slide on the track guides 166 relative to the enclosure 102 between a closed position (FIG. 7) and an open position (FIGS. 8 and 9). The enclosure support 160 can also include legs 164 to further support the base 104, which may be adjustable.

FIG. 9 illustrates a top view of the incubator 100 and access door 154 in the open position. In this illustration, the extent of the tracks 162 is visible as tracks 162 extend beyond a rear side of the base 104, permitting the track guides 166 to fully slide and close the cell culture plate support 122 to rest within support notch 146. The tracks 162 are mounted on enclosure support 160. The cell culture plate support 122 is attached to front plate 156 of the access door 154, forming access assembly 168, and may further include track guides 166. Access door 154 may have a handle 172. Sealing element 116, attached to actuator 144 is located upon the base 104, fitting within notches 148 which permit the sealing element 116 to move when actuated. Within the internal chamber 110, support notch 146 in the base 104 is shown when the cell culture plate support 122 is not engaged (i.e. the access assembly is open). Notches 148 are shown in the upper inner surface of the base 104, which permit the sealing element 116 to move when actuated. Insulation panels 170 may be attached to the base 104.

Figure 10B:
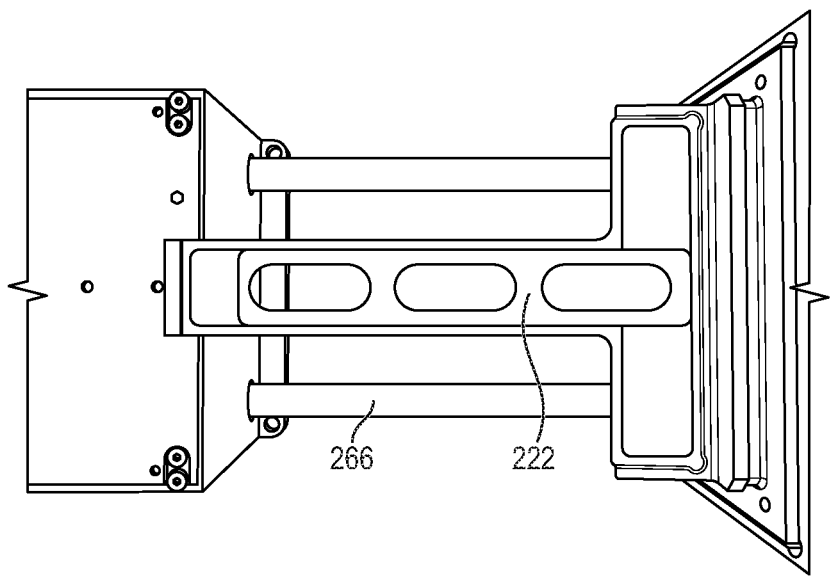
Figure 11A:
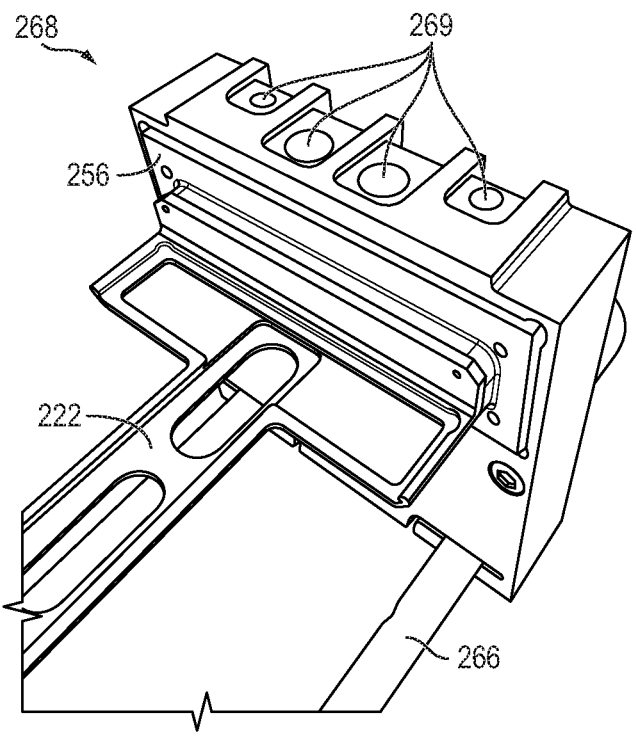
FIGS. 11A-11B illustrate views of a portion of a support for a cell culture plate of an incubator, in accordance with some embodiments.
Figure 11B:
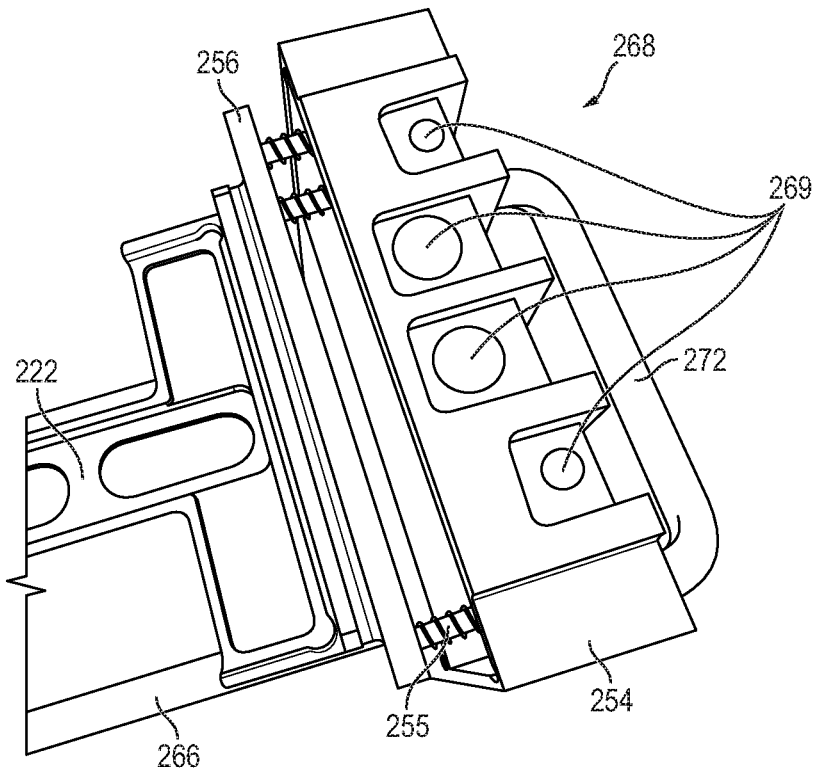
Figure 11C:
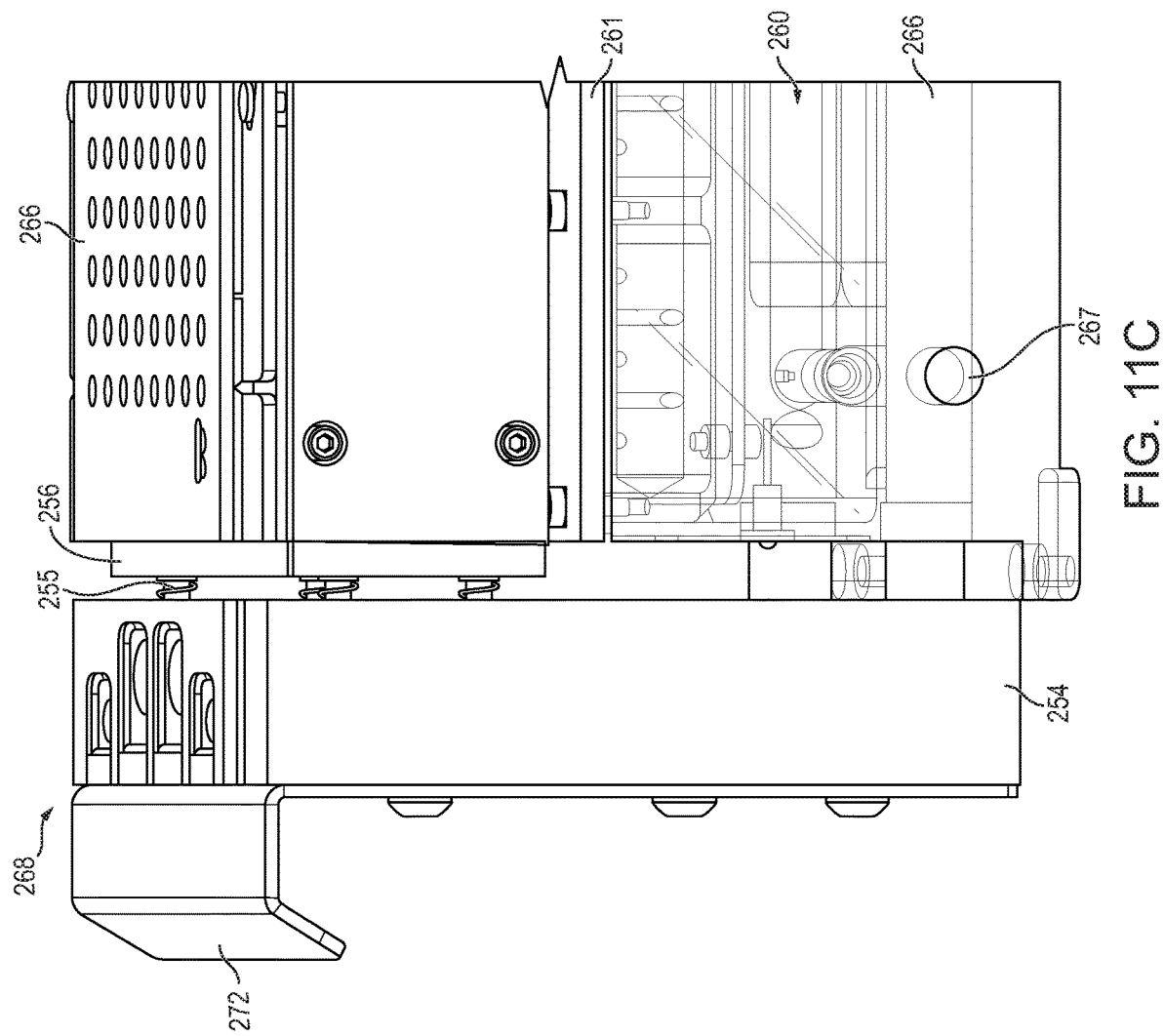
FIG. 11C illustrates a partial side view of an incubator, in accordance with some embodiments.

FIGS. 10A-10B illustrate a top view of an incubator with a support 222 for a cell culture plate in an open and a closed position, respectively, in accordance with some embodiments. FIG. 10A illustrates the support 222 with a different shape than the support 122. The support 222 can be moved by grabbing the handle 272 to slide the rails 266 to the open position shown in FIG. 10B. The support 222 can be positioned near the bottom of the enclosure to allow for air-space above the cell culture plate 114. Allowing air-space above the cell culture plate 114 can be important for maintaining a proper humidity level above the wells 120 of the cell culture plate 114 and avoiding evaporation of the culture medium contained within the wells 120 of the cell culture plate 114. The support 222 is attached to the access door 254 such that sliding the access door horizontally also moves the support 222 as shown in FIG. 10B. The support 222 can be attached directly or indirectly to access door 254. FIG. 10B shows the rails 266 with a cylindrical shape. The rails 266 can slide along a complimentary shaped opening in the enclosure support 260.

FIGS. 11A-11B illustrate views of a portion of a support 122 for a cell culture plate of an incubator in accordance with some embodiments. The support 122 is part of the access assembly 268. The access assembly 268 includes four openings 269 configured to hold vials or test tubes in the access door 254. The access assembly 268 includes a front plate 256. The access door 254 has a handle 272. The illustrated front plate 256 has a floating engagement with the access door 254 via the biased connections 255. The front plate 256 is directly attached to the support 222. The biased connections 255 are illustrated with a screw attached to the front plate 256 and a spring surrounding each of the screws to bias or press the front plate 256 relative to the access door 254. When the access assembly 268 is in the open position, the heads of the screws are retained on the C-bores of the access door 254. When the access assembly 268 is in the closed position the biased connections 255 can provide a force to the front plate 256 to secure the front plate 256 relative to the enclosure.

FIG. 11C illustrates a side view of an incubator in accordance with some embodiments. FIG. 11C illustrates the access assembly 268 in an almost closed position. FIG. 11C shows the biased connections 255 securing the front plate 256 against the enclosure. The rails 266 can be secured against a complementary connection 267, such as a flexible locking pin, within the enclosure support 260 in the closed position. FIG. 11C illustrates the front plate 256 against the enclosure and the rails 266 just prior to engagement of the complimentary connection 267 prior to clicking into the closed position. The biased connections 255 can also reduce the amount of abrupt motion experience by the support 222 and thus any well-plate supported by the support 222 as the access door 268 is opened or closed and locked into place. Reducing the abrupt motion can minimize and prevent splashing and sloshing of any fluid in the wells 120 of the cell culture plate 114 when the access door 254 is closed. In order to close the illustrated incubator, the rails access assembly 268 is advanced until the front plate 256 engages with the enclosure. Next, an additional force can be applied to further move the access assembly 268 and the rails 266 such that the rails are secured against a complementary connection 267 within the enclosure support 260 to enter the closed position. The biased connections 255 reduce or eliminate movement of the cell culture plate 120 caused by the force to advance the access assembly 268 after the front plate 256 is engaged with the enclosure to enter the closed position.

Figure 12A:
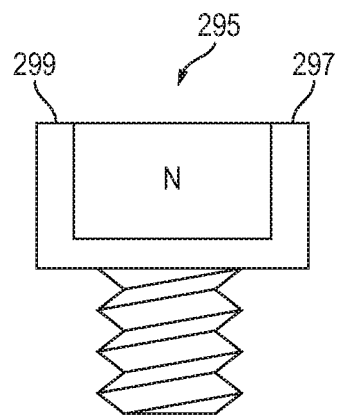
FIGS. 12A-12B illustrate a view of a magnet and a view of slide rails that can be used in embodiments of the incubators disclosed herein.
Figure 12B:
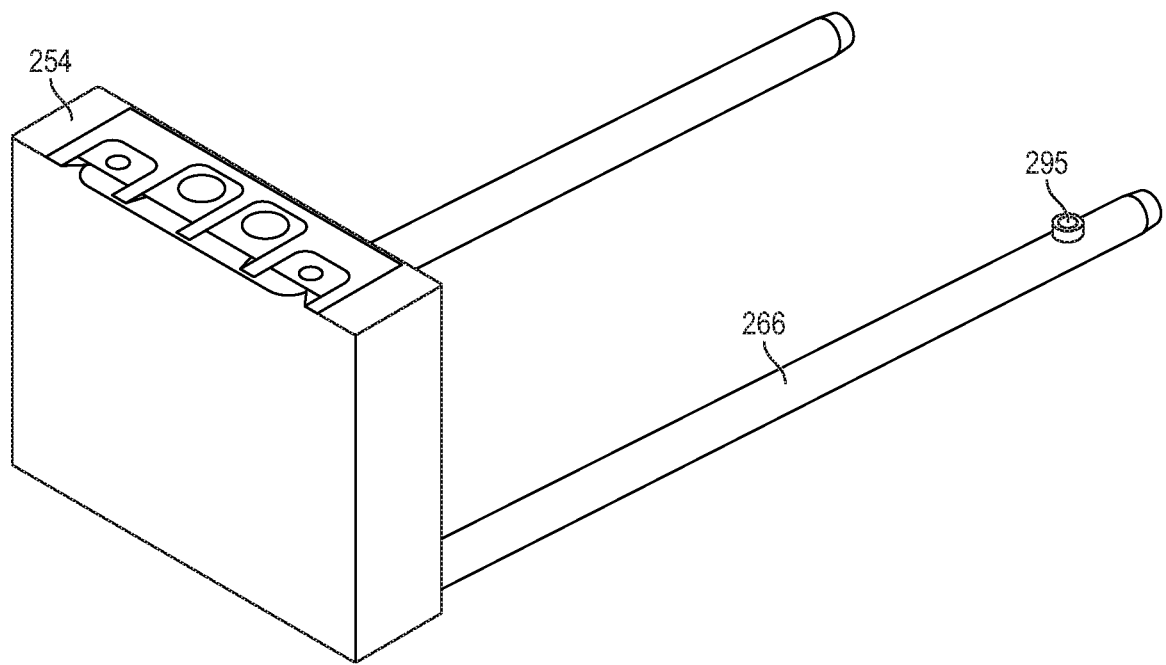
Figure 13:
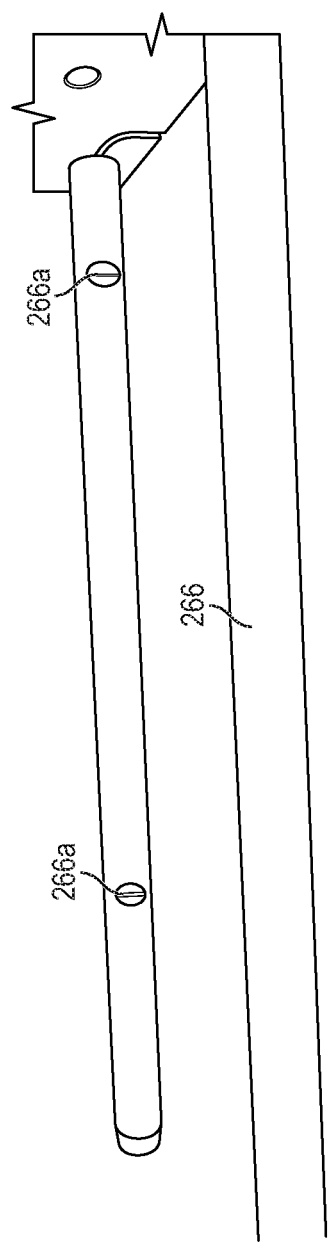
FIG. 13 illustrates an embodiment of rails on a access assembly of an incubator, in accordance with some embodiments.

The rails of the access assembly 168, 268 can include one or more stops or engagement surfaces to help hold the access assembly 168, 268 in one or more discrete positions such as open and closed position. FIGS. 12A and 12B illustrate a view of a magnet and a view of rails that can be used in embodiments of the incubators disclosed herein. A magnet assembly 295 is shown with a magnet 297 and a magnet housing 299. The magnet assembly 295 can be included within the rails 266. The magnet 297 within the magnet assembly 295 can engage with a complementary magnet within the enclosure support 260 to form a connection to hold the rails 266 in place at a designed location, such as the open or closed positions for the access assembly 268. In some embodiments the magnet 297 can engage with the door switch 273 (FIG. 16). FIG. 13 illustrates an embodiment of rails 266 that can be used in the embodiments of incubators described herein. FIG. 13 shows rails 266 with flat surfaces 266a that are designed to interface with a complementary connection 267, such as a flexible locking pin, within the enclosure support 260. The locking pins help to hold the access assembly 268 in open or closed positions.

FIG. 14 illustrates an exploded view of a portion of an incubator including an enclosure support 260 in accordance with some embodiments. The illustrated enclosure support 260 includes a heat transfer element 261. The heat transfer element 261 can provide heat to the bottom of the enclosure. The heat transfer element can be in contact with a circulated heating/cooling fluid, resistive heater or other heating/cooling device. The illustrated enclosure support 260 includes a gasket material 263. The gasket material 263 can prevent condensation or liquid from falling down into the enclosure support and contacting any of the electronic components with the enclosure support 260. The enclosure support can optionally include a drip tray or other drain to channel condensation and other liquid along a desired path to avoid or minimize condensation from contacting the electronic components. The enclosure support has electrical connections 252 that may be connected to heat transfer element 261 and other electronics in the incubator.

Figure 15:
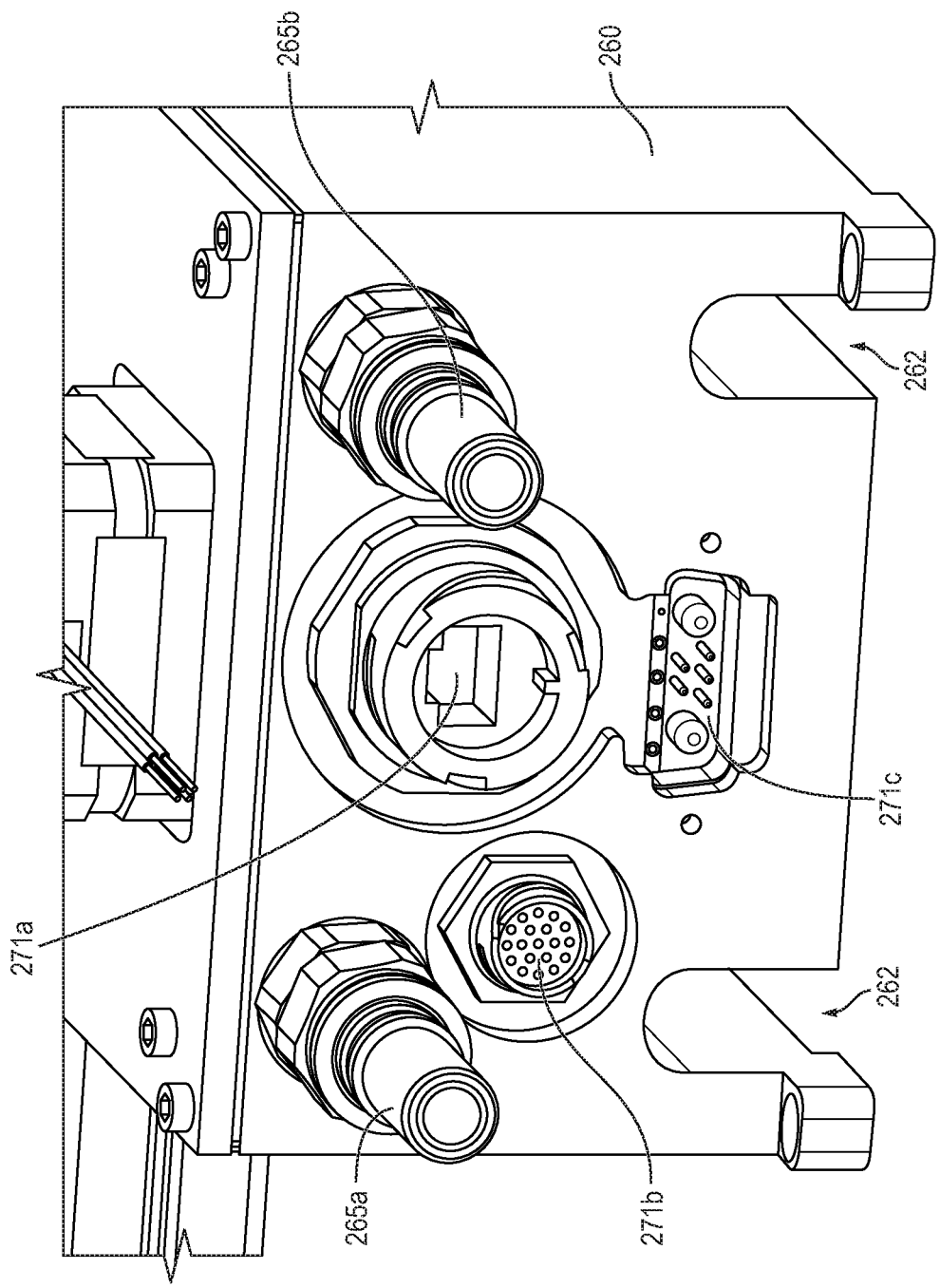
FIG. 15 illustrates an exterior portion of an incubator, in accordance with some embodiments.

FIG. 15 illustrates an exterior portion of an incubator in accordance with some embodiments. The enclosure support 260 can include tracks 262 that can allow the access assembly 268 to slide on the rails 266 relative to the enclosure between a closed position and an open position. The enclosure support 260 includes a heat exchange fluid inlet 265a and outlet 265b. The enclosure support 260 includes different electrical connection ports 271a, 271b, and 271c. For example, electrical connection port 271a is illustrated as an Ethernet port. The electrical connection ports 271a, 271b, and 271c can be used to control, monitor, and update software/firmware of the incubator.

FIG. 16 illustrates a side view of an incubator in accordance with some embodiments. The enclosure support 260 and access assembly 268 is illustrated in a closed position. The enclosure support 260 includes a door switch 273 that can mechanically, electrically, or magnetically engage with a portion of the rail 268 when the access assembly 268 is in the closed position. The door switch 273 can recognize when the access assembly 268 is in a closed position and transmit that information to a processor onboard the incubator.

Figure 17B:
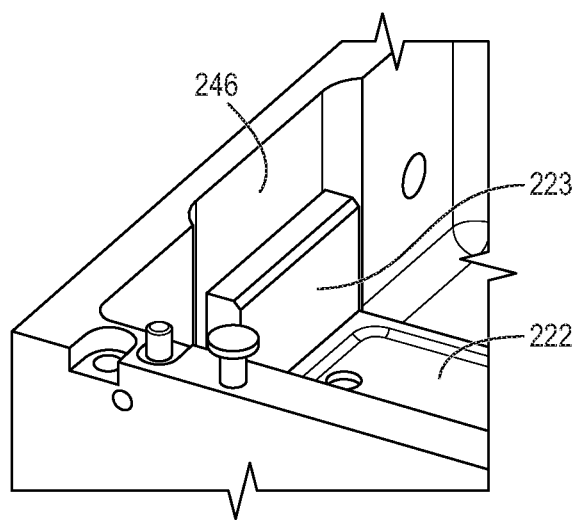

FIGS. 17A-17B illustrate an isometric view of an incubator with a support 222 for a cell culture plate in an open and a closed position, respectively, in accordance with some embodiments. The illustrated support 222 includes a distal lip 223 configured to engage an edge of the cell culture plate 114. The distal lip 223 can be supported by the resting support 246 when the support 222 is in the closed position. The distal lip 223 of the support 222 can also rest against a portion 247 of the enclosure as shown in FIG. 17A when in the open position to prevent vibration and motion of the support.

In FIGS. 1, 3, and 6-9, the figures show the sealing element 116, 216 having 96 openings 118, 218 which may be moved into register with 96 wells 120 of the cell culture plate 114, but other configurations are also envisioned. In some embodiments there may be a first set of openings 118, 218 that may have 96 openings, plus a second set of openings 118, 218 that may be moved into register with fewer than 96 of the wells 120 on the cell culture plate 114. As non-limiting examples, the second set may be moved to register with half of the 96 wells 120 or may be moved to be in register with 24 of the 96 wells 120. In some embodiments, there may further be a third set of openings 118, 218 on the sealing element 116, 216 which may be moved into register with fewer than all 96 wells 120 of the cell culture plate 114. As non-limiting examples, the third set of openings 118, 218 may be 48 openings that may be moved into register with half of the wells 120 or may be 24 openings that may be moved into register with a quarter of the wells 120. The third set of openings 118, 218 may move into register with wells 120 that are different from the wells 120 that may be accessed by use of the second set of openings 118, 218. When the second and third set of openings 118, 218 provide access to different wells 120, the wells 120 may be located on different halves or sides of the cell culture plate 114, may be physically alternating in location or may be located according to another preselected pattern.

In other embodiments, the first set of openings 118, 218 may be moved into register with fewer than all 96 wells 120 of the cell culture plate 114. Non-limiting examples include where the first set of openings 118, 218 may move into register with half or a quarter of the wells 120 of the cell culture plate 114. The sealing element 116, 216 may further have a second set of openings 118, 218 that may be moved into register with fewer than 96 of the wells 120 on the cell culture plate 114. As non-limiting examples, the second set may be moved to register with half of the 96 wells 120 or may be moved to be in register with 24 of the 96 wells 120. In some embodiments, there may further be a third set of openings 118, 218 on the sealing element 116, 216 which may be moved into register with fewer than all 96 wells 120 of the cell culture plate 114. As non-limiting examples, the third set of openings 118, 218 may be 48 openings that may be moved into register with half of the wells 120, or may be 24 openings that may be moved into register with a quarter of the wells 120. The first, second or third sets of openings 118, 218 may move into register with wells 120 that are different from the wells 120 that may be accessed by use of either of the other two sets of openings 118, 218, or may access overlapping locations of wells 120. The wells 120 may be located on different halves or sides of the cell culture plate 114, may be physically alternating in location or may be located according to another preselected pattern.

While FIGS. 1 and 7-9 illustrate a cell culture plate 114 having 96 wells 120, it is also envisioned that the lid 106, 206, sealing element 116, 216, PCB 132, 232, spacer 134 and the respective openings (112, 212, 138, 238, and optionally 142) thereof, can accommodate differently proportioned cell culture plates 114 and/or cell culture plates 114 having different numbers of wells 120 within them. In some embodiments, there may be 384 wells in the cell culture plate 114. When 384 wells 120 are present, the lid 106, 206 and lid assembly 108 components including the PCB 132, 232 and optional spacer 134 may have 384 openings or some subset thereof. When the cell culture plate 114 has 384 openings the sealing element 116, 216 may have 384 openings 118, 218 that can be moved into register with the wells 120, or may have fewer openings 118, 218 that can be moved into register with a subset of the wells 120. The sealing element 116, 216 may have additional sets of openings 118, 218 that may be configured as described above for a 96 cell culture plate 114 configuration, and may be configured in any similar combination. The cell culture plate 114 may also be configured to have 12 or 6 or fewer wells 120, and the lid 106, 206, sealing element 116, 216, PCB 132, 232, optional spacer 134 and the respective openings (112, 212, 138, 138, and optionally 142) thereof, may be configured to provide access to this smaller number of wells 120 and/or subsets thereof.

Any of the incubators 100 described above may have any suitable combination of sizes of openings 112, 212, 138, 238, and/or 142, and/or any of the additional components such as insulation, sensors, one or more controllers 174 (See FIG. 18), electrical connections 152, 252 heating and cooling devices, inlets for gas and for fluid drainage in any combination. The one or more controllers 174 may control the sealing element 116, 216, the temperature, relative humidity, and/or gaseous environment of the internal chamber 110, and/or the access assembly 168, 268.

In some embodiments, an incubator 100 includes an enclosure 102 having an internal chamber 110 configured to support a cell culture plate 114 comprising a plurality of wells 120, wherein the enclosure 102 has a plurality of openings provided by the openings 112 in the lid 106, 206 and openings (138, 238 and optionally 142) of the associated lid assembly 108. The openings in the enclosure (112, 212, 138, 238 and optionally 142) are configured to allow access to the wells 120 of the cell culture plate 114; and a sealing element 116, 216 configured to seal the plurality of openings in the enclosure 102, wherein the sealing element 116, 216 includes a first plurality of openings 118, 218 corresponding to at least a subset of the plurality of openings in the enclosure. The enclosure 102 may include a base 104 and a lid 106 where the base 104 and the lid 106 defines the internal chamber. In some embodiments, the internal chamber 110 has a volume of about 200 cm$^3$ to about 750 cm$^3$. In other embodiments, the internal chamber 110 has a volume of about 400 cm$^3$ to about 1,000 cm$^3$. The base 104 may be formed from a rigid material having a high thermal conductivity and low thermal capacitance. The lid 106 may be formed from an insulating plastic. The incubator 100 may include a printed circuit board (PCB) 132, 232. The PCB 132, 232 may be located between the sealing element 116, 216 and an internal surface of a top of the enclosure. PCB 132, 232 may include a plurality of openings 138, 238 in register with the plurality of openings passing through the enclosure. The PCB 132, 232 may include one or more sensors, which may be selected from the group consisting of: a temperature sensor, a humidity sensor, an oxygen sensor, and a carbon dioxide sensor. The incubator 100 may include a spacer 134, wherein the spacer 134 is located between the PCB 132, 232 and the sealing element 116. The spacer may 134 include a plurality of openings 142 in register with the plurality of openings passing through the enclosure and with the plurality of openings 138, 238 of the PCB. The spacer 134 may be configured to engage with the sealing element 116. In some embodiments, the incubator 100 has no spacer 134. The sealing element 116, 216 of the incubator 100 may be movable between a closed position where the sealing element 116, 216 occludes each of the plurality of openings in the enclosure and a first open position where the first plurality of openings 142 of the sealing element 116, 216 are in register with the at least a subset of the plurality of openings in the enclosure 102. The first plurality of openings 138, 238 of the sealing element 116, 216 may be the same as the number of openings in the enclosure 102. In some embodiments, the sealing element 116 has only a first plurality of openings 138. In some embodiments, the enclosure 102 and the sealing element 116, 216 have 96 openings 138. In other embodiments, the enclosure 102 and the sealing element 116, 216 have 384 openings. The sealing element 116, 216 may further include a second plurality of openings 138, 238, the second plurality of openings 138, 238 being different from the first plurality of openings 138, 238. The number of openings 138, 238 in the second plurality of openings 138, 238 in the sealing element 116, 216 may be one-half, one-third, or one-fourth the number of openings in the enclosure 102. Each opening of the plurality of openings in the enclosure may have a diameter of about 1 mm to about 10 mm or about 1 mm to about 5 mm. Each opening of the plurality of openings 138, 238 in the sealing element 116, 216 may have a diameter of about 1 mm to about 10 mm or about 1 mm to about 5 mm. The incubator 100 may include a first heating/cooling device engaged with the enclosure, the first heating/cooling device controlled by a temperature controller attached to the incubator. The first heating/cooling device may be selected from the group consisting of: a resistive heater, a fluid coil configured to circulate a heat exchange fluid, and one or more Peltier devices. The first heating/cooling device may directly contact an outer surface of the bottom of the enclosure. The first heating/cooling device may include a fluid coil. The incubator may include a second heating/cooling device, which may be located within the enclosure. The second heating/cooling device may be engaged with a top of the enclosure and may be controlled by a temperature controller attached to the incubator. The second heating/cooling device may be resistive heating elements 140 that are part of the PCB 132, and are located on a side of the PCB 132 facing the internal chamber of the enclosure. The second heating/cooling device may include a plurality of openings that are in register with the plurality of openings in the enclosure. The incubator 100 may include a controller 174, which may be a temperature controller configured to maintain a temperature of the internal chamber within a desired range by controlling the first and/or second heating/cooling device. The controller 174 may also control the sealing element 116, 216 relative humidity, gaseous environment of the internal chamber, and/or the access assembly 168. The incubator 100 may include a support 122, 222 for the cell culture plate 114. The support 122, 222 may be configured to slideably move relative to the enclosure 102 from a position within the enclosure 102 to a position outside of the internal chamber 110 of the enclosure 102. The incubator 100 may further include an access door 154, 254 attached to the support 122, 222 for the cell culture plate 114. The support 122, 222 and access door 154, 254 may form an access assembly 168, 268, including a front plate 156, 256 that sealably interfaces with a portion of the enclosure. The access assembly 168, 268 may be movably mounted on an enclosure support 160, 260 that supports the enclosure 102. The incubator 102 may further include at least one passage 150A in the enclosure configured for gas, where the at least one passage 150A may be located on a wall of the base 104 at the same height from a bottom of the base as the side of the cell culture plate 114.

Methods. Methods are also provided for using the incubators 100 disclosed herein. The methods can include moving a sealing element 116, 216 with a plurality of openings 118, 218 to an open position where the plurality of openings 118, 218 of the sealing element 116, 216 are in register with a first subset of openings of the plurality of openings (112, 212, 138, 238 and optionally 142) in the enclosure 102, as provided by the lid 106, 206 and associated lid assembly 108. The plurality of openings 118, 218 of the sealing element 116, 216 and the first subset of openings of the plurality of openings (112, 212, 138, 238 and optionally 142) in the enclosure 102 provide a first plurality of passages from an exterior of the incubator 100 to an internal chamber 110 of the enclosure 102. An import/export tip can be advanced through one or more of the first plurality of passages between the exterior of the incubator 100 and the internal chamber 110 of the enclosure 102. The methods can include collecting or depositing a material within the internal chamber 110 of the enclosure 102 via the import/export tip. The first subset of openings can include all of the openings of the plurality of openings in the enclosure, or less than all (e.g., ½, ⅓, ¼, or less).

Material that may be collected from, withdrawn from, or deposited to a well 120 of a cell culture plate 114 within the internal chamber 110 of the enclosure 102 may include micro-objects, (which may further include one or more biological micro-objects), proteins, nucleic acids, lipids or other cellular components found within or secreted by biological micro-objects, fluids such as but not limited to culture media, solvents such as but not limited to dimethylsulfoxide or ethyl alcohol, surfactants, assay reagents, or reagents such as permeabilization reagents, labelling reagents, fusion reagents, and the like, and the waste products derived from culturing or reaction of the reagents with a component of the material being withdrawn or deposited. In various embodiments, the material may contain at least one biological cell which may be maintained or expanded in the well 120 of the culture plate 114. In other embodiments, the material may not have a cell present but may contain the derived proteins, nucleic acids, lipids or other cellular components described above which may be suitable for holding under prescribed temperature and/or humidity conditions. In yet other embodiments, the material that is deposited to a well may be one or more reagents to assay, fix, transfect or stabilize biological micro-objects or components found within or secreted by the biological micro-objects. In yet other embodiments, the material that is deposited to or withdrawn from a well 120 can include a micro-object such as a bead, and the like. The bead may include a protein, saccharide, and/or a label (where the label may be detected colorimetrically, fluorescently, or luminescently). In some embodiments, the material may include more than one type of material described above.

Collecting or depositing the material includes collecting or depositing the material within a well 120 of a cell culture plate 114 within the internal chamber 110 of the enclosure 102. In some embodiments collecting or depositing the material can be done with an import/export tip. In some embodiments the import/export tip can include a plurality of tips. In some embodiments the plurality of tips of the import/export tip can simultaneously collect or deposit the material from a plurality of the wells 120 of the cell culture plate 114 within the incubator 100. The import/export tip(s) can be withdrawn through the one or more of the passages between the exterior of the incubator 100 and the internal chamber 110 of the enclosure 102 after collecting or depositing the material. Collecting or depositing the material can be performed robotically. In various embodiments, the import/export tip may withdraw/deposit material at a rate of about 0.01 µl, 0.02 µl, 0.05 µl, 0.1 µl, 0. µl, 0.5 µl, 1 µl, 2 µl, 3 µl, 4 µl, 5 µl, 6 µl, 7 µl, 8 µl, 9 µl, 10 µl, 11 µl, 12 µl, 15 µl, µl, 20 µl, 22 µl, 24 µl, 25 µl, 27 µl, 29 µl, 30 µl per sec, or any range defined by two of the foregoing values.

Methods are also provided for agitating the contents of a well 120 in the cell culture plate 114 in conjunction with collecting or depositing the material in the well 120. In some embodiments, a mixing tip is inserted through one or more of the passages between the exterior of the incubator 100 and the internal chamber 110 of the enclosure 102. The passages are created by bringing an opening 118, 218 of the sealing element 116, 216 into register with an opening (112, 212, 138, 238 and optionally 142) in the enclosure 102 of the incubator 100. The mixing tip may provide agitation within fluid present in the well 120 by rotating, vibrating, or otherwise moving about, injecting fluid (such as culture medium), injecting gas, or the like. The agitation may provide more uniform samples of the material present in the well or may provide more uniform composition of a liquid medium within a well prior to adding material to it, or prior to adding another composition containing either a material of same or differing type (e.g. a biological micro-object of a different type or a micro-object such as a bead having a label or a reagent bound to it) or other chemical components that may be desired. In some embodiments, the mixing tip may withdraw an aliquot of fluid from the well 120 and reinject it to mix the contents of the well 120 before material is added to the well 120 or is withdrawn from the well 120 by the import/export tip (not shown). In some embodiments, the mixing tip may withdraw about 10 µl to about 50 µl of fluid from the well and reinject it to the well at a rate of about 1 µl, 2 µl, 3 µl, 4 µl, 5 µl, 6 µl, 7 µl, 8 µl, 9 µl, 10 µl, 11 µl, 12 µl, 15 µl, 17 µl, 20 µl, 22 µl, 24 µl, 25 µl, 27 µl, 29 µl, or about 30 µl per sec. In some embodiments, the mixing tip withdraws about 10 µl, 11 µl, 12 µl, 13 µl, 14 µl, 15 µl, 16 µl, 17 µl, 18 µl, 19 µl, 20 µl, 21 µl, 22 µl, 23 µl, 24 µl, 25 µl, 26 µl, 27 µl, 28 µl, 29 µl, 30 µl, 35 µl, 40 µl, 45 µl, or about 50 µl of fluid to mix the contents of the well before withdrawing from or depositing to a well 120.

The methods also provide for cleaning steps before and/or after each use of the import/export tip and/or the mixing tip. The cleaning step can include manual wiping with a tissue or cloth, a water/bleach flush over the tip, water/bleach dip, ultrasonic cleaning or dip into ozonized water.

The sealing element 116, 216 can be moved to a closed position such that the sealing element 116, 216 occludes the plurality of openings (112, 212, 138, 238 and optionally 142) in the enclosure 102. Moving the sealing element 116, 216 between the open position and closed position can include sliding the sealing element 116, 216 relative to the enclosure 102. The sealing element 116, 216 can be moved between the open and closed positions by actuating a sealing element actuator 144. For example, a motor or rotary solenoid can be used to actuate the sealing element actuator 144. The sealing element 116, 216 can be in the open position for an amount of time which is sufficiently short so as to prevent a carbon dioxide content and/or a humidity of air present in the internal chamber 110 from equilibrating with a carbon dioxide content and/or a humidity of air surrounding the incubator 100.

Methods are also provided for moving the sealing element 116, 216 between the closed position and a plurality of open positions. The methods can include moving the sealing element 116, 216 to a first open position in which a first plurality of openings 118, 218 in the sealing element 116, 216 are in register with a first subset of the plurality of openings (112, 212, 138, 238 and optionally 142) in the enclosure 102. In some embodiments, the number of the plurality of openings 118, 218 in the sealing element 116, 216 can be the same as a number of the plurality of wells 120 in the cell culture plate 114. In some embodiments, a number of openings 118, 216 in the first plurality of openings 118, 218 in the sealing element 116, 216 is equal to or less than one-half, one-third, one-fourth, one-sixth, or one-twelfth a number of the plurality of wells 120 in the cell culture plate 114.

The methods can include moving the sealing element 116, 216 to a second open position in which a second plurality of openings 118, 218 in the sealing element 116, 216 are in register with a second subset of the plurality of openings (112, 212, 138, 238 and optionally 142) in the enclosure 102 and all other openings of the plurality of openings (112, 212, 138, 238 and optionally 142) in the enclosure 102 are occluded. The second plurality of openings 118, 218 in the sealing element 116, 216 and the second subset of the plurality of openings (112, 212, 138, 238 and optionally 142) in the enclosure 102 can provide a second plurality of passages from an exterior of the incubator 100 to the internal chamber 110. In various embodiments, a number of openings 118, 218 in the second plurality of openings 118, 218 in the sealing element 116, 216 is equal to or less than one-half, one-third, one-fourth, one-sixth, or one-twelfth a number of the plurality of wells 120 in the cell culture plate 114.

The methods can also include moving the sealing element 116, 216 to a third open position in which a third plurality of openings 118, 218 in the sealing element 116, 216 are in register with a third plurality of openings (112, 212, 138, 238 and optionally 142) in the enclosure 102 and all other openings of the plurality of openings (112, 212, 138, 238 and optionally 142) in the enclosure 102 are occluded. The third plurality of openings 118, 218 in the sealing element 116, 216 and the third subset of the plurality of openings (112, 212, 138, 238 and optionally 142) in the enclosure 102 can provide a third plurality of passages from an exterior of the incubator 100 to the internal chamber 110. In some embodiments, a number of openings in the third plurality of openings 118, 218 in the sealing element 116, 216 is equal to or less than one-half, one-third, one-fourth, one-sixth, or one-twelfth a number of the plurality of wells 120 in the cell culture plate 114. In various embodiments of the method, the first plurality of the openings 118, 218 in the sealing element 116, 216, the second plurality of openings 118, 218 in the sealing element 116, 216 and the third plurality of openings 118, 218 in the sealing element 116, 216, if present, are non-overlapping. In some embodiments first plurality of the openings 118, 218 in the sealing element 116, 216, the second plurality of openings 118, 218 in the sealing element 116, 216, and the third plurality of openings 118, 218 in the sealing element 116, 216, if present, when in register with the openings (112, 212, 138, 238 and optionally 142) in the enclosure 102, provide access to wells 120 in different portions of the cell culture plate 114. In some embodiments, the actuator 144 may move the sealing element 116, 216 from the closed position to the first open position and from the closed position to the second open position. In some embodiments, the actuator 144 may further move the sealing element 116, 216 from the closed position to the open position. In other embodiments, the actuator 144 may move the sealing element 116, 216 from the closed position to any of the first open position, second open position and/or the third open position, if present.

The methods can also include measuring one or more of a temperature, a humidity, and a carbon dioxide content of the internal chamber 110 of the enclosure 102 and controlling one or more of the temperature, humidity, and carbon dioxide content of the internal chamber 110 of the enclosure 102. Controlling the temperature can include heating or cooling the internal chamber 110 of the enclosure 102. Controlling the humidity can include providing a humidity source to the internal chamber 110 of the enclosure 102. Controlling the carbon dioxide content can include providing a carbon dioxide source to the internal chamber 110 of the enclosure 102.

In some embodiments, the pressure of the internal chamber 110 of the incubator 100 can be maintained at a desired range while the sealing element 116 is in the closed position. The sealing element 116, when in the closed position, can be capable of maintaining a pressure within the internal chamber 110 of the enclosure 102 between about 0.0005 psi to about 0.0100 psi above ambient pressure or any of the pressure ranges disclosed herein. For example, the pressure of the internal chamber 110 can be maintained between about 0.0005 psi to about 0.01000 psi above ambient pressure. In some embodiments, the pressure of the internal chamber 110 may be maintained about 0.0005 psi, 0.0010 psi, 0.0015 psi, 0.0020 psi, 0.0025 psi, 0.0030 psi, 0.0035 psi, 0.0040 psi, 0.0045 psi, 0.0050 psi, 0.0055 psi, 0.0060 psi, 0.0065 psi, 0.0070 psi, 0.0075 psi, 0.0080 psi, 0.0085 psi, 0.0090 psi, 0.0095 psi, or about 0.0010 psi. Clean rooms typically use a positive pressure of about 0.0072 psi or less. In some embodiments the pressure of the internal chamber 110 can be maintained less than about 0.0072 psi above ambient pressure. In some embodiments the pressure of the internal chamber 110 can be maintained above about 0.0072 psi above the ambient pressure.

A purge gas can be provided to maintain the pressure in some embodiments. The methods can include providing the purge gas to the internal chamber 110 of the enclosure 102 whereby, when the sealing element 116, 216 is in the closed position and the support 122, 222 for the cell culture plate 114 is positioned inside the internal chamber 110 of the enclosure 102, the pressure within the internal chamber 110 of the enclosure 102 is maintained between about 0.0005 psi to about 0.0100 psi above ambient pressure. The purge gas can include one or more of carbon dioxide, oxygen, nitrogen, and noble gases. In some embodiments, the purge gas may include about 5% carbon dioxide by volume.

In some embodiments the pressure can be maintained with the purge gas such that a desired flow rate of purge gas is achieved through the openings. In some cases, the flow rate can be less than or about 10 liters per hour, 9 liters per hour, 8 liters per hour, 7 liters per hour, 6 liters per hour, 5 liters per hour, 4 liters per hour, 3 liters per hour, 2 liters per hour, 1 liter per hour, or any range defined by two of the foregoing values. The flow rate may be more than about 0.5 liter per hour. In some embodiments the flow rate can be about 1 liter/hour to about 10 liters/hour.

In some embodiments a positive pressure can be maintained within the internal chamber 110 when the sealing element 116, 216 is in the open position. For example, the purge gas can be provided when the sealing element 116, 216 is in the open position to decrease the likelihood of contamination.

The cell culture plate 114 can be provided to the incubator 100 by sliding the support to withdraw the support from the internal chamber 110 of the enclosure 102 to a position outside of the internal chamber 110 of the enclosure 102 followed by placing the cell culture plate 114 on the support while the support is in the position outside of the internal chamber 110 of the enclosure 102. Placing the cell culture plate 114 can done by a human operator or a robotic tool. After placing the cell culture plate 114 on the support 122, 222, the support 122, 222 can slide to a position inside the internal chamber 110 of the enclosure 102 and thereby moving the cell culture plate into the internal chamber 110 of the enclosure 102. Sliding the support 122, 222 can include sliding an access door 154, 254 attached to the support for the cell culture plate 114. Sliding the support 122, 222 can include sliding the support along one or more tracks 162, 262 on an enclosure support 160, 260 of the incubator 100. Sliding the support 122, 222 can be done by a human operator or a robotic tool. After loading the cell culture plate 114 within the enclosure 102 an environment within the internal chamber 110 of the enclosure 102 can be established to support a material supported by the cell culture plate 114.

The cell culture plate 114 can be removed from the support for the cell culture plate 114 similarly to the loading steps described above. The support 122, 222 for the cell culture plate 114 can be accessed by sliding the support 122, 222 from the internal chamber 110 of the enclosure 102 to the position outside of the internal chamber 110 of the enclosure 102 and thereby withdrawing the cell culture plate 114 from the internal chamber 110 of the enclosure 102. Sliding the support 122, 222 can be done by sliding an access door 154, 254 attached to the support 122, 222. In some embodiments sliding the support 122, 222 can be done by a human operator. In some embodiments sliding the support 122, 222 can be done robotically, such as by a robotic tool. After the cell culture plate 114 is at the position outside of the internal chamber 110 of the incubator 100 the cell culture plate 114 can be removed from the support. Removal can be done by a human operator or a robotic tool.

In various embodiments, methods are provided to deliver one or more samples containing material to one or more wells 120 of the cell culture plate 114 contained within the well plate incubator 100, where the samples may be obtained from a macroscale cell culture apparatus, a microfluidic device and/or an analytical instrument. In some embodiments, the material may include a biological micro-object capable of being maintained and/or expanded. The sample containing the biological micro-object may be provided such that the biological micro-object is isolated away from other biological micro-objects that may be different from the biological micro-object or may be simply selected to be a single representative of a desired set of biological micro-objects present in the macroscale cell culture apparatus, microfluidic device and/or analytical instrument. In some embodiments, a single biological micro-object delivered within the material may be expanded to form a clonal population within the continuous access cell culture incubator. In some embodiments, a sample obtained from a macroscale cell culture apparatus may provide samples having biological micro-objects which may or may not be already sorted. The microfluidic device and/or analytical instrument from which samples are obtained may sort biological micro-objects, may provide dissociated biological micro-objects, or may have provided chemical or other treatment to the biological micro-object(s) delivered to the cell culture plate, to name some non-limiting exemplars.

Material may be delivered to a well 120 of the cell culture plate 114 that already contains media or other reagents. In some embodiments, the cell culture plate 114 of the continuous access incubator 100 may contain reagents to provide a treatment to a cell delivered to a well therein. For example, lysis reagents may be present or a fluidic medium may be present which will prepare a cell for further processing such as freezing, lysis or permeabilization.

In other embodiments, methods are provided to deliver a sample containing a biological micro-object withdrawn from a well in the cell culture plate within the continuous access incubator to a macroscale cell culture apparatus, a microfluidic device (which may be a nanofluidic device), an analytical instrument, or to a storage device. The biological micro-object may have been cultured (i.e. grown under suitable conditions) for a preselected period of time before being withdrawn for delivery to a macroscale cell culture apparatus, a microfluidic device or an analytical instrument. In other embodiments, the biological micro-object may be treated while present in the continuous access incubator to permeabilize a cell present in the biological micro-object or may be lysed for further analysis in a microfluidic device or analytical instrument, to name two non-limiting examples. In some embodiments, the biological micro-object may be treated to be stabilized for analysis or for storage. One non-limiting example includes treating the biological micro-object with suitable media to stabilize for freezing and long term storage.

In some embodiments methods for accessing an internal chamber 110 of an incubator 100 are provided. The incubator 100 can include an enclosure 102 having a plurality of openings and a sealing element 116, 216 having more than one plurality of openings 118, 218. Each plurality of openings 118, 218 in the sealing element 116, 216 can correspond to at least a subset of the plurality of openings in the enclosure 102. The methods can include moving the sealing element 116, 216 to a first open position and thereby bringing a first plurality of openings 118, 218 in the sealing element 116, 216 into register with a first subset of the plurality of openings in the enclosure 102. The first plurality of openings 118, 218 in the sealing element 116, 216 and the first subset of openings in the plurality of openings in the enclosure providing, when in register, a first plurality of passages from an exterior of the incubator 100 to the internal chamber 110 of the enclosure 102. The methods can include advancing an import/export tip through one or more of the first plurality of passages between the exterior of the incubator 100 and the internal chamber 110 of the enclosure 102. The methods can include collecting or depositing a material with the import/export tip within the internal chamber 110 of the enclosure 102. The methods can further include moving the sealing element 116, 216 to a closed position, and thereby occluding each of the plurality of the openings in the enclosure 102.

When the sealing element 116, 216 is in the open position, the first plurality of openings 118, 218 in the sealing element 116, 216 can be configured to be in register with a first subset of a plurality of wells 120 in the cell culture plate 114. In some embodiments a number of the plurality of openings 118, 218 in the sealing element 116, 216 is the same as a number of the plurality of wells 120 in the cell culture plate 114. In some embodiments a number of the plurality of openings 118, 218 in the sealing element 116, 216 is equal to or less than one-half, one-third, one-fourth, one-sixth, or one-twelfth a number of the plurality of wells 120 in the cell culture plate 114.

The methods can further include moving the sealing element 116, 216 to a second open position, thereby bringing a second plurality of openings 118, 218 in the sealing element 116, 216 into register with a second subset of the plurality of openings in the enclosure 102. The second plurality of openings 118, 218 in the sealing element 116, 216 and the second subset of the plurality of openings in the enclosure 102, when in register, can provide a second plurality of passages from an exterior of the incubator 100 to the internal chamber 110 of the enclosure 102. In some embodiments when the sealing element 116, 216 is in the second open position, all openings of the plurality of openings in the enclosure 102 other than the second subset of openings are occluded by the sealing element 116, 216.

The methods can further include moving the sealing element 116, 216 to a third open position, thereby bringing a third plurality of openings 118, 218 in the sealing element 116, 216 into register with a third subset of the plurality of openings in the enclosure 102. The third plurality of openings 118, 218 in the sealing element 116, 216 and the third subset of the plurality of openings in the enclosure 102, when in register, can provide a third plurality of passages from an exterior of the incubator 100 to the internal chamber 110 of the enclosure 102. In some embodiments when the sealing element 116, 216 is in the third open position, all openings of the plurality of openings in the enclosure 102 other than the third subset of openings are occluded by the sealing element 116, 216.

Systems. Systems are also provided including the well plate incubators 100 described herein. In some embodiments, a system 200 for incubation while providing continuing access for import/export is provided. A schematic diagram of one exemplary system is shown in FIG. 18. The systems 200 can include the well plate incubator 100, a robotic sampling component (including sampling drive controller 178 and sampling motors 182) configured to access the well plate incubator 100 to collect or deposit samples with an internal chamber of the well plate incubator, and at least one controller. In some embodiments, the incubator 100 includes controller 174, while in other embodiments, incubator controller 174 may be part of the system 200. In some embodiments, sampling drive controller 178 and pump controller 180 may be distinct controllers or may be part of the same controller. In any case, any of the controllers, including 174, 178 and/or 180, may be instructed by the control software 176. The controller 174 may be instructed by the control software 176 to open a plurality of passages from an exterior of the incubator 100 to the internal chamber of the enclosure. The controller 174 may be instructed by the control software 176 to control the robotic sampling component to access, via the plurality of passages, a plurality of wells 120 of a well plate 114 contained within the internal chamber 102 of the enclosure 102. The controller 174 may be instructed by the control software 176 to close the plurality of passages. The system 200 can be configured to maintain the internal chamber 110 of the enclosure 102 under positive pressure by instructing controller 174. Additionally, sampling drive controller 178 and pump controller 180 can be configured to control the motors 182 of the robotic sampling component and pumps 184 of a hydraulic component (including pump controller 180 and pumps 184) respectively of system 200, activating the import/export tip 186 to withdraw material from one of the plurality of wells 120 of the well plate. The controllers 178 and 180 can be configured to control the robotic sampling component/hydraulic component of system 200 to deliver the withdrawn material to another apparatus which may be external to the system 200. In some embodiments, the apparatus to which withdrawn material is delivered may be included as an additional component of system 200 and the control software 176 may instruct the additional apparatus as well. In some embodiments, an apparatus to which material withdrawn from the incubator 100 by import/export tip 186 may be delivered may be a microfluidic device 190. In some embodiments, the microfluidic device 190 may be a nanofluidic device. In other embodiments, material withdrawn from the incubator 100 via import/export tip 186 may be delivered via the robotic sampling component/hydraulic component of system 200 to an analytical instrument 192. Materials cultured in the system or delivered to the incubator of the system 200 may be any suitable materials as described herein and may include micro-objects and/or biological micro-objects. In some embodiments, biological micro-objects are cultured, imported and/or exported in system 200. Some non-limiting examples of suitable analytical instruments to which material may be delivered include sequencing instrumentation and sample prep therefor, assay instrumentation, mass spectrometry and sample prep therefor, and storage devices and stabilization prep therefor. In yet other embodiments, material withdrawn from the incubator 100 via import/export tip 186 may be delivered via the robotic sampling component to a macroscale cell culture apparatus 194.

The control software 176 can instruct the sampling drive controller 178 and/or pump controller 180 to control the robotic sample component and/or hydraulic component to deliver one or more samples of material to one or more wells 120 of the well plate contained within the well plate incubator 100. The one or more samples of material can be obtained from a macroscale cell culture apparatus 194, a microfluidic device (which may be a nanofluidic device) 190 or an analytical instrument 192. The macroscale cell culture apparatus 194 may include cell culture plates, flasks or reactors. Microfluidic devices 190, which include nanofluidic devices, include but are not limited to, droplet generation devices, microfluidic cell sorting and/or cell culturing devices. Analytical instruments 192 from which one or more samples of material may be obtained can include cell sorting instruments such as a flow cytometer, cell dissociation apparatuses, and cell storage apparatuses as non-limiting examples.

The system 200 may further include a mixing tip 188, which may be part of the hydraulic component. The mixing tip 188 may also access an opened passage to a well 120 having contents present in the cell culture plate 114 to mix the contents of the well 120 prior to import and/or export to/from the well 120. The action of mixing tip 188 may be controlled by controller 180. The mixing tip may rotate, vibrate, or otherwise move about, inject gas or liquid to effect mixing, or the like. In some embodiments, the control software 176 of system 200 may control the mixing tip 188 to withdraw an aliquot of fluid from the well 120 and reinject it to mix the contents of the well 120 before material is added to the well 120 or is withdrawn from the well 120 by the import/export tip 186. In some embodiments, the system may control the mixing tip to withdraw about 10 µl to about 50 µl of fluid from the well and reinject it to the well at a rate of about 1 µl, 2 µl, 3 µl, 4 µl, 5 µl, 6 µl, 7 µl, 8 µl, 9 µl, 10 µl, 11 µl, 12 µl, 15 µl, 17 µl, or about 20 µl/sec. In some embodiments, the mixing tip withdraws about 10 µl, 11 µl, 12 µl, 13 µl, 14 µl, 15 µl, 16 µl, 17 µl, 18 µl, 19 µl, 20 µl, 25 µl, 30 µl, 35 µl, 40 µl, 45 µl, or about 50 µl of fluid to mix the contents of the well before withdrawing from or depositing to a well 120.

The import/export tip 186 of system 200 may be connected to tubing (not shown) that can connect the incubator 100 to a microfluidic device 190, a macroscale cell culture apparatus 194, or an analytical instrument 192. If connected to tubing for import and/or export of biological material, the tubing may be made of material suitable for autoclaving or may be disposable. The tubing typically is made of a hydrophobic material. In some embodiments, the tubing may be made of Teflon™ (polytetrafluoroethylene) or PEEK (polyetheretherketone). The Teflon™ tubing may have a 1/16" outer diameter, with a 1/32" inner diameter. PEEK tubing may have a 1/32" outer diameter with a 0.015" inner diameter. The latter dimensions may be used for imports/exports of material from a 384 well plate. In various embodiments, the system may control the import/export tip to withdraw/deposit material at a rate of about 0.01 µl, 0.02 µl, 0.05 µl, 0.1 µl, 0.2 µl, 0.5 µl, 1 µl, 2 µl, 3 µl, 4 µl, 5 µl, 6 µl, 7 µl, 8 µl, 9 µl, 10 µl, 11 µl, 12 µl, 15 µl, 17 µl, 20 µl, 22 µl, 24 µl, 25 µl, 27 µl, 29 µl, 30 µl per sec, or any range defined by two of the foregoing values.

The robotic sampling component may be selected from but not limited to a linear stages robot, an xyz robot, or a Selective Compliance Assembly/Articulated Robot Arm (SCARA) robotic sampler. The robotic sampling component may direct the import/export tip to deposit/withdraw material to/from the wells 120 of the cell culture plate 114 within the incubator 100.

EXAMPLES

Example 1: CHO Cell Viability in a Well Plate Incubator

Materials: CHO—S cells were obtained from Fisher Scientific (Invitrogen™ Freestyle™ CHO—S cells, catalog # R80007). The cultures were maintained by seeding at $2\times10^5$ viable cells/ml and incubating at 37° C., using 5% carbon dioxide in air as the gaseous environment. Cells were split every 2-3 days.

Culture Medium: Freestyle™ Expression Medium (ThermoFisher Scientific, catalog #12651014), an animal origin-free, chemically defined, protein-free medium, was used. It was supplemented with HT Supplement from Gibco (Cat #11067-030) and L-Glutamine 200 mM from Gibco (Cat #25030-081).

Incubator: Manufactured by Berkeley Lights, Inc., includes a lid, shutter, and temperature and environment inputs as described above. Throughout the experiment, the lid was heated to 38° C., the enclosure surrounding the well plate was heated at 37° C., and the shutter was closed. Atmosphere was air supplemented with 5% $CO_2$, and flow rate into the incubator was 10 L/hr for each incubator. The gas mixture was humidified to a 90% relative humidity prior to entry into the incubator.

Control Incubator: The control incubator is commercially available (Heracel™ VIOS 160i $CO_2$ Incubator). The control incubator was operated according to manufacturer operating directions. The atmosphere was air supplemented with 5% $CO_2$, and the temperature was maintained at 37° C.

Well Plates: 96-well flat-bottom well plates with low evaporation lids, non-tissue culture treated were used (Falcon, Cat #351172).

Viability Assay: Cell Titer Glo Assay was obtained from Promega (Cat # G7572), and luminescence was measured using an EnVision Xcite Multilabel Plate Reader from PerkinElmer (Cat #: 2104-002A).

For each well plate, target seeding of cells was 20 cells per well, except for H12 which was maintained empty. Loaded well plates were placed within the test and control incubators. A total of 4 well plates were incubated in the test incubator and a total of 10 well plates were incubated in the control incubator for the entire experimental period. After culturing for 24 h in the test incubator, the test incubator well plates were transferred to the commercial incubator. All culture plates were incubated for a further 7 days.

At the end of the eighth day after seeding, samples were taken from each well of each incubator plate and individually subjected to the Cell Title Glo Assay, which was performed according to manufacturer directions. The assay generates a quantifiable fluorescent signal in proportion to ATP present, where ATP is used as a marker of cell metabolic activity. The raw fluorescence amplitude (Data not shown) for each well was normalized against a standard curve according to the manufacturer's directions, and the number of cells was calculated therefrom. From the calculated cell number, cell divisions per well were calculated.

Figure 19:
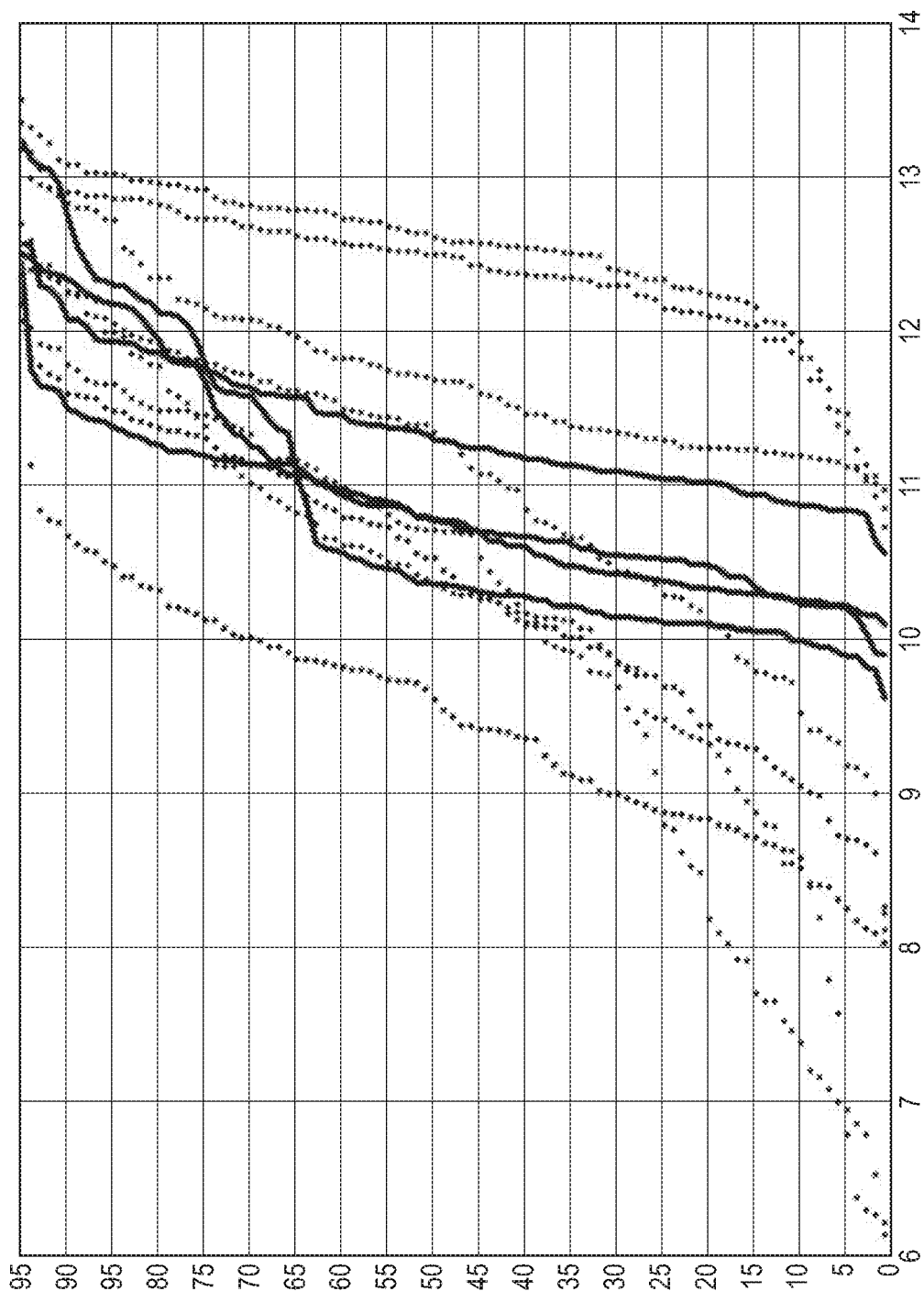
FIG. 19 is a graph of cell viability data obtained from cells cultured in an incubator of the invention during the first 24 hours after seeding (solid lines) and cells cultured entirely in a conventional incubator (dotted lines).

The number of cell divisions in each well of a well plate was graphed (shown in FIG. 19), one curve for each well plate. Data for each of the four well plates incubated in the test incubators is represented by the curves (heavy solid line) and data from the well plates incubated entirely in the control incubator is represented by curves having only individual closed circles (•). As presented in FIG. 19, growth rate is represented along the x axis, with slower growth (fewer cell divisions) on the left side of the graph and faster growth (more cell divisions) on the right side of the graph. Values on the y axis represented individual wells for each well plate.

The curves (solid line) for well plates incubated in the test incubator showed no delay in growth relative to the curves for the well plates incubated entirely within the control incubator. The results demonstrated a lack of deleterious effect of incubation within the test incubator during the critical initial 24 hr period after seeding. Additionally, the curves for the well plates incubated in the test incubator exhibited less spread along the x axis, which indicates more uniform growth across the well plate (e.g., more similar number of cell divisions for all wells across the well plate) compared to the curves representing the growth of cells incubated entirely in the control incubator.

Example 2: OKT3 Cell Viability in a Well Plate Incubator

Materials: OKT3 cells, a murine myeloma hybridoma cell line, are obtained from the ATCC (ATCC® Cat # CRL-8001™). The cells are provided as a suspension cell line.

Cultures are maintained by seeding at about $1\times10^5$ to about $2\times10^5$ viable cells/mL and incubating at 37° C., using 5% carbon dioxide gaseous environment. Cells are split every 2-3 days. OKT3 cell number and viability are counted and cell density is adjusted to $5\times10^5$/ml for loading into well plates for incubation in the continuous access well plate incubator.

Culture medium: 500 ml Iscove's Modified Dulbecco's Medium (IMDM, ATCC® Cat #30-2005), 200 ml Fetal Bovine Serum (ATCC® Cat #30-2020) and 1 ml penicillin-streptomycin (Life Technologies® Cat #15140-122) are combined to make the culture medium. The complete medium is filtered through a 0.22 μm filter and stored away from light at 4° C. until use. The culture medium is conditioned with 5% carbon dioxide in air before introduction into the incubator.

Incubator: Manufactured by Berkeley Lights, Inc., includes a lid, shutter, and temperature and environment inputs as described above. The temperature of the incubator is maintained at 37° C. and is kept under a positive gas pressure by flowing 5% carbon dioxide in air through the incubator at a flow rate of about 10 liters per hr. The gas mixture is humidified to a 90% relative humidity prior to entry into the incubator.

Cell culture plates: Falcon® 96 well U bottom plates are used (Corning, Cat #351177).

Viability Assay: Two 96 well cell culture plates are seeded, with each well receiving 10 cells of OKT3 cells, 100 microliters of IMDM culture medium, prepared as described above, is added to each well of both well plates. Each of the two well plates have the same distribution of cell types in the same locations within the well plate. A first well plate of the two plates, is placed directly into a standard tissue culture incubator, such as Heracell™ 150i (Fisher Scientific, Cat #51026283). The second experimental well plate is placed into the well plate incubator having continuous access. Both incubators are maintained at the same temperature (37° C.), and under the same environmental conditions, including conditioned gas having 5% carbon dioxide. Humidity is maintained in both systems at 90%.

After 24 h, the experimental well plate is removed from the well plate incubator having continuous access, and is put into the same model of commercially available tissue culture incubator as described above which is maintained at the same conditions as described above. Both control and experimental well plates are cultured for a further 6 days. At the conclusion of 7 days total culture time, cell viability is evaluated and an approximate cell count is obtained. CellTiterGlo® (Promega Corp.) luciferase assay is used to homogeneously lyse the cells and generate a luminescent signal, oxyluciferin, proportional the amount of ATP present, which in turn is directly proportional to the number of cells present. An equivalent amount of CellTiterGlo® Reagent is added directly to each well and the resultant luminescence is recorded on the Wallac 1420 Victor²™ (PerkinElmer, Cat #1420-832). The luminescence produced is directly proportional to the number of viable cells, and approximates the number of live cells within each well. Comparative viability/growth is based on the numbers of cells/well in experimental plates vs control.

The results indicate that cell viability in the experimental well plate is at least 95% of control for each cell line evaluated.

Example 3: Culture of OKT3 Cells in a Continuous Access Well Plate Incubator and Transfer to a Microfluidic Device Microfluidic Device Materials: Microfluidic devices and System: Manufactured by Berkeley Lights, Inc. The system includes at least a flow controller, temperature controller, fluidic medium conditioning and pump component, light source and projector for light activated DEP configurations, mounting stage, and a camera. The microfluidic device includes flow channels and pens for cell isolation, assay, and/or growth, with single pen volume of approximately $1.5\times10^6$ μm³.

Transfer component of the System: A linear stages robot, import/export tip having an outer diameter of 1.067 mm of the microfluidic device.

Priming solution for microfluidic device: The culture medium (as described in Example 2) containing 0.1% Pluronic® F127 (Life Technologies® Cat # P6866).

Preparation of the microfluidic device prior to transfer: The microfluidic device is loaded onto the system and purged with 100% carbon dioxide at 15 psi for 5 min. Immediately following the carbon dioxide purge, the priming solution is perfused through the microfluidic device at 8 μl/sec until a total volume of 2.5 ml is perfused through the microfluidic device. The culture medium is then flowed through the microfluidic device at 8 μl/sec until a total of 1 ml of culture medium is perfused through the microfluidic device. The temperature of the microfluidic device is maintained at 37° C. Culture medium is perfused throughout the experiment using a variable perfusion method which includes one 4 h period of perfusion at 0.01 μl/sec, followed by a short high velocity perfusion at 8 μl/sec for about 3 sec, interspersed by short perfusion stop periods of less than a minute.

Experiment: OKT3 cells are seeded into each well of a 96 well cell culture plate. The cells are cultured within the continuous access well plate incubator for 1 day. At the end of the culture period, analysis to determine cell viability and numbers of cells is performed on one well of the 96 well plate. After determining that viability and growth requirements have been met, the microfluidic device is prepared for transfer. The openings in the enclosure of the well plate incubator are opened by the controller of the well plate incubator, and positive gas flow is continued. For each well transferred, a mixing tip is first introduced through the opening in the enclosure connecting the well to the exterior environment. Agitation is provided by withdrawing and then re-injecting 50 μl of the culture medium within the well to mix the cells, additionally dislodging any cells adhering to the walls of the well. Agitation is performed either prior to inserting the import/export tip or at the same time. A sample of the contents of the well is drawn into the import/export tip and delivered to the input of the microfluidic device. The cells are moved via flow, gravity or by dielectrophoresis forces through the channel of the microfluidic device and then placed into individual pens of the microfluidic device for further evaluation.

NUMBERED EMBODIMENTS OF THE INVENTION

1. An incubator comprising: an enclosure having an internal chamber configured to support a cell culture plate comprising a plurality of wells, wherein the enclosure comprises a plurality of openings configured to allow access to the wells of the cell culture plate; a temperature controller configured to maintain a temperature of the internal chamber within a desired range; a first heating/cooling device engaged directly or indirectly with the enclosure, the first heating/cooling device controlled by the temperature controller; and a sealing element comprising a first plurality of openings corresponding to at least a subset of the plurality of openings in the enclosure, wherein the sealing element is movable between a closed position where the sealing element occludes, and thereby seals, each of the plurality of openings in the enclosure and a first open position where the first plurality of openings of the sealing element are in register with the at least a subset of the plurality of openings in the enclosure, thereby providing access to the internal chamber of the enclosure and any cell culture plate contained therein.

2. The incubator according to embodiment 1, further comprising: at least one passage in the enclosure configured for gas entry; and a connector adapted to connect a pressurized gas source to the at least one passage, wherein the sealing element is configured to form a seal with the plurality of openings in the enclosure that allows the enclosure to maintain a pressure in the internal chamber between about 0.0005 psi to about 0.01000 psi above ambient pressure when gas from the pressurized gas source flows into the internal chamber.

3. The incubator according to any one of embodiments 1-2, wherein each opening of the plurality of openings in the enclosure has a diameter of about 1 mm to about 10 mm or about 1.0 mm, about 1.5 mm, about 2.0 mm, about 2.5 mm, about 3.0 mm, about 3.5 mm, about 4.0 mm, about 4.5 mm, about 5.0 mm, about 5.5 mm, about 6.0 mm, about 6.5 mm, about 7.0 mm, about 7.5 mm, about 8.0 mm, about 8.5 mm, about 9.0 mm, about 9.5 mm, or about 10.0 mm or any range defined by one of the foregoing sizes.

4. The incubator according to any previous embodiment, wherein the internal chamber has a volume of about 200 $cm^3$ to about 750 $cm^3$.

5. The incubator according to any previous embodiment, wherein the internal chamber has a volume of about 750 $cm^3$ to about 2000 $cm^3$.

6. The incubator according to any previous embodiment, wherein the cell culture plate is a 96-well plate or a 384-well plate.

7. The incubator according to any previous embodiment, wherein the plurality of openings in the enclosure are configured to be in register with the plurality of wells in the cell culture plate.

8. The incubator according to any previous embodiment, wherein the internal chamber includes a reservoir configured to hold a fluid.

9. The incubator according to any previous embodiment, wherein the enclosure comprises a base and a lid, the base and the lid defining the internal chamber.

10. The incubator according to any previous embodiment, wherein the enclosure comprises a base, a lid, and a front plate, the base, the lid and the front plate defining the internal chamber.

11. The incubator according to any one of embodiments 9-10, wherein the base is formed from a rigid material having a high thermal conductivity and low thermal capacitance.

12. The incubator according to any one of embodiments 9-11, wherein the base is configured with a hollow region forming part or all of the internal chamber of the enclosure.

13. The incubator according to any one of embodiments 10-12, wherein the base includes a bottom and four walls with one of the four walls having a height that is shorter than the height of the other three walls.

14. The incubator according to any one of embodiments 9-13, wherein the lid is formed from an insulating plastic.

15. The incubator according to any one of embodiments 9-14, wherein the lid includes an outer surface and an inner surface within the enclosure, the inner surface including one or more recesses.

16. The incubator according to embodiment 15, wherein the lid further includes an adhesive layer adhered to the inner surface, and wherein the adhesive layer is configured to prevent air within the enclosure from filling the one or more recesses.

17. The incubator according to any one of embodiments 15 or 16, wherein the one or more recesses substantially surround groups of openings of the plurality of openings in the enclosure, each group comprising two or more openings of the plurality.

18. The incubator according to any one of embodiments 9-17, wherein the lid includes one or more connectors configured to sealably connect the lid to the base.

19. The incubator according to embodiment 18, wherein the one or more connectors include a magnet, a flexible tab, and/or a clip.

20. The incubator according to embodiment 18, wherein the one or more connectors are flexible tabs, and wherein each flexible tab is configured to engage with a pin and thereby secure the lid to the base.

21. The incubator according to any previous embodiment, wherein the first plurality of openings of the sealing element is the same as the number of openings in the enclosure.

22. The incubator according to any previous embodiment, wherein the sealing element further comprises a second plurality of openings, the second plurality of openings being different from the first plurality of openings.

23. The incubator according to embodiment 22, wherein the number of openings in the first plurality of openings and/or the second plurality of openings in the sealing element is less than the number of openings in the enclosure.

24. The incubator according to any one of embodiments 22-23, wherein the number of openings in the second plurality of openings in the sealing element is one-half, one-third, or one-fourth the number of openings in the enclosure.

25. The incubator according to any previous embodiment, wherein the sealing element is movable between a closed position, a first open position, and a second open position, and wherein: when the sealing element is in the closed position, each of the plurality of the openings in the enclosure are occluded; when the sealing element is in the first open position, the first plurality of openings in the sealing element are in register with a first subset of the plurality of opening in the enclosure and all other openings of the plurality of openings in the enclosure are occluded; and when the sealing element is in the second open position, the first plurality of openings in the sealing element are in register with a second subset of openings in the enclosure and all other openings of the plurality of openings in the enclosure are occluded.

26. The incubator according to embodiment 25, wherein the first subset of openings in the enclosure and the second subset of openings in the enclosure are non-overlapping subsets.

27. The incubator according to any previous embodiment, wherein the sealing element is located inside the internal chamber of the enclosure.

28. The incubator according to any previous embodiment, further comprising: a sealing element actuator configured to move the sealing element between a first open position and a closed position.

29. The incubator according to embodiment 28, wherein the sealing element actuator is configured to move the sealing element between a second open position and the closed position or the first open position.

30. The incubator according to embodiment 29, wherein moving the sealing element to the second open position includes lining up the first plurality of openings of the sealing element with a second subset of the plurality of openings in the enclosure, wherein the second subset of the plurality of the openings in the enclosure is less than the plurality of openings in the enclosure.

31. The incubator according to any one of embodiments 28-30, wherein the sealing element actuator comprises a motor or rotary solenoid.

32. The incubator according to any previous embodiment, further comprising a printed circuit board (PCB).

33. The incubator according to embodiment 32, wherein the enclosure includes a base and a lid and the sealing element is located between the PCB and the lid.

34. The incubator according to any one of embodiments 32-33, further comprising: one or more sensors on the PCB.

35. The incubator according to embodiment 34, wherein each of the one or more sensors is selected from the group consisting of: a temperature sensor, a humidity sensor, an oxygen sensor, and a carbon dioxide sensor.

36. The incubator according to any previous embodiment, wherein the first heating/cooling device is selected from the group consisting of: a resistive heater, a fluid coil configured to circulate a heat exchange fluid, one or more Peltier devices, and combinations thereof.

37. The incubator according to any previous embodiment, wherein the first heating/cooling device directly contacts or indirectly provides heat transfer to an outer surface of the bottom of the enclosure.

38. The incubator according to embodiment 37, wherein the first heating/cooling device contacts at least about 75% of the outer surface of the bottom of the enclosure.

39. The incubator according to any previous embodiment, wherein the first heating/cooling device comprises a fluid coil.

40. The incubator according to any previous embodiment, further comprising: a second heating/cooling device, wherein the second heating/cooling device is adjacent a top of the enclosure and is controlled by the temperature controller.

41. The incubator according to embodiment 40, wherein the second heating/cooling device is within the enclosure.

42. The incubator according to any one of embodiments 40-41, wherein the second heating/cooling device comprises a plurality of openings that are in register with the plurality of openings in the enclosure.

43. The incubator according to any one of embodiments 40-42, wherein the second heating/cooling device comprises resistive heating elements that are part of the PCB.

44. The incubator according to embodiment 43, wherein the PCB comprises a plurality of openings in register with the plurality of openings passing through the enclosure.

45. The incubator according to any one of embodiments 43-44, wherein the resistive heating elements are positioned internally to the PCB as part of a multi-layer construction of the PCB.

46. The incubator of any one of the preceding embodiments, further comprising: a support for the cell culture plate.

47. The incubator according to embodiment 46, wherein the support is configured to slideably move relative to the enclosure from a position within the enclosure to a position outside of the internal chamber of the enclosure.

48. The incubator according to any one of embodiments 46-47, further comprising a distal lip on the support configured to engage an edge of the cell culture plate.

49. The incubator according to any one of embodiments 46-48, further comprising: an access door engaged with the support for the cell culture plate.

50. The incubator according to embodiment 49, wherein the support and access door form an access assembly including a front plate that sealably interfaces with a portion of the enclosure.

51. The incubator according to embodiment 50, further comprising: a biased connection between the front plate and the access door configured to provide a compressive force to the front plate.

52. The incubator according to any one of embodiments 50-51, wherein the access assembly is movably mounted on an enclosure support that supports the enclosure.

53. The incubator according to embodiment 52, further comprising: tracks on the enclosure support, wherein the access assembly is configured to slide relative to the tracks on the enclosure support.

54. The incubator according to embodiment 53, the access assembly further comprising rails configured to slide relative to the tracks on the enclosure support.

55. The incubator according to embodiment 54, further comprising: an engagement surface on the rails configured to engage with a complementary structure of the enclosure support to secure a position of the access assembly relative to the enclosure support.

56. The incubator according to embodiment 55, wherein the position of the access assembly corresponds to an open or closed position of the access assembly.

57. The incubator according to any one of embodiments 50-56, further comprising: a door switch configured to mechanically, electronically, or magnetically engage with a complementary structure of the access assembly.

58. The incubator according to embodiment 46, wherein the support is formed by one or more internal surfaces of the enclosure.

59. The incubator according to embodiment 2, wherein the at least one passage configured for gas entry is located on a wall of the base at the same height from a bottom of the base as a side of the cell culture plate.

60. The incubator according to any previous embodiment, further comprising: at least one fluid drain passage in the enclosure configured to drain a fluid reservoir within the enclosure, wherein the fluid drain passage is sealable.

61. The incubator according to any previous embodiment, further comprising: an insulation material coupled to the enclosure.

62. The incubator according to embodiment 61, wherein the insulation material is attached to one or more outer surfaces of the enclosure.

63. The incubator according to any previous embodiment, wherein the incubator is configured to maintain a selected internal temperature, humidity, and gas content within the internal chamber of the enclosure.

64. The incubator according to embodiment 63, further comprising: a controller configured to maintain the selected internal temperature, humidity, and gas content within the internal chamber of the enclosure.

65. The incubator according to any previous embodiment, further comprising: an enclosure support configured to support the enclosure.

66. The incubator according to embodiment 65, further comprising: one or more adjustable connectors configured to connect the enclosure support to the enclosure.

67. The incubator according to any previous embodiment, wherein each opening of the plurality of openings in the enclosure has a diameter of about 1 mm to about 5 mm or about 1.0 mm, about 1.5 mm, about 2.0 mm, about 2.5 mm, about 3.0 mm, about 3.5 mm, about 4.0 mm, about 4.5 mm, or about 5.0 mm or any range defined by one of the foregoing sizes.

68. The incubator according to any previous embodiment, wherein each of the plurality of openings in the sealing element has a diameter of about 1 mm to about 10 mm or about 1.0 mm, about 1.5 mm, about 2.0 mm, about 2.5 mm, about 3.0 mm, about 3.5 mm, about 4.0 mm, about 4.5 mm, about 5.0 mm, about 5.5 mm, about 6.0 mm, about 6.5 mm, about 7.0 mm, about 7.5 mm, about 8.0 mm, about 8.5 mm, about 9.0 mm, about 9.5 mm, or about 10.0 mm or any range defined by one of the foregoing sizes.

69. The incubator according to any previous embodiment, wherein each of the plurality of openings in the sealing element has a diameter of about 1 mm to about 5 mm or about 1.0 mm, about 1.5 mm, about 2.0 mm, about 2.5 mm, about 3.0 mm, about 3.5 mm, about 4.0 mm, about 4.5 mm, or about 5.0 mm, or any range defined by one of the foregoing sizes.

70. A method for accessing an internal chamber of an incubator, wherein the incubator comprises an enclosure having a plurality of openings and a sealing element having a plurality of openings corresponding to at least a subset of the plurality of openings in the enclosure, the method comprising: moving the sealing element to an open position and thereby bringing the plurality of openings in the sealing element into register with a first subset of openings of the plurality of openings in the enclosure, the plurality of openings in the sealing element and the first subset of openings of the plurality of openings in the enclosure thereby providing a first plurality of passages from an exterior of the incubator to an internal chamber of the enclosure; advancing an import/export tip through one or more of the first plurality of passages between the exterior of the incubator and the internal chamber of the enclosure; and collecting or depositing a material within the internal chamber of the enclosure via the import/export tip.

71. The method according to embodiment 70, wherein collecting or depositing the material comprises collecting or depositing the material within a well of a cell culture plate within the internal chamber of the enclosure.

72. The method according to any one of embodiments 70-71, further comprising: withdrawing the import/export tip through one or more of the passages between the exterior of the incubator and the internal chamber of the enclosure after collecting or depositing the material.

73. The method according to embodiment 72, further comprising: moving the sealing element to a closed position such that the sealing element occludes the plurality of openings in the enclosure.

74. The method according to any one of embodiments 70-73, wherein the sealing element is in the open position for an amount of time which is sufficiently short so as to prevent a carbon dioxide content and/or a humidity of air present in the internal chamber of the incubator from equilibrating with a carbon dioxide content and/or a humidity of air surrounding the incubator.

75. The method according to any one of embodiments 70-74, comprising: actuating a sealing element actuator to move the sealing element to the open position or closed position.

76. The method according to embodiment 75, wherein actuating the sealing element actuator comprises activating a motor or rotary solenoid.

77. The method according to any one of embodiments 70-76, wherein moving the sealing element between the open position and closed position comprises sliding the sealing element relative to the enclosure.

78. The method according to any one of embodiments 70-77, wherein when the plurality of openings in the sealing element are in the open position, the plurality of openings are configured to be in register with a plurality of wells in the cell culture plate.

79. The method according to any one of embodiments 70-78, wherein the incubator comprises a support within the internal chamber of the enclosure configured to support the cell culture plate.

80. The method according to embodiment 79, further comprising: sliding the support to a position outside of the internal chamber of the enclosure and thereby withdrawing the cell culture plate from the internal chamber of the enclosure.

81. The method according to embodiment 80, wherein sliding the support includes sliding an access door attached to the support.

82. The method according to any one of embodiments 80-81, wherein sliding the support includes sliding along one or more tracks of an enclosure support of the incubator.

83. The method according to any one of embodiments 80-82, wherein sliding the support is performed by a human operator.

84. The method according to any one of embodiments 80-82, wherein sliding the support is performed robotically.

85. The method according to embodiment 79, further comprising: sliding the support to withdraw the support from the internal chamber of the incubator to a position outside of the internal chamber of the enclosure.

86. The method according to embodiment 85, further comprising: placing a cell culture plate on the support while the support is in the position outside of the internal chamber of enclosure.

87. The method according to embodiment 86, wherein placing the cell culture plate is performed by a human operator.

88. The method according to embodiment 86, wherein placing the cell culture plate is performed robotically.

89. The method according to any one of embodiments 85-88, further comprising: sliding the support to a position inside the internal chamber of the enclosure and thereby moving the cell culture plate into the internal chamber of the enclosure.

90. The method according to embodiment 89, wherein sliding the support comprises sliding an access door attached to the support for the cell culture plate.

91. The method according to any one of embodiments 89 or 90, wherein sliding the support comprises sliding along one or more tracks of an enclosure support of the incubator.

92. The method according to any one of embodiments 89-91, wherein sliding the support is performed by a human operator.

93. The method according to any one of embodiments 89-91, wherein sliding the support is performed robotically.

94. The method according to any one of embodiments 70-93, further comprising: measuring one or more of a temperature, a humidity, and a carbon dioxide content of the internal chamber of the enclosure.

95. The method according to any one of embodiments 70-94, further comprising: controlling one or more of a temperature, a humidity, and a carbon dioxide content of the internal chamber of the enclosure.

96. The method according to embodiment 95, wherein controlling the temperature comprises heating or cooling the internal chamber of the enclosure.

97. The method according to any one of embodiments 95 or 96, wherein controlling the humidity comprises providing a humidity source to the internal chamber of the enclosure.

98. The method according to any one of embodiments 95-97, wherein controlling the carbon dioxide content comprises providing a gas source comprising carbon dioxide to the internal chamber of the incubator.

99. The method according to embodiment 98, wherein the gas source comprising carbon dioxide further comprises oxygen and nitrogen.

100. The method according to any one of embodiments 70-99, wherein the sealing element, when in the closed position, is capable of maintaining a pressure within the internal chamber of the enclosure between about 0.0005 psi to about 0.0100 psi above ambient pressure.

101. The method according to embodiment 100, further comprising: providing a purge gas to the internal chamber of the enclosure whereby, when the sealing element is in the closed position and the support for the cell culture plate is positioned inside the internal chamber of the enclosure, the pressure within the internal chamber of the enclosure is maintained between about 0.0005 psi to about 0.0100 psi above ambient pressure.

102. The method according to any one of embodiments 70-101, wherein the import/export tip comprises a plurality of tips.

103. The method according to embodiment 102, further comprising: simultaneously collecting or depositing the material from a plurality of the wells of the cell culture plate using the plurality of tips of the import/export tip.

104. The method according to embodiment 103, wherein collecting or depositing the material is performed robotically.

105. The method according to any one of embodiments 70-104, further comprising: maintaining a pressure within the internal chamber of the incubator that is greater than a pressure outside of the incubator when the sealing element is in an open position.

106. The method according to any one of embodiments 70-105, wherein each opening of the plurality of openings in the enclosure has a diameter of about 1 mm to about 10 mm or about 1.0 mm, about 1.5 mm, about 2.0 mm, about 2.5 mm, about 3.0 mm, about 3.5 mm, about 4.0 mm, about 4.5 mm, about 5.0 mm, about 5.5 mm, about 6.0 mm, about 6.5 mm, about 7.0 mm, about 7.5 mm, about 8.0 mm, about 8.5 mm, about 9.0 mm, about 9.5 mm, or about 10.0 mm or any range defined by one of the foregoing sizes.

107. The method according to any one of embodiments 70-105, wherein each opening of the plurality of openings in the enclosure has a diameter of about 1 mm to about 5 mm, or about 1.0 mm, about 1.5 mm, about 2.0 mm, about 2.5 mm, about 3.0 mm, about 3.5 mm, about 4.0 mm, about 4.5 mm, or about 5.0 mm, or any range defined by one of the foregoing sizes.

108. The method according to any one of embodiments 70-107, wherein each opening of the plurality of openings in the sealing element has a diameter of about 1 mm to about 10 mm, or about 1.0 mm, about 1.5 mm, about 2.0 mm, about 2.5 mm, about 3.0 mm, about 3.5 mm, about 4.0 mm, about 4.5 mm, about 5.0 mm, about 5.5 mm, about 6.0 mm, about 6.5 mm, about 7.0 mm, about 7.5 mm, about 8.0 mm, about 8.5 mm, about 9.0 mm, about 9.5 mm, or about 10.0 mm or any range defined by one of the foregoing sizes.

109. The method according to any one of embodiments 70-107, wherein each opening of the plurality of openings in the sealing element has a diameter of about 1 mm to about 5 mm, or about 1.0 mm, about 1.5 mm, about 2.0 mm, about 2.5 mm, about 3.0 mm, about 3.5 mm, about 4.0 mm, about 4.5 mm, or about 5.0 mm, or any range defined by one of the foregoing sizes.

110. The method according to any one of embodiments 70-109, wherein the material collected or deposited in the internal chamber of the enclosure comprises a biological micro-object.

111. The method according to any one of embodiments 70-110, further comprising: establishing an environment within the internal chamber of the enclosure to support a biological micro-object cultured in the cell culture plate.

112. A method for accessing an internal chamber of an incubator, wherein the incubator comprises an enclosure having a plurality of openings and a sealing element having more than one plurality of openings, wherein each plurality of openings in the sealing element corresponds to at least a subset of the plurality of openings in the enclosure, the method comprising: moving the sealing element to a first open position and thereby bringing a first plurality of openings in the sealing element into register with a first subset of the plurality of openings in the enclosure, the first plurality of openings in the sealing element and the first subset of openings in the plurality of openings in the enclosure providing, when in register, a first plurality of passages from an exterior of the incubator to the internal chamber of the enclosure; advancing an import/export tip through one or more of the first plurality of passages between the exterior of the incubator and the internal chamber of the enclosure; and collecting or depositing a material with the import/export tip within the internal chamber of the enclosure.

113. The method according to embodiment 112, wherein, when the sealing element is in the open position, the first plurality of openings in the sealing element are configured to be in register with a first subset of a plurality of wells in the cell culture plate.

114. The method according to any one of embodiments 112 or 113, wherein a number of the plurality of openings in the sealing element is the same as a number of the plurality of wells in the cell culture plate.

115. The method according to any one of embodiments 112 or 113, wherein a number of the plurality of openings in the sealing element is equal to or less than one-half, one-third, one-fourth, one-sixth, or one-twelfth a number of the plurality of wells in the cell culture plate.

116. The method according to any one of embodiments 112-115, further comprising: moving the sealing element to a second open position, thereby bringing a second plurality of openings in the sealing element into register with a second subset of the plurality of openings in the enclosure, the second plurality of openings in the sealing element and the second subset of the plurality of openings in the enclosure, when in register, providing a second plurality of passages from an exterior of the incubator to the internal chamber of the enclosure.

117. The method according to embodiment 116, wherein, when the sealing element is in the second open position, all openings of the plurality of openings in the enclosure other than the second subset of openings are occluded by the sealing element 118. The method according to any one of embodiments 112-117, further comprising: moving the sealing element to a third open position, thereby bringing a third plurality of openings in the sealing element into register with a third subset of the plurality of openings in the enclosure, the third plurality of openings in the sealing element and the third subset of the plurality of openings in the enclosure, when in register, providing a third plurality of passages from an exterior of the incubator to the internal chamber of the enclosure.

119. The method according to embodiment 118, wherein, when the sealing element is in the third open position, all openings of the plurality of openings in the enclosure other than the third subset of openings are occluded by the sealing element.

120. The method according to any one of embodiments 112-119, further comprising: moving the sealing element to a closed position, and thereby occluding each of the plurality of the openings in the enclosure.

121. A system for incubation, comprising: the well plate incubator according to any one of embodiments 1-69; a robotic sampling component configured to access the well plate incubator to collect or deposit samples within an internal chamber of an enclosure of the well plate incubator; and at least one controller configured to: open a plurality of passages from an exterior of the incubator to the internal chamber of the enclosure; and control the robotic sampling component to access, via the plurality of passages, a plurality of wells of a well plate contained within the internal chamber of the enclosure.

122. The system according to embodiment 121, wherein the at least one controller is further configured to close the plurality of passages.

123. The system according to any one of embodiments 121-122, wherein the system is configured to maintain the internal chamber of the enclosure under positive pressure.

124. The system according to any one of embodiments 121-123, wherein the at least one controller is configured to control the robotic sampling component to withdraw a material from one of the plurality of wells of the well plate.

125. The system according to embodiment 124, wherein the at least one controller is configured to control the robotic sample component to deliver the withdrawn material to a microfluidic device.

126. The system according to embodiment 124, wherein the at least one controller is configured to control the robotic sample component to deliver the withdrawn material to an analytical instrument.

127. The system according to any one of embodiments 121-126, wherein the material comprises a biological micro-object.

128. The system according to any one of embodiments 121-127, wherein the at least one controller is configured to control the robotic sampling component to deliver one or more materials to one or more wells of the well plate contained within the well plate incubator.

129. The system according to embodiment 128, wherein the one or more materials are obtained from a microfluidic device.

130. The system according to embodiment 128, wherein the one or more materials are obtained from an analytical instrument.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims. Any titles or subdivisions within the description are meant for ease of reading and is in no way intended to limit the invention and the combinations and sub-combinations described herein.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An incubator comprising:
   an enclosure having an internal chamber configured to support a cell culture plate comprising a plurality of wells, wherein the enclosure comprises at least one passage configured for gas entry, a connector adapted to connect a pressurized gas source to the at least one passage, and a plurality of openings configured to allow access to the plurality of wells of the cell culture plate;
   a controller configured to maintain a temperature of the internal chamber within a desired range;
   a first heating/cooling device engaged directly or indirectly with the enclosure, the first heating/cooling device controlled by the controller; and
   a sealing element comprising a first plurality of openings corresponding to at least a subset of the plurality of openings in the enclosure,
   wherein the sealing element is movable between a closed position, a first open position, and a second open position, and wherein:
   when the sealing element is in the closed position, the sealing element occludes, and thereby seals, each of the plurality of openings in the enclosure;
   when the sealing element is in the first open position, the first plurality of openings of the sealing element are in register with a first subset of the plurality of openings in the enclosure, thereby providing access to the internal chamber of the enclosure and any cell culture plate contained therein, and all other openings of the plurality of openings in the enclosure are occluded;
   when the sealing element is in the second open position, the first plurality of openings in the sealing element are in register with a second subset of the plurality of openings in the enclosure and all other openings of the plurality of openings in the enclosure are occluded; and wherein, when the sealing element is in the closed position, the incubator is configured to maintain a selected internal temperature, humidity, and gas content within the internal chamber of the enclosure.

2. The incubator of claim 1, wherein each opening of the plurality of openings in the enclosure has a diameter of about 1 mm to about 10 mm, or about 1 mm to about 5 mm.

3. The incubator of claim 1, wherein the internal chamber has a volume of about 200 cm$^3$ to about 750 cm$^3$ or about 750 cm$^3$ to about 2000 cm$^3$.

4. The incubator of claim 1, wherein the cell culture plate is a 96-well plate or a 384-well plate.

5. The incubator of claim 1, wherein the plurality of openings in the enclosure are configured to be in register with the plurality of wells in the cell culture plate.

6. The incubator of claim 1, wherein the enclosure comprises a base and a lid, the base and the lid defining the internal chamber.

7. The incubator of claim 6, wherein the base is formed from a rigid material having a high thermal conductivity and low thermal capacitance and is configured with a hollow region forming part or all of the internal chamber of the enclosure, and wherein the lid is formed from an insulating plastic.

8. The incubator of claim 6, wherein the lid includes one or more connectors configured to sealably connect the lid to the base, and wherein each of the one or more connectors are selected from the group consisting of a magnet, a flexible tab, and/or a clip.

9. The incubator of claim 1, wherein the enclosure comprises a base, a lid, and a front plate, the base, the lid and the front plate defining the internal chamber.

10. The incubator of claim 9, wherein the base is formed from a rigid material having a high thermal conductivity and low thermal capacitance, wherein the base includes a bottom and four walls with one of the four walls having a height that is shorter than the height of the other three walls and is configured with a hollow region forming part or all of the internal chamber of the enclosure.

11. The incubator of claim 9, wherein the lid includes one or more connectors configured to sealably connect the lid to the base, and wherein each of the one or more connectors are selected from the group consisting of a magnet, a flexible tab, and/or a clip.

12. The incubator of claim 1, wherein the first subset of the plurality of openings in the enclosure and the second subset of openings in the enclosure are non-overlapping subsets.

13. The incubator of claim 1, wherein the sealing element is located inside the internal chamber of the enclosure.

14. The incubator of claim 1 further comprising: a sealing element actuator configured to move the sealing element between the first open position, the second open position, and the closed position.

15. The incubator of claim 1, wherein the first heating/cooling device is selected from the group consisting of: a resistive heater, a fluid coil configured to circulate a heat exchange fluid, one or more Peltier devices, and combinations thereof.

16. The incubator of claim 1 further comprising: a second heating/cooling device, wherein the second heating/cooling device is within the enclosure and is controlled by the controller.

17. The incubator of claim 16, wherein the second heating/cooling device comprises a PCB having resistive heating elements and one or more sensors, and wherein the PCB comprises a plurality of openings in register with the plurality of openings in the enclosure.

18. The incubator of claim 17, wherein the enclosure includes a base and a lid, and wherein the sealing element is located between the PCB and the lid.

19. The incubator of claim 17, wherein each of the one or more sensors is selected from the group consisting of: a temperature sensor, a humidity sensor, an oxygen sensor, and a carbon dioxide sensor.

20. The incubator of claim 1 further comprising: a support for the cell culture plate.

21. The incubator of claim 20, wherein the support is configured to slideably move relative to the enclosure from a position within the enclosure to a position outside of the internal chamber of the enclosure.

22. The incubator of claim 20 further comprising: an access door engaged with the support for the cell culture plate, wherein the support and access door form an access assembly including a front plate that sealably interfaces with a portion of the enclosure.

23. The incubator of claim 22 further comprising: a biased connection between the front plate and the access door configured to provide a compressive force to the front plate.

24. The incubator of claim 22 further comprising: an enclosure support configured to support the enclosure, wherein the access assembly is movably mounted on the enclosure support.

25. The incubator of claim 24, wherein:
the enclosure support comprises tracks;
the access assembly comprises rails configured to slide relative to the tracks on the enclosure support, the rails having an engagement surface configured to engage with a complementary structure of the enclosure support to secure a position of the access assembly relative to the enclosure support, and
the secured position of the access assembly corresponds to an open or closed position of the access assembly.

26. The incubator of claim 20, wherein the support is formed by one or more internal surfaces of the enclosure.

27. The incubator of claim 1, wherein the controller is further configured to maintain the humidity and gas content within the internal chamber of the enclosure.

28. The incubator of claim 1, wherein each of the plurality of openings in the sealing element has a diameter of about 1 mm to about 10 mm, or about 1 mm to about 5 mm.

29. The incubator of claim 1, wherein the sealing element is configured to form a seal with the plurality of openings in the enclosure that allows the enclosure to maintain a pressure in the internal chamber between about 0.0005 psi to about 0.01000 psi above ambient pressure when gas from the pressurized gas source flows through the connector and at least one passage into the internal chamber.

30. A method for accessing an internal chamber of an incubator, wherein the incubator is an incubator according to claim 1, the method comprising:
moving the sealing element to an open position, thereby bringing the first plurality of openings in the sealing element into register with the first subset of openings of the plurality of openings in the enclosure, the first plurality of openings in the sealing element and the first subset of openings of the plurality of openings in the enclosure thereby providing a first plurality of passages from an exterior of the incubator to an internal chamber of the enclosure;

advancing an import/export tip through one or more of the first plurality of passages between the exterior of the incubator and the internal chamber of the enclosure;

collecting or depositing a material within the internal chamber of the enclosure via the import/export tip;

withdrawing the import/export tip through one or more of the first plurality of passages between the exterior of the incubator and the internal chamber of the enclosure after collecting or depositing the material; and moving the sealing element to a closed position such that the sealing element occludes the plurality of openings in the enclosure, wherein the sealing element is in the open position for an amount of time which is sufficiently short so as to prevent a carbon dioxide content and/or a humidity of air present in the internal chamber of the incubator from equilibrating with a carbon dioxide content and/or a humidity of air surrounding the incubator.

31. The method of claim 30, wherein collecting or depositing the material comprises collecting or depositing the material within a well of a cell culture plate within the internal chamber of the enclosure.

32. A system for incubation, comprising:
the incubator of claim 1;
a robotic sampling component configured to access the incubator to collect or deposit samples within an internal chamber of an enclosure of the incubator; and
at least one controller configured to:
open a plurality of passages from an exterior of the incubator to the internal chamber of the enclosure; and
control the robotic sampling component to access, via the plurality of passages, a
plurality of wells of a well plate contained within the internal chamber of the enclosure.

33. An incubator comprising:
an enclosure having an internal chamber configured to support a cell culture plate comprising a plurality of wells, wherein the enclosure comprises at least one passage configured for gas entry, a connector adapted to connect a pressurized gas source to the at least one passage, and a plurality of openings configured to allow access to the plurality of wells of the cell culture plate;
a support for the cell culture plate, wherein the support is configured to slideably move relative to the enclosure from a position within the enclosure to a position outside of the internal chamber of the enclosure;
a controller configured to maintain a temperature of the internal chamber within a desired range;
a first heating/cooling device engaged directly or indirectly with the enclosure, the first heating/cooling device controlled by the controller; and
a sealing element comprising a first plurality of openings corresponding to at least a subset of the plurality of openings in the enclosure,
wherein the sealing element is movable between a closed position where the sealing element occludes, and thereby seals, each of the plurality of openings in the enclosure and a first open position where the first plurality of openings of the sealing element are in register with the at least a subset of the plurality of openings in the enclosure, thereby providing access to the internal chamber of the enclosure and any cell culture plate contained therein, and
wherein, when the sealing element is in the closed position, the incubator is configured to maintain a selected internal temperature, humidity, and gas content within the internal chamber of the enclosure.

34. The incubator of claim 33 further comprising: an access door engaged with the support for the cell culture plate, wherein the support and access door form an access assembly including a front plate that sealably interfaces with a portion of the enclosure.

35. The incubator of claim 34 further comprising: an enclosure support configured to support the enclosure, wherein the access assembly is movably mounted on the enclosure support; and wherein:
the enclosure support comprises tracks;
the access assembly comprises rails configured to slide relative to the tracks on the enclosure support, the rails having an engagement surface configured to engage with a complementary structure of the enclosure support to secure a position of the access assembly relative to the enclosure support, and
the secured position of the access assembly corresponds to an open or closed position of the access assembly.

36. The incubator of claim 34 further comprising: a biased connection between the front plate and the access door configured to provide a compressive force to the front plate.

* * * * *